US012318116B2

(12) United States Patent
Rousso et al.

(10) Patent No.: US 12,318,116 B2
(45) Date of Patent: Jun. 3, 2025

(54) CARDIAC LEAD EXTRACTION DEVICE

(71) Applicant: Xcardia Innovation Ltd, Rehovot (IL)

(72) Inventors: Benny Rousso, Rishon-LeZion (IL);
Rodny Zarini, Moshav Pedaya (IL);
David Maier Neustadter, Nof Ayalon (IL); Yonatan Levi, Tel Aviv (IL);
Naama Winetraub, Holon (IL); Lior Eshel, Rishon-LeZion (IL); Assaf Erell, Ramat-Gan (IL)

(73) Assignee: Xcardia Innovation Ltd, Rehovot (IL)

( * ) Notice: Subject to any disclaimer, the term of this patent is extended or adjusted under 35 U.S.C. 154(b) by 1075 days.

(21) Appl. No.: 16/641,724

(22) PCT Filed: Aug. 24, 2018

(86) PCT No.: PCT/IL2018/050937
§ 371 (c)(1),
(2) Date: Feb. 25, 2020

(87) PCT Pub. No.: WO2019/038773
PCT Pub. Date: Feb. 28, 2019

(65) Prior Publication Data
US 2020/0352552 A1    Nov. 12, 2020

Related U.S. Application Data

(60) Provisional application No. 62/668,898, filed on May 9, 2018, provisional application No. 62/549,996, filed on Aug. 25, 2017.

(51) Int. Cl.
*A61B 17/34*    (2006.01)
*A61B 17/00*    (2006.01)
*A61B 17/32*    (2006.01)

(52) U.S. Cl.
CPC .... *A61B 17/3468* (2013.01); *A61B 17/00234* (2013.01); *A61B 17/32002* (2013.01);
(Continued)

(58) Field of Classification Search
CPC ........ A61B 17/00234; A61B 17/32002; A61B 2017/00243; A61B 2017/003;
(Continued)

(56) References Cited

U.S. PATENT DOCUMENTS 4,461,305 A    7/1984   Cibley
4,471,777 A    9/1984   McCorkle, Jr.
(Continued)

FOREIGN PATENT DOCUMENTS

CA    2862611    8/2012
JP    4076320    4/2008
(Continued)

OTHER PUBLICATIONS

Cook Medical "Byrd Dilator Sheath Set. Polypropylene or Teflon: Instructions for Use", Cook Medical, Brochure, p. 1-71, Aug. 2014.
(Continued)

*Primary Examiner* — Sarah A Long

(57) ABSTRACT

The invention relates to a cardiac lead extraction device, comprising: a handle; an elongated body having a first proximal end, a first distal end, and a first lumen extending from said first proximal end toward said first distal end, said lumen sized and shaped to fit over a cardiac lead; a controllable bendable flexible portion more flexible that said elongated body and having a second proximal end, a second distal end and a second lumen extending from said second proximal end toward said second distal end, said lumen sized and shaped to fit over a cardiac lead; said second proximal end interconnected to said first distal end; said second distal end interconnected to an operational distal end;
(Continued)

wherein said operational distal end comprises at least one lead extraction assistive tool, said lead extraction helping tool is activated by a motor located at said handle or proximally to said handle.

33 Claims, 61 Drawing Sheets

(52) U.S. Cl.
CPC ............... *A61B 2017/00243* (2013.01); *A61B 2017/003* (2013.01); *A61B 2017/00358* (2013.01); *A61B 2017/320032* (2013.01); *A61B 2017/32004* (2013.01)

(58) Field of Classification Search
CPC ......... A61B 2017/00358; A61B 2017/320032; A61B 2017/32004; A61B 17/3468
See application file for complete search history.

(56) References Cited

U.S. PATENT DOCUMENTS

| | | | |
|---|---|---|---|
| 4,576,162 | A | 3/1986 | McCorkle |
| 5,423,806 | A | 6/1995 | Dale et al. |
| 5,507,751 | A | 4/1996 | Goode et al. |
| 5,620,451 | A | 4/1997 | Rosborough |
| 5,779,715 | A | 7/1998 | Tu |
| 5,980,515 | A | 11/1999 | Tu |
| 5,980,545 | A | 11/1999 | Pacala et al. |
| 6,033,402 | A | 3/2000 | Tu et al. |
| 6,183,469 | B1 | 2/2001 | Thapliyal et al. |
| 6,241,692 | B1 | 6/2001 | Tu et al. |
| 6,419,674 | B1 | 7/2002 | Bowser et al. |
| 6,512,959 | B1 | 1/2003 | Gomperz et al. |
| 7,072,703 | B2 | 7/2006 | Zhang et al. |
| 8,326,437 | B2 | 12/2012 | Cully et al. |
| 8,454,680 | B2 | 6/2013 | Verma |
| 9,032,806 | B2 | 5/2015 | Verma |
| 9,126,032 | B2 | 9/2015 | Khairkhahan et al. |
| 9,149,290 | B2 | 10/2015 | Goode et al. |
| 9,301,773 | B2 | 4/2016 | Olomutzki et al. |
| 9,414,783 | B2 | 8/2016 | Verma |
| 9,586,041 | B2 | 3/2017 | Goode et al. |
| 9,649,490 | B2 | 5/2017 | Booker |
| 9,801,650 | B2 | 10/2017 | Taylor et al. |
| 9,839,393 | B2 | 12/2017 | Verma |
| 2006/0235431 | A1 | 10/2006 | Goode et al. |
| 2006/0253179 | A1 | 11/2006 | Goode et al. |
| 2008/0071341 | A1* | 3/2008 | Goode ............. A61B 17/32002 607/122 |
| 2008/0071342 | A1 | 3/2008 | Goode et al. |
| 2009/0234367 | A1 | 9/2009 | Verma |
| 2010/0198229 | A1 | 8/2010 | Olomutzki et al. |
| 2010/0222787 | A1 | 9/2010 | Goode et al. |
| 2014/0277037 | A1 | 9/2014 | Grace et al. |
| 2014/0288572 | A1 | 9/2014 | Olomutzki et al. |
| 2014/0357997 | A1 | 12/2014 | Hartmann et al. |
| 2015/0057610 | A1* | 2/2015 | Osypka ............. A61B 17/3468 604/95.04 |
| 2015/0057672 | A1 | 2/2015 | Kalmann et al. |
| 2015/0150587 | A1* | 6/2015 | Smith ............ A61B 17/320758 606/159 |
| 2015/0327919 | A1* | 11/2015 | Clopp ................. A61B 17/3205 606/41 |
| 2015/0374398 | A1 | 12/2015 | Tobis |
| 2016/0022302 | A1 | 1/2016 | Olomutzki et al. |
| 2016/0310703 | A1 | 10/2016 | Drake et al. |
| 2016/0374721 | A1 | 12/2016 | Olomutzki et al. |
| 2017/0100161 | A1 | 4/2017 | Aslcson et al. |
| 2017/0360466 | A1* | 12/2017 | Brown ............. A61B 17/32002 |
| 2018/0028258 | A1 | 2/2018 | Zamarripa et al. |
| 2018/0064391 | A1 | 3/2018 | Verma |
| 2019/0030324 | A1* | 1/2019 | Grace .................. A61N 1/0573 |
| 2022/0047292 | A1 | 2/2022 | Rousso et al. |

FOREIGN PATENT DOCUMENTS

| | | |
|---|---|---|
| WO | WO 2011/123342 | 10/2011 |
| WO | WO 2012/114333 | 8/2012 |
| WO | WO 2012/114334 | 8/2012 |
| WO | WO 2014/151814 | 9/2014 |
| WO | WO 2015/170332 | 11/2015 |
| WO | WO 2016/100522 | 6/2016 |
| WO | WO 2016/100522 A9 | 6/2016 |
| WO | WO 2019/038773 | 2/2019 |
| WO | WO 2019/038773 A9 | 2/2019 |
| WO | WO 2020/174479 | 9/2020 |
| WO | WO 2023/007498 | 2/2023 |

OTHER PUBLICATIONS

Cook Medical "Devices for Lead Extraction", Cook Medical, Brochure, p. 1-16, Oct. 2014.

Cook Medical "Evolution® RL Controlled-Rotation Dilator Sheath Set: Instructions for Use", Cook Medical, Brochure, p. 1-76, Aug. 2014.

Cook Medical "Peel-Away—Introducer Sheath Set", Cook Medical, Inc., Product Description, 2 P., 2010.

Cook Vascular "Evolution® RL Controlled-Rotation Dilator Sheath Set and Evolution® Shortie RL Controlled-Rotation Dilator Sheath Set", Cook Vascular, Inc., FDA, Department of Human and Health Services, 510(k) Summary: K141148, 8 P., Jul. 1, 2014.

FDA "Evolution Mechanical Dilator Sheath Set, Evolution Shortie Mechanical Dilator Sheath Set, SteadySheath Evolution Tissue Stabilization Sheath, SteadySheath Evolution Shortie Tissue Stabilization Sheath", FDA, Department of Human and Health Services, 510(k) No. K142301, 6 P., Nov. 12, 2014.

FDA "TightRail Rotating Dilator Sheath, TightRail Mini Rotating Dilator Sheath", Spectranetics, Inc., FDA, Department of Human and Health Services, Design Verification and Validation Testing, 510(k) No. K150360, 5 P., Mar. 4, 2015.

FDA "TightRail Rotating Dilator Sheath/TightRail Mini Dilator Sheath", Spectranetics, Inc., FDA, Department of Human and Health Services, 510(k) No. K142546, 6 P., Sep. 25, 2014.

FDA "TightRail Sub-C Rotating Dilator Sheath", Spectranetics, Inc., FDA, Department of Human and Health Services, 510(k) No. K161333, 5 P., Jul. 8, 2016.

Ferguson "Cook Vascular Evolution Mechanical Dilator Sheath Set", Cook Vascular, Inc., FDA, Department for Human & Health Services, 510(k) Summary: K 061000, 5 P., Apr. 10, 2006.

Kusumoto et al. "2017 HRS Expert Consensus Statement on Cardiovascular Implantable Electronic Device Lead Management and Extraction", Heart Rhythm, 14(12): e503-e600, Dec. 2017.

Maytin et al. "Virtual Reality Lead Extraction as a Method for Training New Physicians: A Pilot Study", Pace, 38(3): 319-325, Published Online Dec. 12, 2014.

Spectranetics "GlideLight™ Laser Sheath: Instruction for Use", Spectranetics, P005831-09, p. 1-12, Mar. 10, 2016.

Spectranetics "SightRail—Manual Dilator Sheath: Instructions for Use", Spectranetics, Inc., 1 P., Jul. 7, 2014.

Supplementary European Search Report and the European Search Opinion Dated Oct. 20, 2022 From the European Patent Office Re. Application No. 20763111.0. (6 Pages).

Spectranetics "TightRail Sub-C Rotating Dilator Sheath", Spectranetics, Inc., Premarket Notification 510(K) No. K161333, FDA, U.S. Food and Drug Administration, 3 P., Oct. 1, 2018.

Spectranetics "TightRail™ & TightRail Mini™ Rotating Dilator Sheaths—The Next Generation in Mechanical Lead Extraction Sheaths", Spectranetics, Brochure, 4 P., 2014.

Spectranetics "TightRail™ Mechanical Dilator Sheath Set", Spectranetics, Inc., 510(k) Summary: K140047, FDA, Department of Human and Health Services, 6 P., Mar. 20, 2014.

Invitation to Pay Additional Fees Dated Jun. 4, 2020 From the International Searching Authority Re. Application No. PCT/IL2020/050230. (2 Pages).

International Search Report and the Written Opinion Dated Nov. 7, 2022 From the International Searching Authority Re. Application No. PCT/IL2022/050819. (18 Pages).

(56) References Cited

OTHER PUBLICATIONS

International Search Report and the Written Opinion Dated Dec. 10, 2018 From the International Searching Authority Re. Application No. PCT/IL2018/050937. (18 Pages).
International Preliminary Report on Patentability Dated Mar. 5, 2020 From the International Bureau of WIPO Re. Application No. PCT/IL2018/050937. (9 Pages).
International Preliminary Report on Patentability Dated Sep. 10, 2021 From the International Bureau of WIPO Re. Application No. PCT/IL2020/050230. (8 Pages).
Supplementary European Search Report and the European Search Opinion Dated Apr. 28, 2021 From the European Patent Office Re. Application No. 18847599.0. (7 Pages).
Communication Pursuant to Article 94(3) EPC Dated Jun. 14, 2023 From the European Patent Office Re. Application No. 18847599.0 (5 Pages).
Communication Pursuant to Article 94(3) EPC Dated Jan. 4, 2024 From the European Patent Office Re. Application No. 20763111.0 (3 Pages).
International Preliminary Report on Patentability Dated Feb. 8, 2024 From the International Bureau of WIPO Re. Application No. PCT/IL2022/050819 (10 Pages).
Communication Pursuant to Article 94(3) EPC Dated Jan. 16, 2024 From the European Patent Office Re. Application No. 18847599.0 (6 Pages).
International Search Report and the Written Opinion Dated Aug. 12, 2020 From the International Searching Authority Re. Application No. PCT/IL2020/050230. (11 Pages).

* cited by examiner

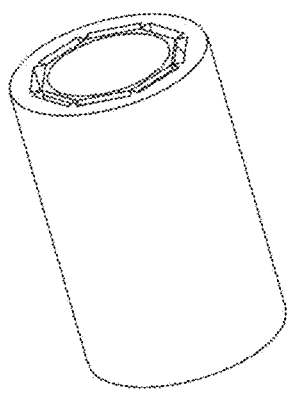
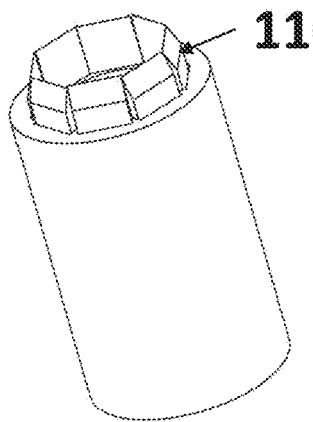
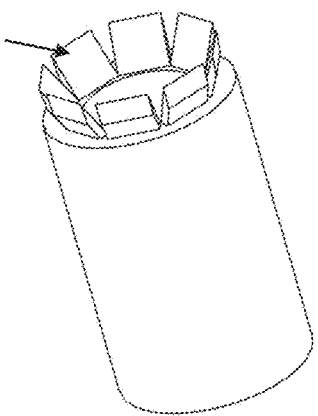
Figure 11a    Figure 11b    Figure 11c
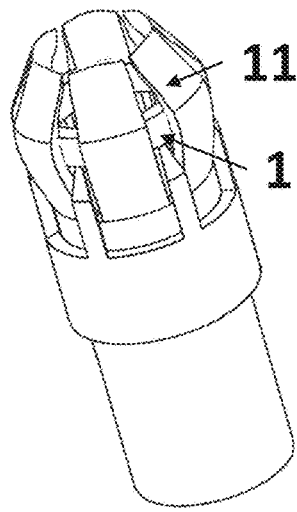
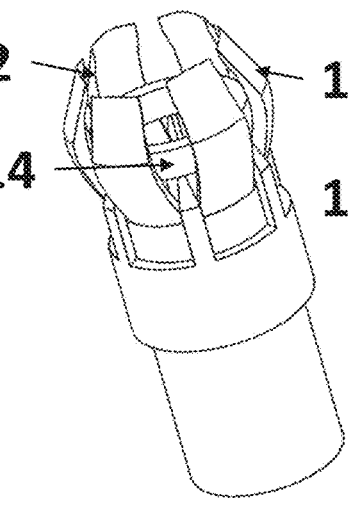
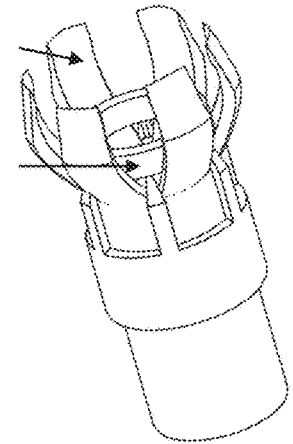
Figure 11d    Figure 11e    Figure 11f
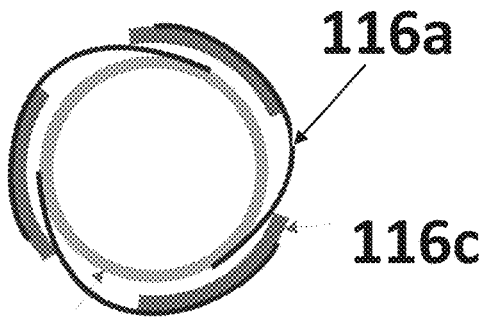
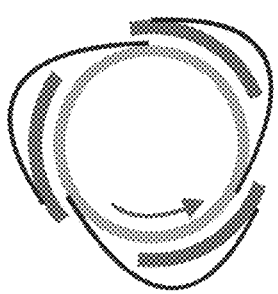
Figure 11g    Figure 11h    Figure 11i

244

244

290 →
290 →

322

CARDIAC LEAD EXTRACTION DEVICE

RELATED APPLICATIONS

This application is a National Phase of PCT Patent Application No. PCT/IL2018/050937 having International filing date of Aug. 24, 2018, which claims the benefit of priority under 35 USC § 119 (e) of U.S. Provisional Patent Applications No. 62/668,898 filed on May 9, 2018 and No. 62/549,996 filed on Aug. 25, 2017. The contents of the above applications are all incorporated by reference as if fully set forth herein in their entirety.

FIELD AND BACKGROUND OF THE INVENTION

The indications and populations requiring the removal of pacemaker and defibrillator leads appears to be growing and may be expected to continue to grow. The removal of cardiac leads may be complicated by, for example, the development of encapsulating fibrous tissue around the leads at certain locations within the veins and the heart, and the removal procedure highly depends on the experience of the physician. In some cases, removing the lead includes separating the tissue from either the lead and/or the vein. For example, tissue may be cut and/or ablated in order to remove the lead. A device for removing such leads may include a telescoping sheath. For example, the telescoping sheath may be used to manually dilate the fibrous tissue. Some solutions disclose, for example, a mechanical rotating sheath used to dilate the tissue more aggressively than the manual sheaths. Some solutions disclose, for example, a laser and/or an RF ablation sheath used to ablate the fibrous tissue. Sometimes serious complications may occur due to removal of leads. For example, forces that are exerted on the lead, the vein, and/or the heart tissue in order to free the lead from the fibrous tissue may occasionally cause serious damage to the walls of the veins and the heart.

SUMMARY OF THE INVENTION

The following describe some examples of embodiments of the invention. Other embodiments are within the scope of the description, including embodiments in which only some of the features from one example are used and embodiments in which one or more features are selected from two or more examples.

EXAMPLE 1

A cardiac lead extraction device, comprising:
a. a handle;
b. an elongated body having a first proximal end, a first distal end, and a first lumen extending from said first proximal end toward said first distal end, said lumen sized and shaped to fit over a cardiac lead;
c. a controllable bendable flexible portion more flexible that said elongated body; said flexible portion having a second proximal end, a second distal end and a second lumen extending from said second proximal end toward said second distal end, said lumen sized and shaped to fit over a cardiac lead; said second proximal end interconnected to said first distal end; and said second distal end interconnected to an operational distal end;
wherein said operational distal end comprises at least one lead extraction assistive tool, said lead extraction helping tool is activated by a motor located at said handle or proximally to said handle.

EXAMPLE 2

The device of example 1, wherein the inner diameter of said cardiac lead extraction device is from about 3 mm to about 7 mm.

EXAMPLE 3

The device of examples 1 or 2, wherein the outer diameter of said cardiac lead extraction device is from about 6 mm to about 8 mm.

EXAMPLE 4

The device of examples 1-3, wherein said controllable bendable flexible portion bends to a maximal angle of from about 35 degrees to about 150 degrees.

EXAMPLE 5

The device of example 4, wherein an inner diameter of said controllable bendable flexible portion changes from about 0% to about 10% during said maximal angle.

EXAMPLE 6

The device of examples 1-5, wherein said controllable bendable flexible portion comprises an articulated structure having multiple non-flexible components.

EXAMPLE 7

The device of examples 4-6, wherein said controllable bendable flexible portion is capable of bending to said maximal angle while withstanding forces from about 500 gr to about 1000 gr.

EXAMPLE 8

The device of example 1, wherein said lead extraction assistive tool comprises a tissue cutter.

EXAMPLE 9

The device of example 8, wherein said tissue cutter comprises at least one movable blade.

EXAMPLE 10

The device of examples 8 or 9, wherein said tissue cutter comprises at least one transmission attached to said motor; said transmission adapted to transfer motion from said motor to said at least one movable blade.

EXAMPLE 11

The device of example 10, wherein said motion of said at least one movable blade is linear.

EXAMPLE 12

The device of examples 10 or 11, wherein said motion of said at least one movable blade is circular.

EXAMPLE 13

The device of examples 10-12, wherein said movement of said transmission is adapted to provide said at least one movable blade with a linear movement comprising impact force.

EXAMPLE 14

The device of examples 10-13, wherein said motion of said at least one movable blade is a combination of linear movement and circular movement.

EXAMPLE 15

The device of examples 10-14, wherein said motion of said at least one movable blade is characterized by a frequency from about 0.5 Hz to about 100 Hz.

EXAMPLE 16

The device of example 10-15, wherein said motion of said at least one movable blade is characterized by a frequency from about 1 Hz to about 15 Hz.

EXAMPLE 17

The device of examples 10-16, wherein said at least one movable blade comprises a retracted state where said at least one movable blade is not exposed thereby avoiding said at least one movable blade from cutting.

EXAMPLE 18

The device of examples 10-17, wherein said at least one movable blade exits distally said operational distal end from about 0.15 mm to about 2 mm.

EXAMPLE 19

The device of example 8, wherein said tissue cutter comprises at least two movable blades.

EXAMPLE 20

The device of example 19, wherein the movement of said at least two movable blades is towards each therefore allowing cutting by shearing.

EXAMPLE 21

The device of example 1, wherein said elongated body comprises an inner bending shaft.

EXAMPLE 22

The device of example 21, wherein said inner bending shaft is as long as said elongated body.

EXAMPLE 23

The device of examples 21 or 22, wherein said inner bending shaft transmits motion from said handle to said operational distal end through said elongated body.

EXAMPLE 24

The device of example 1, wherein said controllable bendable flexible portion comprises an inner shaft.

EXAMPLE 25

The device of example 1, wherein said lead extraction assistive tool comprises a lead cutter.

EXAMPLE 26

The device of example 25, wherein said lead cutter comprises at least one blade and at least one movable part.

EXAMPLE 27

The device of examples 25 or 26, wherein said lead cutter engages a cardiac lead within said lumen with said at least one movable part and moves said cardiac lead against said at least one blade.

EXAMPLE 28

The device of examples 25-27, wherein said lead cutter comprises a groove, not aligned with the general direction of said lumen, where said cardiac lead is cut.

EXAMPLE 29

The device of examples 25-28, wherein at least one blade is located in said movable part.

EXAMPLE 30

The device of examples 25-29, wherein at least one blade is not located in said movable part.

EXAMPLE 31

The device of examples 25-30, wherein the movement of said at least one movable part is a linear movement.

EXAMPLE 32

The device of examples 25-31, wherein the movement of said at least one movable part comprises a screw rotating mechanism.

EXAMPLE 33

The device of example 1, wherein said lead extraction assistive tool comprises a tissue identification tool.

EXAMPLE 34

The device of example 33, wherein said tissue identification tool comprises at least one light emitting component, which is mechanically positioned to radiate in a direction aligned in front with the distal head of said device.

EXAMPLE 35

The device of examples 33 or 34, wherein said tissue identification tool comprises an electronic phased array of transducers stationary placed around the distal end of said operational distal end.

EXAMPLE 36

The device of example 1, wherein said lead extraction assistive tool comprises a steering tool.

EXAMPLE 37

The device of example 36, wherein said steering tool comprises at least one wire that runs from said handle to said operational distal end.

EXAMPLE 38

The device of examples 36 or 37, wherein said at least one wire runs inside a counter sleeve on said elongated sheath.

EXAMPLE 39

The device of example 1, wherein said lead extraction assistive tool comprises a tissue separator.

EXAMPLE 40

The device of example 39, wherein said tissue separator vibrates said operational distal end.

EXAMPLE 41

The device of examples 39 or 40, wherein said vibration is generated by said steering tool.

EXAMPLE 42

The device of examples 39-41, wherein said vibration comprises at least two-axis movement.

EXAMPLE 43

The device of examples 39-42, wherein said vibration is in the range from about 1 Hz to about 100 Hz.

EXAMPLE 44

The device of examples 39-43, wherein said tissue separator comprises fixed protrusions from the distal end of said operational distal end.

EXAMPLE 45

The device of examples 39-44, wherein said tissue separator comprises movable protrusions, which extend radially and outwardly.

EXAMPLE 46

The device of example 1, wherein said lead extraction assistive tool comprises a force analysis tool.

EXAMPLE 47

The device of example 46, wherein said force analysis tool provides indication of the forces applied between said device and the tissue surrounding said device.

EXAMPLE 48

The device of examples 46 or 47, wherein said force analysis tool provides indication of the forces applied between said device and said lead.

EXAMPLE 49

A lead extraction accessory, comprising:
a. a handle;
b. an elongated body having a first proximal end, a first distal end, and a first lumen extending from said first proximal end toward said first distal end, said lumen sized and shaped to fit over a cardiac lead extraction device;
c. said elongated body comprising a controllable bendable flexible portion having a second proximal end and a second distal end, said second distal end interconnected to an operational distal end;
wherein said operational distal end comprises at least one lead extraction assistive tool.

EXAMPLE 50

The lead extraction accessory of example 49, wherein a motor located at said handle activates said at least one lead extraction assistive tool.

EXAMPLE 51

A cardiac lead cutter device, comprising:
a. an elongated body having a proximal end, a distal end and a lumen extending from said proximal end toward said distal end, said lumen sized and shaped to fit over a cardiac lead; and
b. a lead cutter tool located at said distal end of said device, said lead cutter component comprises at least one blade and at least one movable part;
wherein said movable part engages said cardiac lead and moves said cardiac lead against said at least one blade.

EXAMPLE 52

The device of example 51, wherein said lead cutter comprises a groove, not aligned with the general direction of said lumen, where said cardiac lead is cut.

EXAMPLE 53

The device of examples 51 or 52, wherein at least one blade is located in said movable part.

EXAMPLE 54

The device of examples 51-53, wherein at least one blade is not located in said movable part.

EXAMPLE 55

The device of examples 51-54, wherein the movement of said at least one movable part is a linear movement.

EXAMPLE 56

The device of examples 51-55, wherein the movement of said at least one movable part comprises a screw rotating mechanism.

EXAMPLE 57

A tissue cutter device for a cardiac lead, comprising:
a. an elongated body having a proximal end, a distal end and a lumen extending from said proximal end toward said distal end, said lumen sized and shaped to fit over a cardiac lead; and b. a tissue cutter located at said distal end of said device, said tissue cutter comprises at least two separate movable blades.

EXAMPLE 58

The device of example 57, wherein said tissue cutter comprises at least one transmission attached to a motor; said transmission adapted to transfer motion from said motor to said at least two movable blades.

EXAMPLE 59

The device of examples 57 or 58, wherein the motion of at least one of said at least two movable blades is linear.

EXAMPLE 60

The device of examples 57-59, wherein the motion of at least one of said at least two movable blades is circular.

EXAMPLE 61

The device of examples 58-60, wherein said movement of said transmission is adapted to provide to at least one of said at least two movables blade with a linear movement comprising impact force.

EXAMPLE 62

The device of examples 57-61, wherein said at least two movable blades comprise a retracted state where said at least two movable blades are not exposed thereby avoiding said at least two movable blades from cutting.

EXAMPLE 63

The device of examples 58-62, wherein said motion is characterized by a frequency from about 1 Hz to about 100 Hz.

EXAMPLE 64

The device of examples 57-63, wherein said at least two movable blade exit distally said distal end from about 0.15 mm to about 2 mm.

EXAMPLE 65

The device of examples 57-64, wherein the movement of said at least two movable blades is towards each therefore allowing cutting by shearing.

EXAMPLE 66

A lead extraction accessory, comprising:
a. a handle;
b. an elongated body having a first proximal end, a first distal end, and a first lumen extending from said first proximal end toward said first distal end, said lumen sized and shaped to fit over a cardiac lead extraction device;
c. said first distal end of said elongated body comprising an operational portion comprising having a second proximal end and a second distal end;
wherein said operational portion comprises a controllable bendable flexible portion.

An aspect of some embodiments of the current invention relates to a method/device/system for substantially separating between the linear/longitudinal pushing force being applied by the physician through a lead extraction catheter and the pushing force being applied to the tissue, the method comprises bringing a lead extraction catheter through a vessel into contact with the adhesion site, and activating the device such that the tip of the device locally and/or temporally generates the majority of the longitudinal/linear impact/force applied to the tissue, wherein the device is characterized by having a mechanism at the distal end (the "tip"/the "head") comprising a lumen with a radius of at least 2.5 mm for passage of the lead and further comprising one or more of the mechanisms: (i) a flexible component for transferring linear (longitudinal) force forward along the catheter to the distal tip to provide longitudinal impact to the target tissue; (ii) a mechanism (e.g. a spring) for storing and abruptly releasing of energy wherein the storing of energy is internally within the tip and the abrupt releasing of energy has part of the motion being accelerating internally within the tip (without direct friction with external tissue) and part of the motion being extending outside the device to generate substantially longitudinal impact on the target tissue; and (iii) a tip orientation control mechanism to steer the tip and forces/impact application toward the desired direction, with bending of at least 20 degrees with a radius or less than 4 cm while effectively transferring the forces through a flexible shaft towards the tissue and maintaining an open lumen of at least 2.5 mm for passage of the lead.

In some embodiments, the method/device/system, further comprising applying rotational motion to the target tissue. In some embodiments, the method/device/system, characterized by that it reduces the magnitude of pushing force required to penetrate and/or separate an adhesion site compared with the pushing force required when the device is not activated. In some embodiments, the method/device/system, being effective in penetrating adhesive tissue with pushing force being less than 800 gr. In some embodiments, the method/device/system, being effective in penetrating adhesive tissue with pushing force being less than 500 gr. In some embodiments, the method/device/system, being effective in penetrating adhesive tissue with pushing force being less than 300 gr. In some embodiments, the method/device/system, being effective in penetrating adhesive tissue with pushing force being less than 1300 gr.

In some embodiments, the method/device/system, characterized by that it reduces the magnitude of lead pulling force required to penetrate and/or separate an adhesion site compared with the lead pulling force required when the device is not activated. In some embodiments, the method/device/system, being effective in penetrating adhesive tissue with lead pulling force being less than 800 gr. In some embodiments, the method/device/system, being effective in penetrating adhesive tissue with lead pulling force being less than 500 gr. In some embodiments, the method/device/system, being effective in penetrating adhesive tissue with lead pulling force being less than 300 gr. In some embodiments, the method/device/system, being effective in penetrating adhesive tissue with pushing force being less than 1300 gr.

An aspect of some embodiments of the current invention relates to a lead extraction catheter comprising one or more mechanisms selected from a group consisting of: (i) a steerable sheath; (ii) a lead cutter; (iii) a lead bending and/or fixating mechanism for firmly holding the lead against the catheter to enable cutting of the lead by the catheter (iv) a mechanism for indicating catheter pushing force; (v) a catheter gripping handle with catheter pushing force sensor/evaluation/indication; (vi) a handle for gripping the one or more lead pulling wires and/or lead locking styletes; (vii) a handle for gripping the one or more lead pulling wires and/or lead locking styletes with lead pulling force sensor/evaluation/indication/control and/or limiter; and (viii) a mechanism for gripping the one or more lead pulling wires and/or lead locking stylete with lead pulling distance and/or velocity control and/or indicator and/or limiter. (ix) a mechanism (as part of the catheter or as an independent device) that can be pushed ahead of the catheter main body, capable of inflating a balloon inside the blood vessel, to form a firm resistance for the catheter to push against; (x) modularity of the system, where the device may be composed of two separable parts, for example a hand-held part and a pedal part, with the electronics and potentially also the motor are part of the pedal component; (xi) a mechanism for sensing the position of the lead inside the catheter, i.e. who well the lead is centered in the catheter, and an indicator reporting this information to the user by visual or audio signals.

In some embodiments, said lead extraction catheter incorporates/utilizes one or more of said mechanisms, and is characterized by that it reduces the magnitude of pushing force required to penetrate and/or separate an adhesion site compared with the pushing force required when the one or more mechanisms is not utilized. In some embodiments, said lead extraction catheter being effective in penetrating adhesive tissue with pushing force being less than 800 gr. In some embodiments, said lead extraction catheter being effective in penetrating adhesive tissue with pushing force being less than 500 gr. In some embodiments, said lead extraction catheter being effective in penetrating adhesive tissue with pushing force being less than 300 gr.

In some embodiments, said lead extraction catheter incorporates/utilizes one or more of said mechanisms, and is characterized by that it reduces the magnitude of lead pulling force required to penetrate and/or separate an adhesion site compared with the lead pulling force required when the one or more mechanisms is not utilized. In some embodiments, said lead extraction catheter, being effective in penetrating adhesive tissue with pushing force being less than 800 gr. In some embodiments, said lead extraction catheter, being effective in penetrating adhesive tissue with pushing force being less than 500 gr. In some embodiments, said lead extraction catheter, being effective in penetrating adhesive tissue with pushing force being less than 300 gr.

An aspect of some embodiments of the current invention relates to an add-on device being used to control and/or augment and/or modulate the function of a lead extraction catheter (e.g. either laser based and/or mechanical based and/or thermal based and/or ablation based and/or combination thereof), the add-on device comprises one or more of: (i) a steerable outer sheath; (ii) a lead cutter; (iii) a lead bending and/or fixating mechanism for firmly holding the lead against the catheter to enable cutting of the lead by the catheter (iv) a mechanism for indicating catheter pushing force; (v) a catheter gripping handle with catheter pushing force sensor/evaluation/indication; (vi) a handle for gripping the one or more lead pulling wires and/or lead locking styletes; (vii) a handle for gripping the one or more lead pulling wires and/or lead locking styletes with lead pulling force sensor/evaluation/indication/control and/or limiter; and (viii) a mechanism for gripping the one or more lead pulling wires and/or lead locking stylete with lead pulling distance and/or velocity control and/or indicator and/or limiter.

In some embodiments, said add-on device is coaxial with the lead extraction catheter. In some embodiments, said add-on device is mounted around the lead extraction catheter with an overlapping length of at least along majority of the length of the catheter. In some embodiments, said add-on device is mounted around the lead extraction catheter with an overlapping length of no more than a third of the length of the catheter. In some embodiments, said add-on device having a side opening for being mounted on the lead extraction catheter from the side of the catheter.

In some embodiments, said add-on device characterized by that it reduces the magnitude of pushing force required to penetrate and/or separate an adhesion site compared with the pushing force required when the add-on device is not utilized. In some embodiments, said add-on device, being effective in penetrating adhesive tissue with pushing force being less than 800 gr. In some embodiments, said add-on device, being effective in penetrating adhesive tissue with pushing force being less than 500 gr. In some embodiments, said add-on device, being effective in penetrating adhesive tissue with pushing force being less than 300 gr.

In some embodiments, said add-on device, characterized by that it reduces the magnitude of lead pulling force required to penetrate and/or separate an adhesion site compared with the lead pulling force required when the add-on device is not utilized. In some embodiments, said add-on device, being effective in penetrating adhesive tissue with lead pulling force being less than 800 gr.

In some embodiments, said add-on device, being effective in penetrating adhesive tissue with lead pulling force being less than 500 gr. In some embodiments, said add-on device, being effective in penetrating adhesive tissue with lead pulling force being less than 300 gr.

An aspect of some embodiments of the current invention relates to a lead extraction catheter comprising one or more of: (i) a sensor for tissue contact force; and (ii) a sensor for tissue classification.

An aspect of some embodiments of the current invention relates to an add-on device being used to control and/or augment and/or modulate the function of a lead extraction catheter (e.g. either laser based and/or mechanical based and/or thermal based and/or ablation based and/or combination thereof), the add-on device comprises one or more of: (i) a sensor for tissue contact force; and (ii) a sensor for tissue classification.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced. In the drawings:

FIGS. 11a-i are schematic views of exemplary tissue spreaders, according to some embodiments of the present invention;

CONTENTS

Figure 1A:
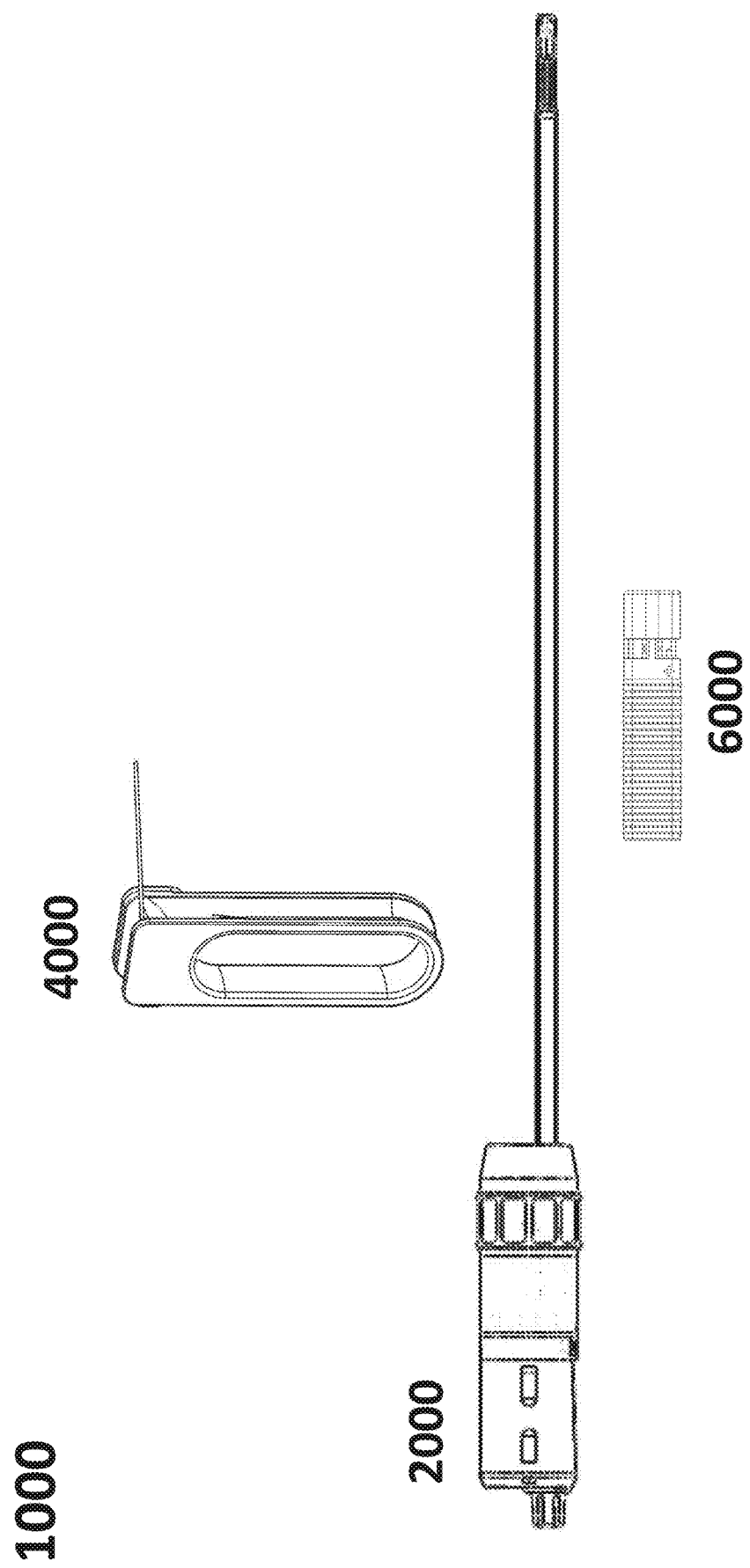
FIG. 1a is a schematic view of the kit, according to some embodiments of the present invention.

1. Overview
2. Exemplary lead extraction kit
3. Exemplary sheath
   3.1 Exemplary incorporated steering mechanism
   3.2 Exemplary reinforced central lumen 4. Exemplary distal head
   4.1 Exemplary steering tool of the distal head
      4.1.1 Exemplary inner bending shaft
   4.2 Exemplary tissue cutting tool
      4.2.1 Exemplary concentric rotating blades
      4.2.2 Exemplary circumferential rotating blades
      4.2.3 Exemplary impact tip
   4.3 Exemplary motion mechanisms
   4.4 Exemplary vibration of the distal head
   4.5 Exemplary eccentric rings
   4.6 Exemplary tissue spreaders
   4.7 Exemplary lead wire grasping
   4.8 Exemplary tissue and binding site assessment
   4.9 Exemplary IR Spectroscopic classification of matter distally to the device head
   4.10 Exemplary ultrasonic classification of matter distally to the device head
   4.11 Exemplary lead cutter
5. Exemplary general mechanisms/characteristics of the device
   5.1 Exemplary motion repetition
   5.2 Exemplary modifiable mechanical properties
   5.3 Exemplary combinatorial use of components/embodiments
   5.4 Exemplary characteristics of the pull-wires of the device
   5.5 Exemplary tension control and movement limiting mechanism
6. Exemplary characteristics of force measurements in the device
   6.1 Exemplary force transducer in the distal portion of the device
   6.2 Exemplary Model and Shape Based Force Estimation
   6.3 Exemplary opto-mechanical methods
      6.3.1 Exemplary optical methods based on reflective intensity of light
      6.3.2 Exemplary Fiber Bragg Grating methods based on wavelength shift
   6.4 Exemplary electro-mechanical methods
      6.4.1 Exemplary PVDF force sensing
      6.4.2 Exemplary capacitive-inductive force sensing
   6.5 Force analysis unit—Exemplary feature
   6.6 Lead centering detection unit
7. Handle of the device and motion
   7.1 Exemplary linear hammer motion of a LE device
   7.2 Exemplary dual motion cutting mechanism—rotating hammer
   7.3 Exemplary fluid dynamics and forces
8. Exemplary balloon embodiment
9. Additional information
10. Exemplary Pulling/Grapping device
11. Exemplary Pulling device
12. Exemplary Accessories
   12.1 Steerable sheath (for any LE device)
   12.2 Exemplary attachment ring for LE device
   12.3 Exemplary pulling/grapping accessory device
   12.4 Exemplary pulling device accessory
   12.5 Exemplary tissue and binding site assessment accessory
   12.6 Exemplary lead cutter accessory
13. Exemplary methods

DESCRIPTION OF SPECIFIC EMBODIMENTS OF THE INVENTION

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

1. Overview

An aspect of some embodiments of the present invention relates to reducing forces exerted on the leads, the veins, and/or heart tissue during a procedure for removal of cardiac leads from the body. In some embodiments, reduction of forces includes reducing pressure between a dilating tip of the device and the tissue while dilating the fibrous tissue encapsulating the lead. In some embodiments, a lead extraction device provides feedback about the pressure applied between the tip of the device and the tissue. In some embodiments, a deflectable sheath follows the bends of the lead within the veins while the lead is under reduced tension and/or while reducing a force applied to the sheath. In some embodiments, a lead extraction device provides controlled tension and/or limited pulling distance on the lead. In some embodiments, for example, limiting tension and/or pulling distance on the lead may prevent accidental pulling of the lead harder than and/or further than intended. In some embodiments, a lead extraction device provides feedback about the position and/or bending and/or the curvature of the tip of the device during the lead extraction procedure. In some embodiments, the device include ability to cut the lead itself so that the distal component of the lead may be abandoned in the body, while the proximal part is extracted without forcefully puling and tearing the lead.

In some embodiments, the lead extraction device separates the lead from the encapsulating fibrous tissue with reduced force exertion on the leads, veins, and/or heart tissue. In some embodiments, the device is easy to use, even for inexperienced users, which provide a potential advantage over similar prior art devices.

While some of the examples refer specifically to cardiac leads, cardiac lead extraction devices and methods, it is clear that the devices and methods disclosed herein are useful for extracting other leads in blood vessels (or other lumens) where the leads may stick. It should be also noted that the device can be mounted on anything embedded in the heart tissue (e.g. sensors) and remove them.

In the following disclosure the term "distal" refers to the general direction further from a user (e.g. a physician), while the term "proximal" refers to the general direction closer to the user; for example, something located distally may be in the body (e.g. towards the heart), and proximal may be, for example, outside the body or towards a handle, if any.

Some embodiments of the invention relate to an improved lead extraction device where the user may choose a suitable size of the device for the extraction. This means that a same or similar device design may be provided in a plurality of sizes (e.g. inner diameter (ID)). For example, a physician may choose the suitable ID according to the lead. In some embodiments, the minimum distance between the ID of the LE device and the OD of the lead is from about 0.2 mm to about 1.5 mm; optionally from about 0.5 mm to 1 mm; optionally from about 0.7 mm to about 0.9 mm. Alternatively, an operator may choose a suitable outer diameter (OD) and/or other physical attribute. For example, an ID may range between 2 mm to 8 mm, or optionally between 3 mm to 7 mm, or optionally, between 4 mm to 6 mm.

2. Exemplary Lead Extraction Kit

In some embodiments, the kit includes all necessary mechanisms and accessories needed in order to perform a safe and quick extraction of a cardiac lead while minimizing the chance of damaging the tissue surrounding the lead and minimizing the physical efforts required by the user to perform the extraction. In some embodiments, the kit comprises one device. In some embodiments, the kit comprises more than one device.

In some embodiments, the kit is an add-on/accessories kit for existing lead extraction devices. See below for further explanation on accessories. In some embodiments, the kit comprises one accessory. In some embodiments, the kit comprises more than one accessory.

In some embodiments, the lead extraction device comprises at least one of the following characteristics: highly maneuverability at the distal end of the lead extraction device (i.e.: steering mechanism); easy control of the different mechanisms of the lead extraction device at the proximal end of the lead extraction device; high precision of the mechanisms responsible of separating the lead from the surrounding tissue; effective lead cutting mechanisms; or any combination thereof.

2.1 Exemplary General Characteristics of a Lead Extraction Kit

In some embodiments, the mechanisms/tools/accessories described below are powered from outside the body. For example, they can be powered using manual or motorized means.

In some embodiments, the LE device includes one or more of the components/tools/accessories described below, as integral parts of the device. In some embodiments, the components/tools/accessories are independent parts that are adapted to be used as accessories to LE devices to enhance their capabilities (e.g. steerability, manipulation, etc.).

In some embodiments, the components described below are connected to at least one indicator located at the handle of the device and/or other device outside the body of the patient, which enables the user to be aware of actions related to the lead extraction procedure. In some embodiments, the indicator is a force indicator, which provides real-time information regarding the force applied when pushing/pulling. In some embodiments, the indicator is a meter, a screen showing colors, a sound, or any other suitable indicator device (e.g. to be shown on displays, on the device itself, etc.).

In some embodiments, the lead extraction (LE) device is steerable while maintaining the integrity of the LE device, which may allow it to sustain the high forces which may be required for the procedure, for example, as will be described below with regards of the structure of the device.

In some embodiments, the LE device may include one or more mechanisms to separate the surrounding tissue from the lead, for example blades and/or lasers and/or spreaders. In some embodiments, each mechanism is activated independently. In some embodiments, the mechanisms are activated in synchronization. In some embodiments, a pedal activates the mechanism.

In some embodiments, the LE steerable device is configured to align itself to the lead and this may decrease the force necessary for the extraction. In some embodiments, the LE steerable device is configured to align itself to the vein and this may avoid damaging the vein. In some embodiments, alignment is done through activation of a steering mechanism controlled by the user, bending a section of the device at a desired angle, as will be further described below. This is contrary to prior art LE devices, which are configured to align the lead and the vein to the LE device by use of force, therefore potentially damaging the vein and/or encouraging undesirable force application directions.

In some embodiments, the movement for the cutting tools is delivered by linear and\or circular (e.g.: HHS and/or multilumen) motion mechanism, driven from outside the body of the patient and transmitted to the distal end of the device. In some embodiments, movement generated outside the body is converted from linear to circular (or vice versa) at the distal end of the device. These mechanisms will be further explained below.

Figure 1B:
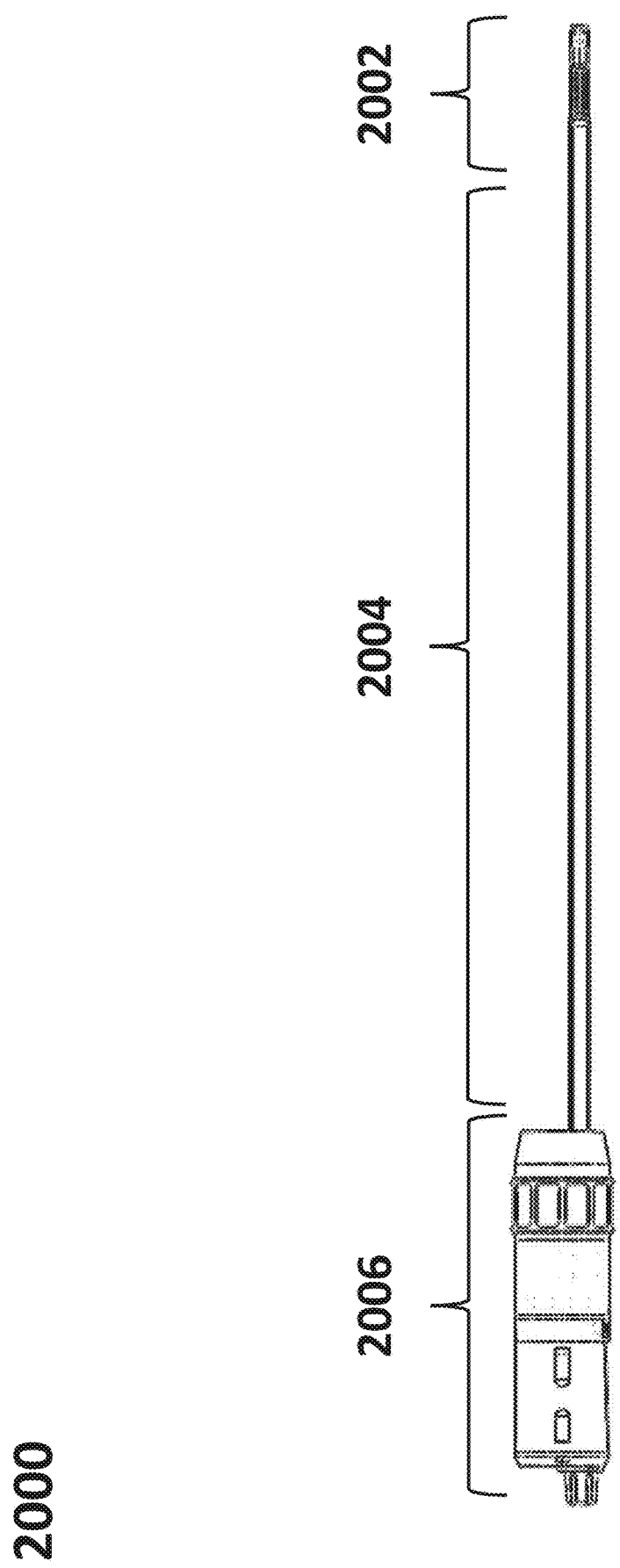
FIG. 1b is a schematic view of the lead extraction device, according to some embodiments of the present invention.

In some embodiments, the kit 1000 comprises a lead extraction device 2000, a sheath handle 4000 and a lead puller 6000, as shown for example in FIG. 1*a*. To facilitate the explanation of different embodiments of the invention, three general zones of the lead extraction device 2000 are identified: the distal head 2002, the sheath 2004 and the handle 2006, as shown for example in FIG. 1*b*.

Figure 2:
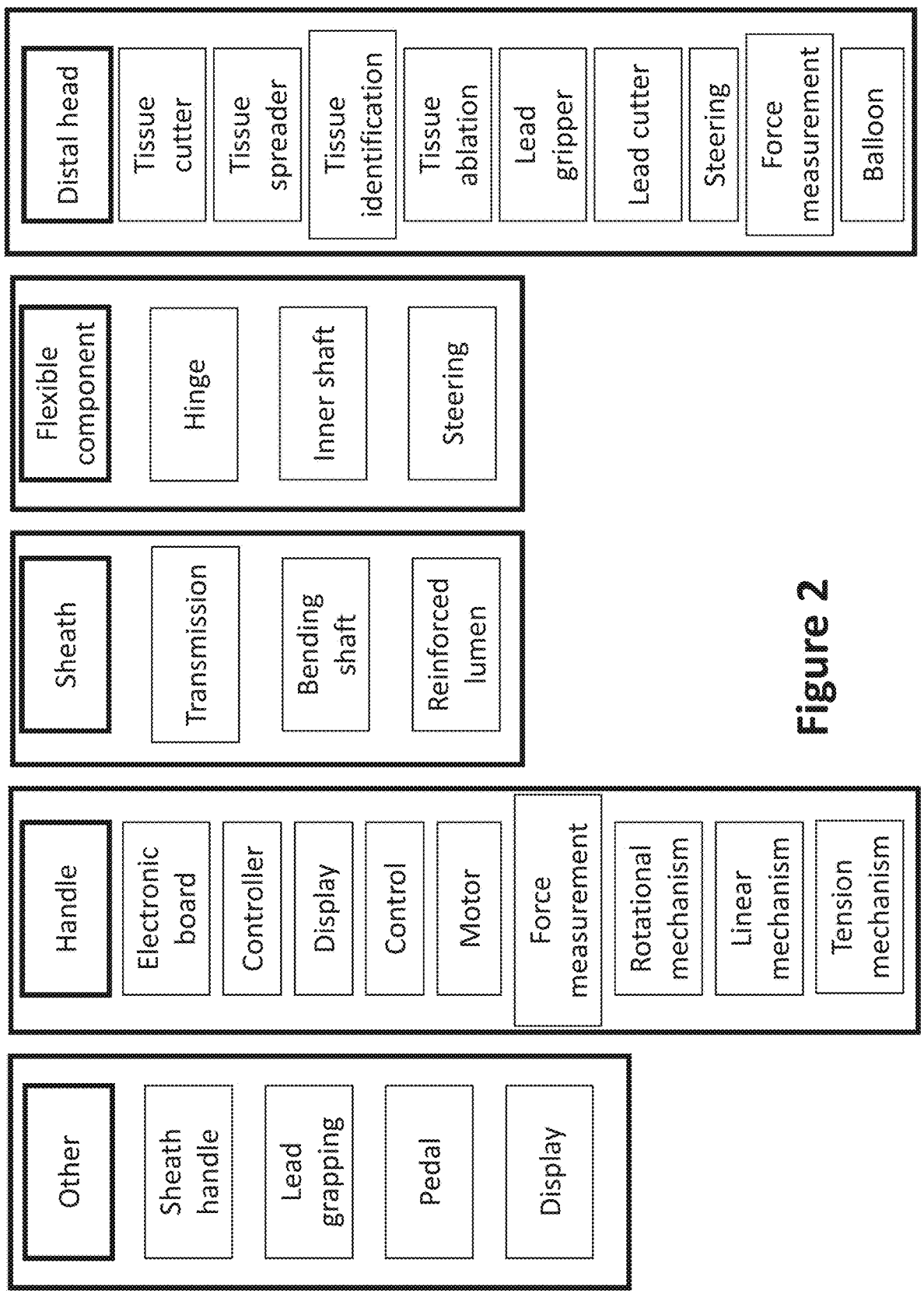
FIG. 2 is a schematic representation of exemplary components, exemplary tools and exemplary mechanisms according to their exemplary location on the device and/or outside the device, according to some embodiments of the present invention.

Referring now to FIG. 2, showing a schematic representation of exemplary components, exemplary tools and exemplary mechanisms according to their exemplary location on the device and/or outside the device.

In some embodiments, components at the distal head comprise at least one of the following: a tissue cutter tool, a tissue spreader tool, a tissue identification tool, a tissue ablation tool, a lead gripper tool, a lead cutter tool, a steering mechanism, a force measurement tool, a balloon device. In some embodiments, the tissue cutter tool removes tissue surrounding the lead. In some embodiments, a tissue spreader tool separates the tissue surrounding the lead. In some embodiments, the tissue identification tool identifies the tissue (e.g. blood, blood vessel, calcified tissue, etc.) and/or the lead located distally or adjacent to the distal head. In some embodiments, the tissue ablation tool removes tissue from the lead by erosive means (e.g. laser). In some embodiments, the lead gripper tool physically holds the lead allowing the user to pull the lead proximally. In some embodiments, the lead cutter tool cuts the lead at the user's desired location. In some embodiments, the steering mechanism specifically moves the distal head to any direction desired by the user. In some embodiments, the force measurement tool provides indication of the forces applied to the distal head. In some embodiments, the balloon device is used as a tissue separator. In some embodiments, the balloon device is used for isolating specific zones from the blood flow. In some embodiments, the balloon device is used as anchorage for the LE device.

In some embodiments, components of the flexible component comprise at least one of the following: at least one hinge, an inner shaft, a steering mechanism. In some embodiments, the at least one hinge enables the location where the at least one hinge is located to bend. In some embodiments, the inner shaft holds the forces of push/torque/rotation/speed rotating/hammering/bending radius of the flexible component. In some embodiments, the steering mechanism bends the flexible component to the desired direction.

In some embodiments, components of the sheath comprise at least one of the following: a transmission, a bending shaft, a reinforced lumen. In some embodiments, the transmission delivers the mechanical movements from the handle to the distal head and vice versa. In some embodiments, the bending shaft holds the sheath from being affected by high torque forces and from the activation of the transmission. In some embodiments, the reinforced lumen preserves preserve the cross section of the sheath.

In some embodiments, components of the handle comprise at least one of the following: at least one electronic board, at least one controller, at least one display, at least one control, at least one motor, a rotation mechanism, a linear mechanism, at least one force measurement tool and a tension tool. In some embodiments, the electronic board is responsible for receiving and delivering commands from the user to the different components in the handle. In some embodiments, the controller is responsible for activating the different components in the handle according to the commands received by the user through the electronic board. In some embodiments, the display provides visual information to the user regarding the different components of the device. In some embodiments, the control what the user presses and/or moves in order to actuate the components of the device. In some embodiments, the control is connected to the electronic board. In some embodiments, the control is connected directly to movement mechanism (e.g. motor, springs, rings). In some embodiments, the motor provides the necessary force to actuate the components of the device. In some embodiments, the rotation mechanism provides rotational movement to the components of the device. In some embodiments, the rotation mechanism receives the force from the motor. In some embodiments, the linear mechanism provides linear movement to the components of the device. In some embodiments, the linear mechanism receives the force from the motor. In some embodiments, linear movement is converted into circular movement at the handle. In some embodiments, circular movement is converted into linear movement at the handle. In some embodiments, linear movement is converted into circular movement at the distal head. In some embodiments, circular movement is converted into linear movement at the distal head. In some embodiments, the force measurement tool provides indication to the user on the forces applied on the handle (generally forces in the distal direction. In some embodiments, the tension tool keeps the tension on the lead at a fixed chosen level, for example by pulling the lead. In some embodiments, the tension tool releases the lead if the tension increases over the set parameter. In some embodiments, the tension tool pulls the lead if the tension decreases under the set parameter.

In some embodiments, components and/or elements reside outside the LE device. In some embodiments, external components and/or elements comprise at least one of the following: a sheath handle, a lead grapping tool, at least one pedal, at least one display. In some embodiments, the sheath handle allows the user to hold the sheath. In some embodiments, the lead grapping tool allows the user to pull and hold the lead not with his/hers own hand. In some embodiments, the at least one pedal is used to activate a component through the handle. In some embodiments, components can be activated at the handle. In some embodiments, components can be activated at the pedal. In some embodiments, components can be activated at the handle and at the pedal. In some embodiments, the display provides visual information to the user regarding the different components of the device.

3. Exemplary Sheath 2004

In some cases, the stiffness of a sheath may significantly cause complications in the lead extraction procedure. In some occasions, in order to induce the stiff sheath to bend and/or to follow the curved path of a lead through a vein, the lead may be pulled taut. In some cases, this tension in the lead may cause the lead to break resulting in a more complicated extraction procedure, or the tension in the lead may result in the lead tearing a vein and/or the heart's wall. For example, this may occur when the lead is attached to the vein and/or the heart wall by fibrous tissue. Such tearing may result in a serious bleeding complication. In other occasions, the stiffness of the sheath may contribute to complications as a result of the forces applied to the vein walls by the sheath after it has been bent. For example, when force is applied to the sheath in an attempt to move it forwards along the lead, the sheath may apply forces on the walls of the vein, for example at a bend. In some cases, a stiffer sheath may exert more force on the walls of the vein.

In some embodiments, the sheath and/or the distal head include a region which is significantly more flexible then other parts of the sheath. Optionally, the sheath and/or the distal head include multiple highly-flexible regions along their length. In some embodiments, these characteristics can provide one or more of the following potential advantages: reduced tension over the lead and/or the blood vessels; enhanced control of the LE device; easier extraction procedures for the user; and more. For example, the flexible region may support a bending radius (without kink, under a given force) 3 times smaller than the other parts support, for example 5 times smaller, for example 10 times smaller, for example 20 times smaller, or any ratio in between those mentioned. In some embodiments, the device comprises the flexible region and is adapted to withstand the internal forces from the actuation mechanisms occurring in the distal tip. In some embodiments, the distance between the flexible region and the location where the actuation in the distal tip occurs is from about 0 mm to about 15 mm; optionally from about 2 mm to about 10 mm; optionally from about 4 mm to about 8 mm.

3.1 Exemplary Incorporated Steering Mechanism

Figure 3A:
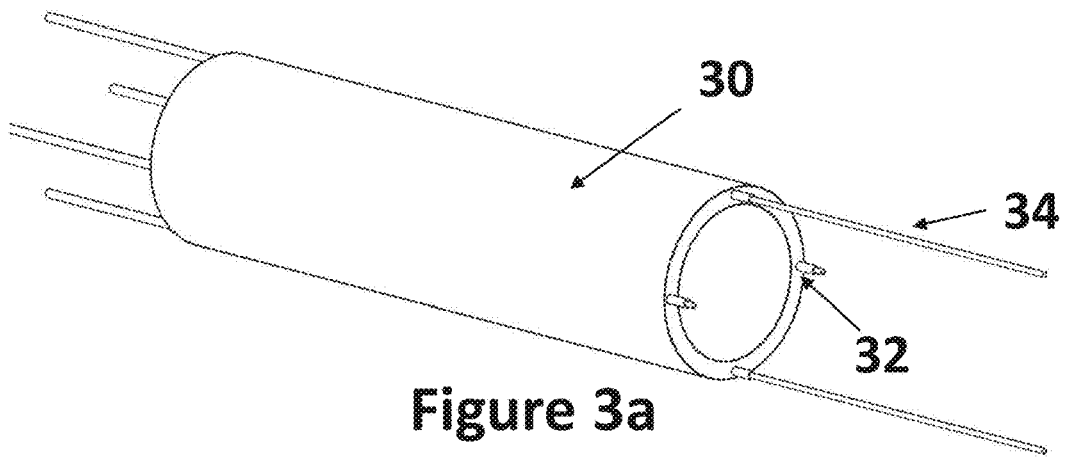
FIGS. 3a-e are schematic views of exemplary incorporated steering mechanisms, according to some embodiments of the present invention.

In some embodiments, the steering mechanism is incorporated in a dedicated sheath that covers the catheter, as shown for example in FIG. 3a. In some embodiments, the dedicated sheath comprises an outer envelope 30, at least one wire guide 32, and at least one wire 34. In some embodiments, the wire guide provides a suitable free path of actuation to the wire. In some embodiments, the wire guide enables the wires to move distally and proximally without affecting or causing distortions in the sheath. In some embodiments, the sheath is an integral part of the LE device. In some embodiments, the sheath is an add-on to an existing LE device (see accessories in section 12). In some embodiments, the steering mechanisms comprise one wire guides with one wire. In some embodiments, the steering mechanisms comprise two wire guides with two wires. In some embodiments, the steering mechanisms comprise three wire guides with three wires. In some embodiments, the steering mechanisms comprise four wire guides with four wires, as shown for example in FIG. 3a. In some embodiments, the number of wire guides/wires dictate the number of directions to which the steering mechanism can direct the distal end of the device.

Figure 3B:
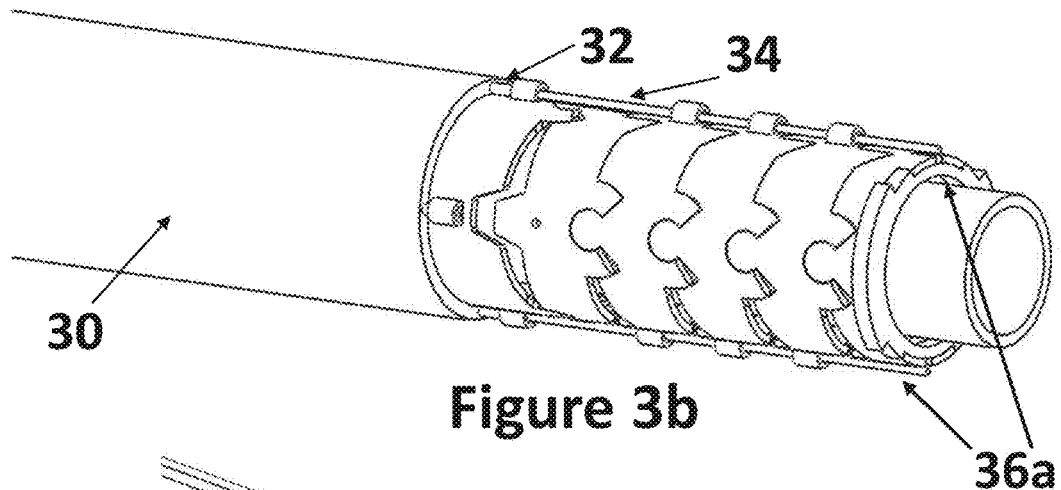
Figure 3C:
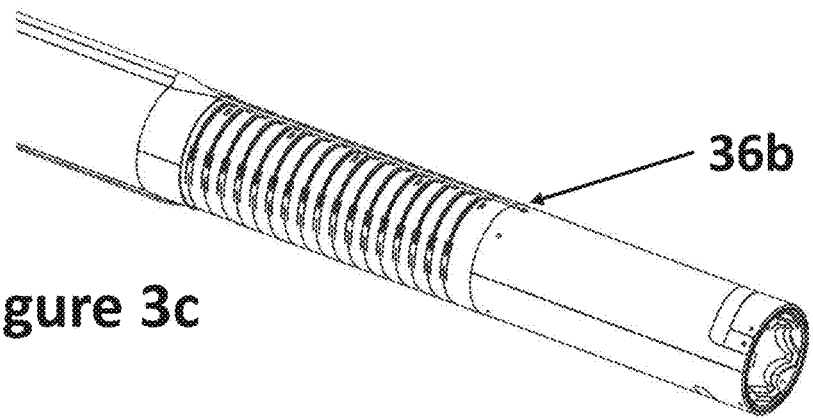

In some embodiments, the steering mechanism is connected to a hinge as shown, for example, in FIG. 3b. In some embodiments, the location where the steering mechanism meets the hinge and/or the distal head comprises a cap (36b), which protects the wire from disconnecting from the hinge and/or the distal head. In some embodiments, from the outer envelope 30, over the wire guides 32, the wires 34 are connected to dedicated slots 36a located on the hinges. In some embodiments, the wires 44 are connected to dedicated slots 36b on the distal head, as shown for example in FIG. 3c. In some embodiments, the position of the wires, either more distal or more proximal, provides the distal head with the variable mobility. In some embodiments, the user pulls or pushes the wires to control the movement of the distal head, as shown for example in FIG. 3d. In some embodiments, when the user pulls wire 34a, following arrow 38a while pushing wire 34b, following arrow 38b, it causes the distal head to bend as shown by arrow 38c.

Figure 3D:
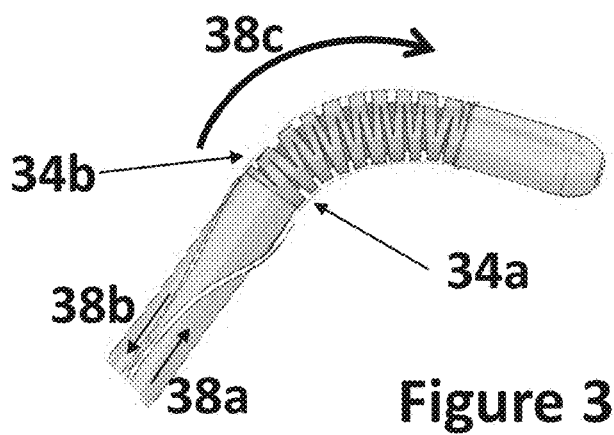

In some embodiments, the steering wire that runs from the handle 106 to the tip 102 runs outside and along the sheath 104, as shown for example in FIG. 3d.

In some embodiments, the steering wire that runs from the handle 106 to the tip 102 runs in a braided reinforced coil sleeve (extension coil with PTFE cover or a tube that is braided reinforced coil), for example: Vention Medical 142-0011 or 142-0008 or "Microlumen"—Pure PTFE ID with Braid—0.0005"×0.0025"@80 PIC. In some embodiments, the dimensions are: ID: 0.0104", OD: 0.0234", Wall: 0.0065". In some embodiments, the wire is inserted in a PTFE tube. In some embodiments, the braided reinforced coil sleeve is connected to the handle or/and to the hinge to maintain length of the wires that runs in it.

In some embodiments, the steering wires that run from the handle to the tip need to hold forces up to 8 kg at the maximus bending radius of the hinge. In some embodiments, the same forces are applied to the braid reinforced coil, for example: at 45 degrees, the force can be 400-700 g on free air; and at 100 degrees, the force can be 1100 g-1800 g. In some embodiments, these forces include the accumulated friction forces between the wire and the reinforced tube, along the full path to the handle.

Figure 3E:
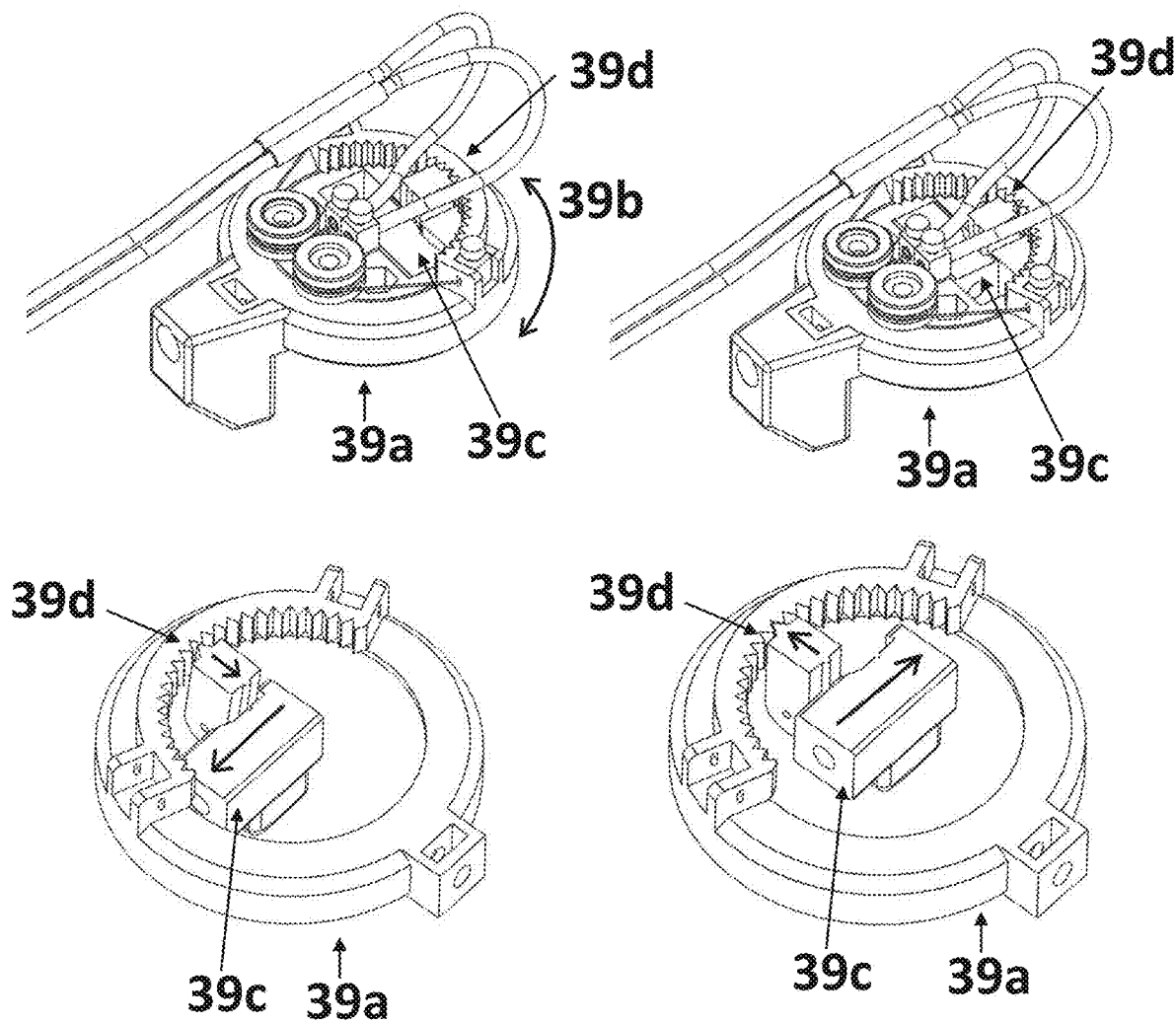

In some embodiments, the user sets the steering mechanism to bend the distal end at any angle or position, for example at 10 degrees, 0 degrees, 90 degrees, 30 degrees, etc. In some embodiments, the user can "lock" the position by activating a locking mechanism (example shown in FIG. 3e) on the handle and then the hinge will stay in this position due to the wires and the braid reinforced coil, which are holding the hinge at the chosen position. In some embodiments, a lever operates the locking mechanism. In some embodiments, a button operates the locking mechanism. In some embodiments, the steering mechanism is activated by a ring 39a around the handle that can be rotated 39b to control the degree of bending, and a lever 39c is pushed to engage a lock 39d, as shown for example in FIG. 3e. In some embodiments, the user works with the cutting blades at the chosen position. In some embodiments, the steering wires that run from the handle to the tip comprise a slack of the braided reinforced tube. In some embodiments, the slack is located at the handle. In some embodiments, the slack is located along the shaft under the outer cover of the shaft. In some embodiments, the length of the slack is from about 2 cm to about 7 cm; optionally from about 3 cm to about 6 cm; optionally from about 4 cm to about 5 cm. In some embodiments, there is minimum slack or no slack at all. In some embodiments, there is no braided reinforced tube.

3.2 Exemplary Reinforced Central Lumen

In some embodiments, a lumen of the flexible device shaft is reinforced. Optionally, the reinforcement is designed to preserve the cross section of the lumen. For example, a circular cross section of the inner lumen may be retained during bending. In some embodiments, maintaining the cross section of the lumen may reduce friction on the lead wire due to shaft bending. Optionally, the reinforcement may include a coil and/or a braid and/or a ring.

In some embodiments, the shaft is reinforced with one or more coils, braids, wires, or other components in order to achieve the desired combination of mechanical properties, for example, flexibility and pushability. In some embodiments, multiple reinforcements of the shaft provide the desired properties, which effectively transmit the distal force applied to the device handle outside the patient's body to a distal section located within the vasculature and/or the heart.

4. Exemplary Distal Head 102

In some embodiments, the distal head of the lead extraction device includes one or more assistive tools in the extraction procedure of the cardiac lead. As mentioned above, in some embodiments, one or more of the following tools are located in the distal head of the lead extraction device: a tissue cutter tool, a tissue spreader tool, a tissue identification tool, a tissue ablation tool, a lead gripper tool, a lead cutter tool, a steering mechanism, a force measurement tool, a balloon device.

In the following, some examples of each tool/mechanism will be described.

4.1 Exemplary Steering Tool of the Distal Head

As mentioned above, in some embodiments, the region configured for active deflection is located immediately proximal to a dilating tip portion of the sheath. In some embodiments, this configuration allows the user to actively direct the distal head of the lead extraction device towards the desired direction.

Figure 4A:
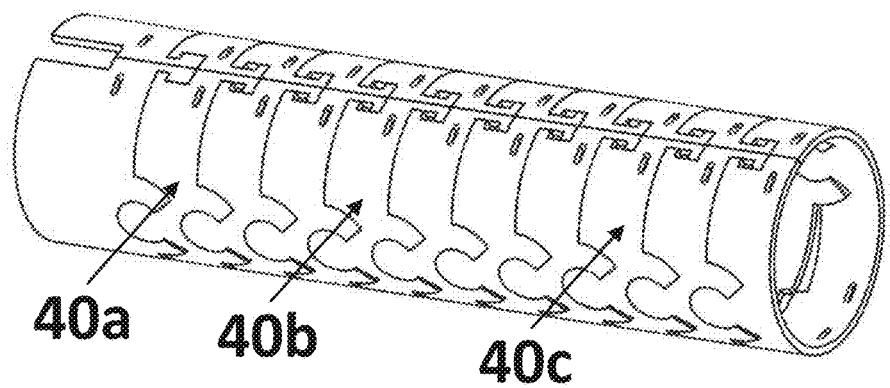
FIGS. 4a-h are schematic views of exemplary embodiments of some components in the flexible region, according to some embodiments of the present invention.

In some embodiments, a region proximal to the distal head includes a region which is significantly more flexible then other parts of the distal head and the sheath. Optionally, this region includes multiple highly-flexible regions along its length. These regions optionally include a hinge or multiple hinges (40a-c), for example as illustrated in FIG. 4a (showing multiple hinges).

Figure 4B:
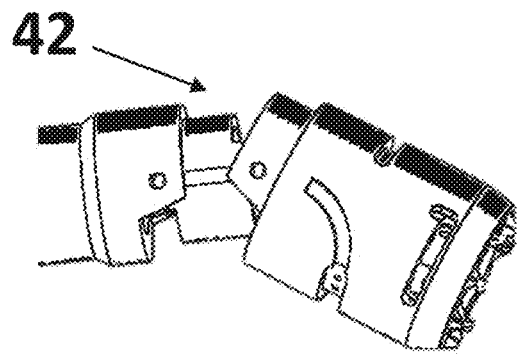

Alternatively, or additionally the distal head at these locations is constructed differently and/or constructed of different material. For example, such highly-flexible region may be located immediately proximal to the dilating tip portion of the sheath, as shown for example in FIG. 4b (showing a single hinge—42).

In some embodiments, the stiffness of a region of the distal head is actively controlled during use. For example, there may be a tension wire 34 which is configured to deflect the flexible region when the wire 34 is pulled and/or there may be a tension wire which is configured to straighten the flexible region when the wire 34 is pulled, as shown, for example, in FIGS. 3b and 3d, above. In some embodiments, the tension is adjusted by the user from the controls in the handle. In some embodiments, the tension is locked by the user allowing the distal head to remain at the selected level of tension. In some embodiments, the tension is locked using the mechanism as explained above and in FIG. 3e.

In some embodiments, active and/or passive deflection of the shaft and/or the tip of the sheath enables it to follow the curved path of the lead with reduced tension on the lead and/or less force on the sheath.

In some embodiments, the structure of the distal head of the lead extraction device is adapted to allow movement and steerability to the lead extraction device in order to enable directing the device in the right direction, especially at difficult points along the vessel where sharp turns are required.

In some embodiments, the steering mechanism is composed of multiple hinges interconnected to each other which enable the movement of the distal head to at least one direction. In some embodiments, the hinges enable the movement of the distal head to at least two directions. In some embodiments, the hinges enable the movement of the distal end to at least three directions. In some embodiments, the hinges enable the movement of the distal end to at least four directions. In some embodiments, the hinges enable the movement of the distal head to any direction. It should be noted that, in some cases, the less directions comprise the distal head, the more torque the distal head can withstand.

In some embodiments, the hinge has a wall thickness of 0.2 mm, 0.3 mm, 0.35 mm, 0.4 mm, 0.45 mm or 0.5 mm, and optionally from about 0.1 mm to about 1 mm; optionally from about 0.2 mm to about 0.8 mm; optionally from about 0.4 mm to about 0.6 mm.

Figure 4C:
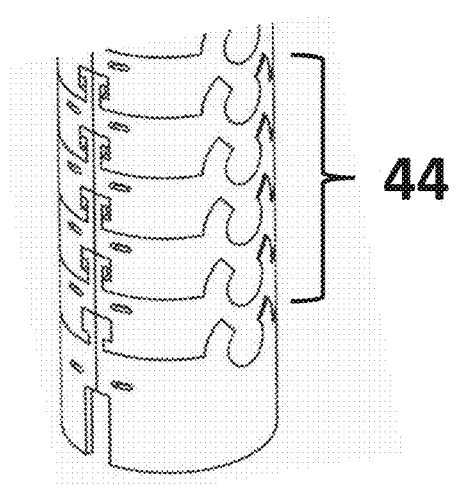
Figure 4D:
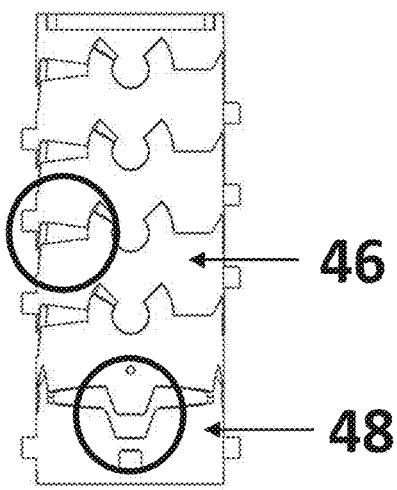

In some embodiments, the hinge is made of one cut (e.g.: laser cut) piece thereby creating in-body links. In some embodiments, the hinges are made of separate links attached and interlocked together. In some embodiments, the hinges are interlocked in the same direction 44, as shown for example in FIG. 4c. In some embodiments, the hinges are interlocked in different and/or alternate directions (46 and 48—circles), as shown for example in FIG. 4d.

Figure 4E:
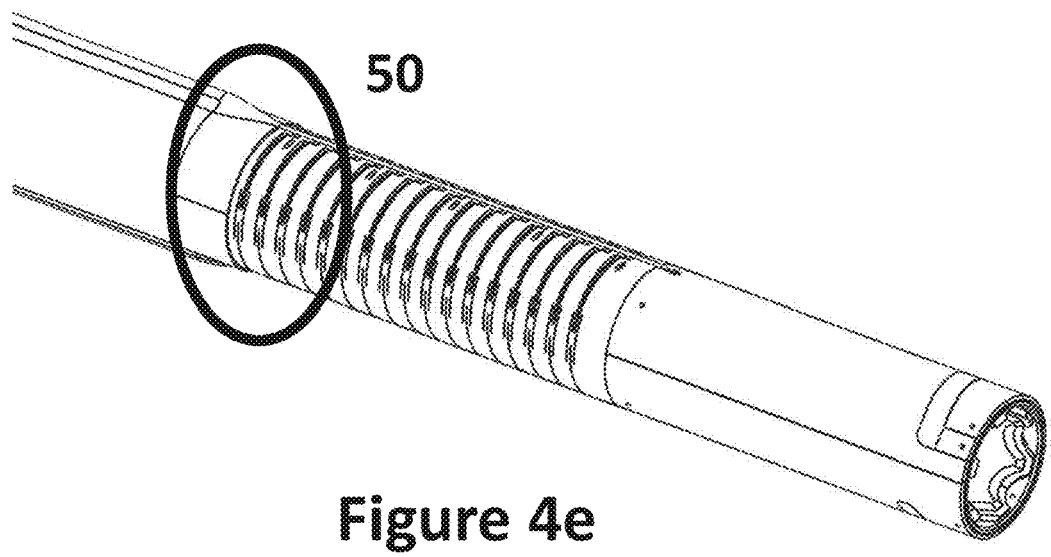

In some embodiments, a hinge is connected 50 to the outer sheath and works as "counter-force" for the bending of the distal end, as shown for example in FIG. 4e, circled part. In some embodiments, there is an inner layer 52 that rotates and\or makes the linear movement inside the sheath. In some embodiments, this inner layer has a smaller internal diameter than the outer sheath. In some embodiments, an internal layer that rotates and\or moves linearly under the hinge, is called "inner shaft" 54, as shown for example in FIG. 4f, circled part and FIG. 4g. In some embodiments, the bending shaft is part of the inner shaft and in other option it can be a separate part that is connected to the rotating\hammering inner shaft (see further explanations in section 4.1.1). In some embodiments, the inner shaft holds the forces of push/torque/rotation/speed rotating/hammering/bending radius etc. In some embodiments, the inner shaft is smooth to reduce friction with the outer layer and the inner layer. In some embodiments, the inner bending shaft has no inner layer and in has minimum openings 56 and small dimensions for each opening to reduce friction with the lead/tissue that moves inside the device. In some embodiments, the inner shaft is made of stainless steel. Optionally, the inner shaft is a spring or multilumen. In some embodiments, the inner shaft is covered by a thin elastomer material, which makes the inner shaft waterproof while maintaining flexibility and reduces friction with the other parts or reinforced coil or braided wire structure or side wire to transfer torque.

In some embodiments, the hinge is characterized by an outer diameter equal or less than the diameter of the sheath. In some embodiments, the length of the hinge is from about 6 mm to about 50 mm; optionally from about 10 mm to about 40 mm; optionally from about 20 mm to about 30 mm. In some embodiments, the hinge is characterized by a movement from 0 degrees (in the general orientation of the LE device) to about 180 degrees (in the opposite general orientation of the LE device), and in some options the hinge is characterized by a movement and bending only to one direction. In some embodiments, the minimum bending radius of the hinge is from about 2 mm to about 15 mm, optionally from about 4 mm to about 10 mm, optionally from about 6 mm to about 8 mm. In some embodiments, the side movement radius of the hinge is from about 5 degrees to about 100 degrees; optionally from about 10 degrees to about 60 degrees; optionally from about 20 degrees to about 40 degrees.

In some embodiments, the minimum force required to bend the hinge is almost 0 g, since the hinge comprises a structure of multi hinges, as shown for example in FIGS. 4a,c,d,h. In some embodiments, the hinge is a tube that is cut to have a flexible structure, as shown for example in FIG. 4h. In some embodiments, the minimum force required to bend the hinge is from about 50 g to about 300 g; optionally, from about 100 g to about 250 g; optionally from about 150 g to about 200 g, to arrive at the maximum bending hinge radius. In some embodiments, the hinge have 0% change in length or 1% or 3% change in length, and this almost lack of length does not affect the efficiency of the tissue cutting tool, which, in some embodiments, requires acceleration of the cutting part for a successful impact and cutting of the tissue and/or calcified tissue and/or plaque.

In some embodiments, while the hinge mainly bends to one direction, the inner (named "inner hinge" or "bending shaft" or "tongue hinge shaft") part of the hinge is able to rotate and expand. In some embodiments, the inner part is flexible and adapted to bend in all directions fast enough and with minimum required force while the flexible hinged part is bent. This enables the activation of the internal mechanisms while keeping to the minimum the general effects on the hinge that surrounds it. In some embodiments, the inner part is made of a cut stainless steel tube, which is flexible, as shown for example in FIG. 4g. In some embodiments, the inner part is made from a spring or from a braided polymer tube. In some embodiments, the length of bending shaft is similar to the hinge length and, in some embodiments, it can be shorter or longer to improve the radius of action of the hinge.

In some embodiments, the bending shaft supports a bending radius of, for example, 2-10 cm, for example 3-5 cm, for example less than 4 cm. At this bending radius, the lumen is still open and not collapsed or kinked, so that the lead inside it can move freely.

In some embodiments, the bending shaft comprises a small gap located between the outer-diameter (OD) of the inner shaft and the inner-diameter (ID) of the flexible hinged part that surrounds it. In some embodiments, this gap helps to protect the structure of the bending shaft from having a deformation at high torque forces, for example at forces between about 2N and about 20N; optionally between about 5N and about 15N; optionally between about 7N and about 10N; optionally the forces are at 5N, 7N, 8N, 10N, 12N, 15N or 20N. In some embodiments, the gap is from about 0.1 mm and about 0.4 mm; optionally from about 0.17 mm and about 0.3 mm; optionally from about 0.2 mm and about 0.25 mm; optionally the gap is 0.1 mm, 0.17 mm, 0.2 mm, 0.25 mm, 0.3 mm or 0.4 mm. In some embodiments, the bending shaft is flexible and adapted to bend in all directions. In some embodiments, the bending shaft's structure is strong and adapted to hold high torque forces. In some embodiments, the ID of the bending shaft is similar to the ID of the inner shaft connected to distally to it, as shown for example in FIGS. 4f and 15b. In some embodiments, the ID of the bending shaft can be up to 1.5 mm bigger or 1.5 mm smaller from the ID of the inner shaft. In some embodiments, the lead runs through the bending shaft, so the structure and manufacturing include elements to reduce unwanted wear or damage on the lead like, for example, electro-polish after cutting the tube to lower the gaps from one strata to another. In some embodiments, the internal structure of the LE device is designed to decrease friction between the lead and the internal structure of the device. In some embodiments, this reduces the necessary force required by the user to extract the lead from the body.

In some embodiments, the bending shaft comprises another internal layer to reduce and/or avoid unwanted wear or damage or friction of small pieces due to the rotation of the parts.

In some embodiments, the bending shaft has a wall thickness of 0.2 mm, 0.3 mm, 0.35 mm, 0.4 mm or 0.45 mm. Optionally from about 0.2 mm to about 0.5 mm; optionally from about 0.3 mm to about 0.45 mm; optionally from about 0.35 mm to about 0.4 mm.

In some embodiments, the lead extraction device provides feedback to the user about the position or/and bending or/and the deflection or/and the curve of the shaft and/or the tip. In some embodiments, the deflection may be used to estimate the pressure of the tip on the tissue.

4.1.1 Exemplary Inner Bending Shaft

Figure 4F:
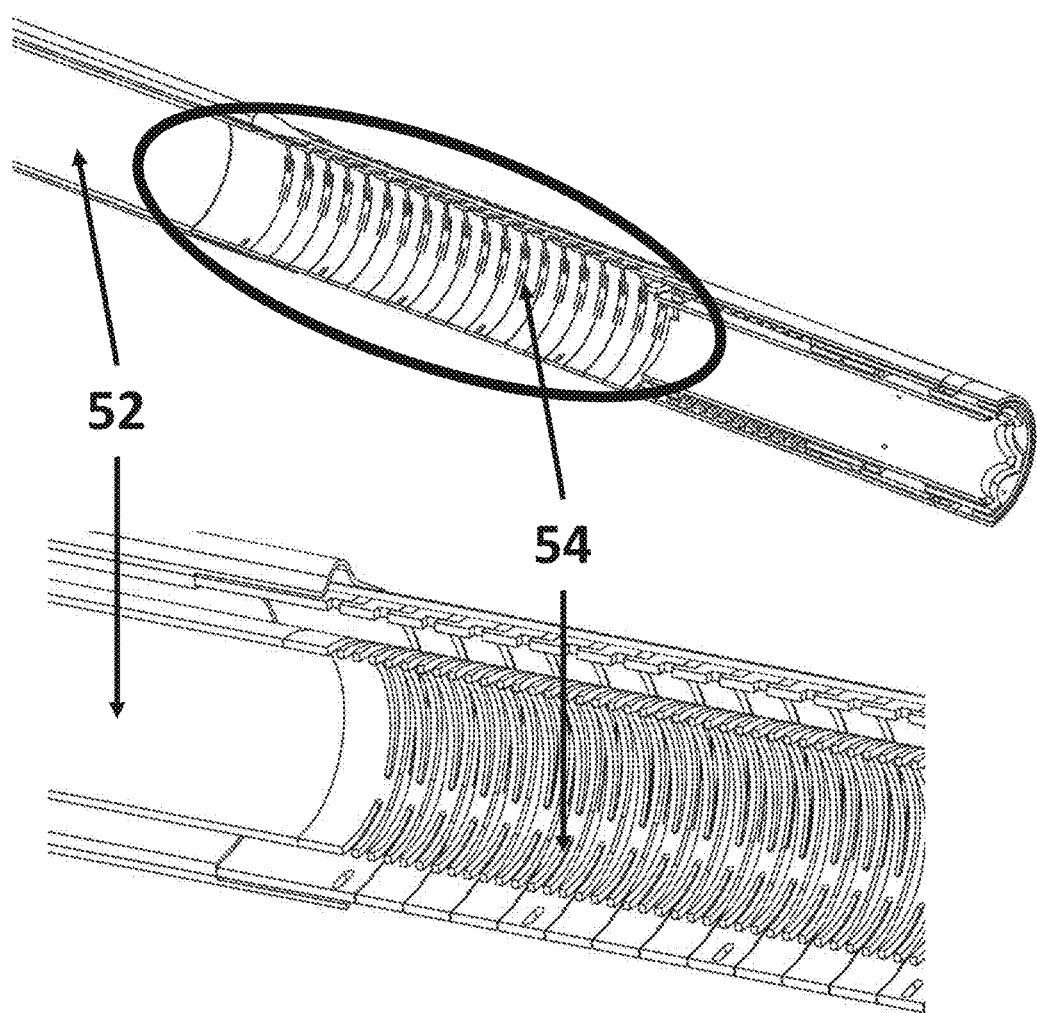
Figure 4G:
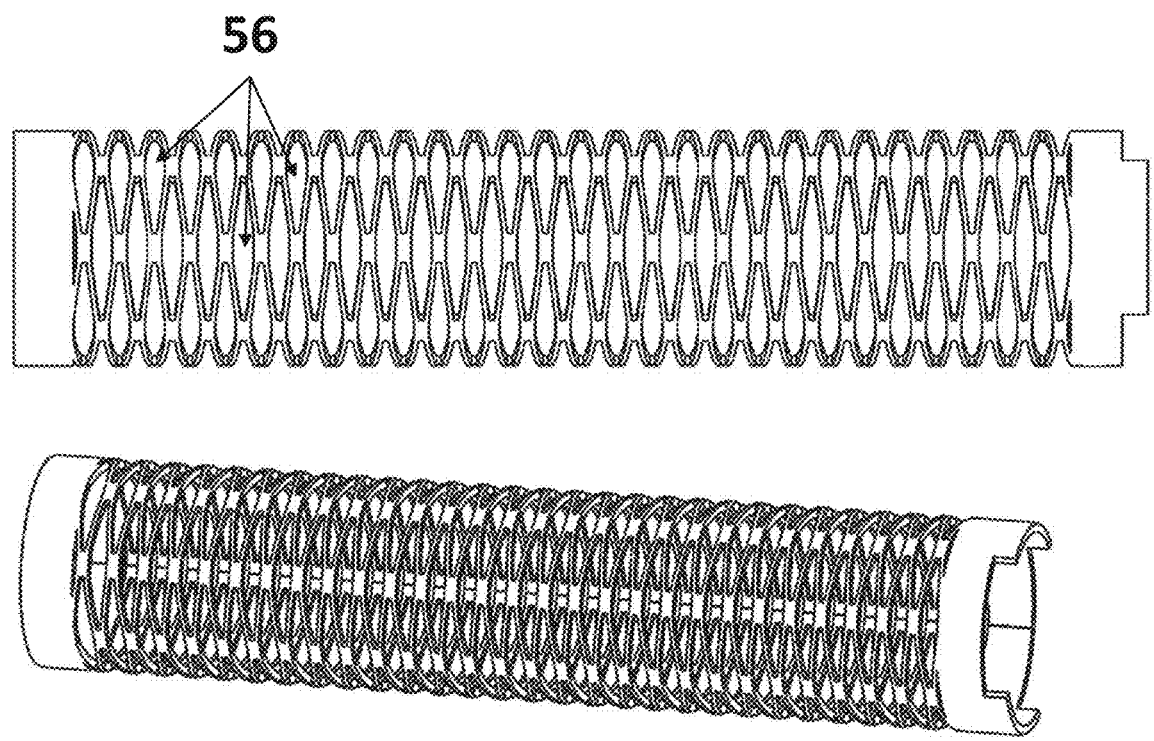
Figure 4H:
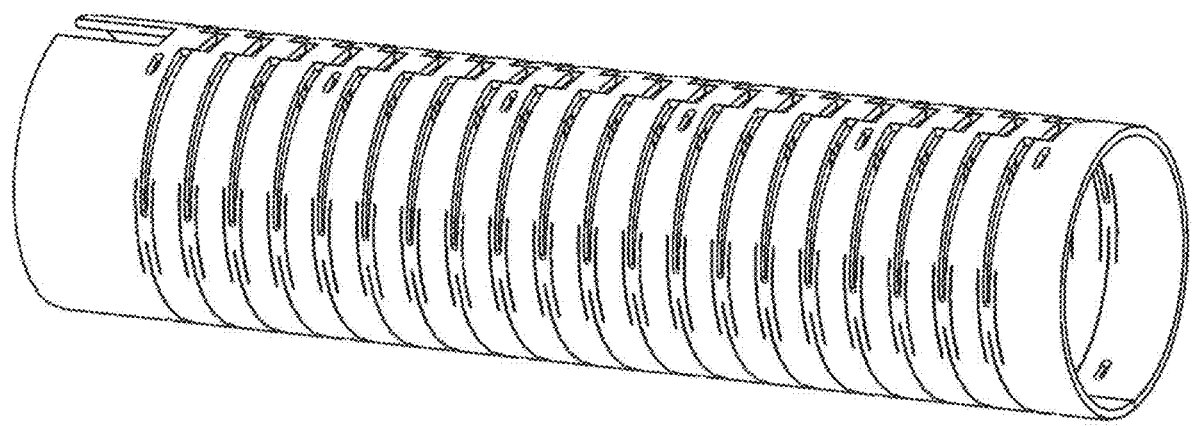

In some embodiments, an inner bending shaft is as disclosed, for example in FIGS. 4*f-g*. In some embodiments, the inner bending shaft is located inside the sheath as shown, for example in FIG. 4*f*. FIG. 4*g* shows a schematic representation of the inner bending shaft. In some embodiments, the length of an inner bending shaft is, for example, from about 15 mm to about 55 mm, for example 15 mm, 25 mm or 35 mm. In some embodiments, the inner bending shaft is as long as the catheter. In some embodiments, the external diameter of an inner bending shaft is, for example, from about 3 mm to about 10 mm, for example 4-6 mm, 4 mm or 5 mm. In some embodiments, the thickness of the strati of an inner bending shaft is, for example, from about 0.1 mm to about 0.45 mm, for example 0.15 mm, 0.21 mm or 0.25 mm.

In some embodiments, the inner bending shaft is located between the distal end of the sheath and the proximal end of the distal head, inside the flexible hinged portion. In some embodiments, the inner bending shaft is interconnected, on its proximal end, to a transmission that runs inside the sheath and connected to, for example, a motor in the handle of the device; and on its distal end to an operational tool located at the distal head of the device.

4.2 Exemplary Tissue Cutting Tool

As explained above, in some cases, fibrous tissue surrounds parts of the lead. This can cause difficulty in the lead extraction procedure. In some embodiments, the distal head comprises a tissue cutting tool adapted to cut the tissue surrounding the lead. In some embodiments, blades located at the distal end of the device are used as cutting tools. In some embodiments, the cutting action is linear (or axial), which means cutting the tissue when moving blades back and forth (proximally and distally). In some embodiments, the cutting action is rotational (or circumferential), which means that the blades rotate clockwise (CW) and/or counterclockwise (CCW) with one set of blades and/or by rotating one set of blades against another to shear tissue between them. In some embodiments, the cutting action is a combination of linear (or axial) and rotational (or circumferential). In some embodiments, the tissue cutting tool comprises a protective cover, which protects from unwanted damage of the vessel walls. In some embodiments, the combination of two blades provides that one of the blades holds the tissue while the other cuts, which may prevent torque-induced damage to the vessel walls.

4.2.1 Exemplary Concentric Rotating Blades

Figure 5A:
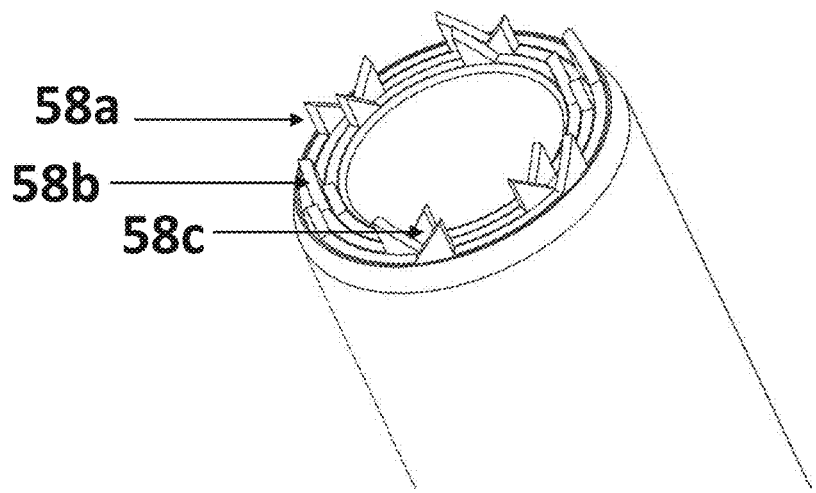
FIGS. 5a-f are schematic views of exemplary embodiments of some operational components located at the distal head, according to some embodiments of the present invention.

In some embodiments, the distal end comprises a mechanical tip and/or rotating blades. In some embodiments, the rotating blades include, for example, two or more concentric tubes which rotate relative to each other. Optionally, the concentric tubes have blades protruding from their distal ends, for example as illustrated in FIG. 5*a*. In this example, the concentric rotating blade tip comprises three concentric tubes with blades 58*a-c*. In some embodiments, the middle-bladed tube 58*b* optionally rotates with respect to the other two tubes. In some embodiments, relative rotation of the tubes optionally provides tissue disruption and/or facilitates the penetration of the tip into the fibrous tissue. Alternatively, or additionally, the tubes are not concentric. Alternatively, or additionally, the movement of the tips is non-continuous (for example a vibration and/or shaking). In some embodiments, the cutting action is rotational, which means that the blades rotate CW and/or CCW with one set of blades or by rotating one set of blades against another to shear tissue between them. In some embodiments, rotating one set of blades against another to shear may be an effective tool for cutting the lead, if necessary.

Figures 5B, 5C:
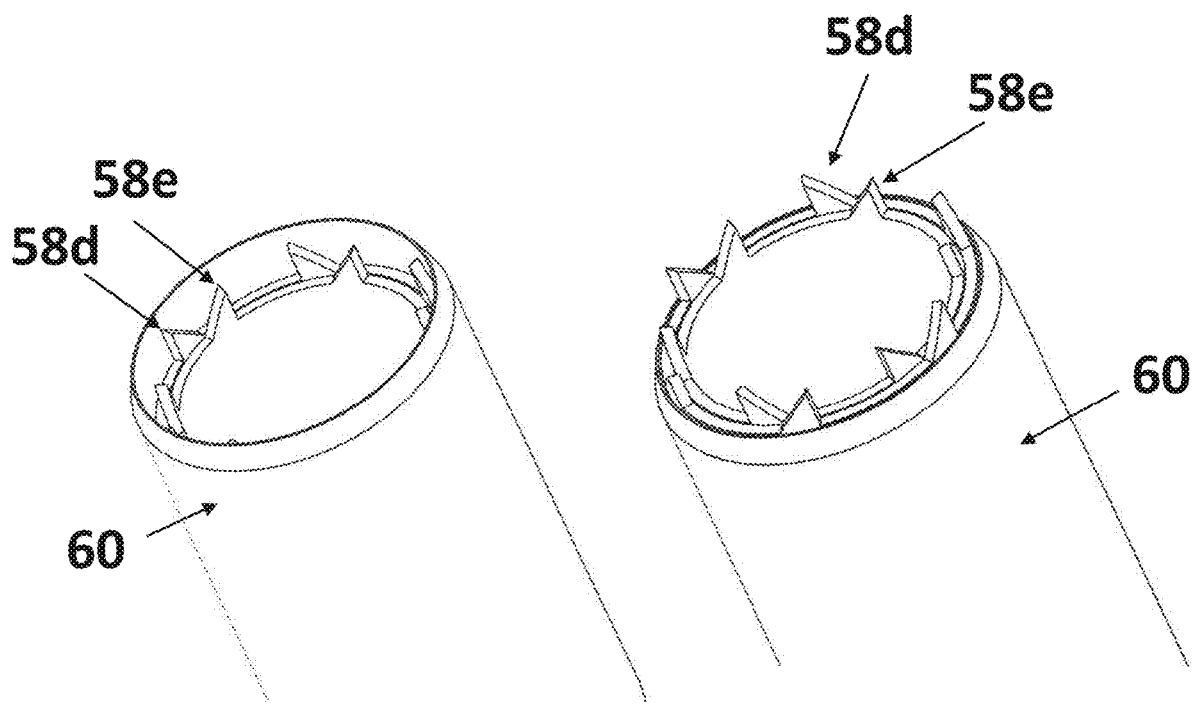

In some embodiments, the tissue cutting tool includes a protective tube. In some embodiments, the protective tube is without blades. In some embodiments, the protective tube is located inside a cutting tube and/or inside a set of concentric cutting tubes. In some embodiments, the protective tube shields and/or protects the lead from the blades by physically separating between the two. Alternatively, or additionally, there is a protective tube outside the cutting tubes. In some embodiments, the protective tube shields and/or protects surrounding tissue from the blades of the cutting tubes by physically separating the blades from the surrounding tissue. In some embodiments, surrounding tissue includes walls of veins and/or the heart. An exemplary embodiment of tip having an outer protective tube is illustrated, for example, in FIGS. 5*b-c*. In this example, a concentric rotating blade tip with two concentric bladed tubes and a non-bladed outer tube is shown. In some embodiments, for example, the outer tube shields surrounding tissue from the blades. In some embodiments, the blades move longitudinally relative to the outer shield. In some embodiments, the blades move distally in order to engage the fibrous tissue. In some embodiments, at the discretion of the user, the blades are extended distally and/or rotated when aggressive tissue cutting is necessary. In some embodiments, the protective tube is deployable when the blades are active. In some embodiments, the protective tube is deployable when the blades are not active.

In some embodiments, after the cutting tube moves distally, it rotates to apply a shearing momentum on the target. In some embodiments, the rotation after the cut completes the action of cutting. In the exemplary embodiment shown in FIG. 5*b*, the blades of a cutting tube 58*d-e* are shown covered by the outer tube 60 and do not extend beyond a distal surface of the outer tube. In some embodiments, covering the blades avoids damage to tissue and/or other leads, for example when the sheath is moved. In some embodiments, the rotation of blades occurs only when the blades are extended beyond the outer tube, as shown for example in FIG. 5*c*. Alternatively, or additionally, blades rotate while within the outer tube. In some embodiments, rotating the blades while within the outer tube will free the device of tissue and/or material that is confined and/or lodged within the tube.

In some embodiments, the protective tube is deployed or retracted by the user, from the handle of the device. In some embodiments, the deployment mechanism runs from the handle to the distal end together with the motion mechanisms.

In some embodiments, the shape of the blades comprises a slope that helps in the cutting and in separating the lead from the tissue and/or from the vein. In some embodiments, the shape of the blades with the slope also avoids unwanted cutting of either the lead or surrounding tissue. In some embodiments, the blades comprise a triangular shape 62, as shown for example in FIG. 5*d*. In some embodiments, the blades comprise a scalloped shape with slope, as shown for example in FIG. 24*f*. In some embodiments, the blades comprise a scalloped shape with a slope inwards for the inner blade and with a slope outward for the outer blade. In some embodiments, the blades comprise a scalloped shape with a slope outward for the inner blade and with a slope inwards for the outer blade.

In some embodiments, the length of the blades is less than 2 mm, optionally in the range between about 0.1 mm to about 1.9 mm; optionally from about 0.2 mm to about 1.5 mm; optionally from about 0.5 to about 1.0 mm. Alternatively or additionally, a single tube and/or concentric tubes include blades of different lengths. In some embodiments, a single tube and/or concentric tubes include a number of blades from about 1 to about 50; optionally from about 4 to about 30; optionally from about 10 to about 20.

In some embodiments, two concentric tubes with blades at their distal ends have different configurations. For example, in a first configuration the tubes rotate together in the same direction. In some embodiments, this configuration is used for less aggressive cutting and/or to gently dilate the fibrous tissue around the lead. In another example, in a second configuration, the tubes rotate relative to each other. In some embodiments, this second configuration is used for more aggressive cutting of the tissue.

In some embodiments, two tubes rotate relative to each other by both tubes rotating. Alternatively, only one tube rotates. In some embodiments, a selection mechanism is supplied to enable a user to select one or a combination of various modes of blades motion. For example, modes of blade motion include one set of blades moving relative to a static (e.g. non-rotating) set of blades and/or one set of blades moving relative to one another set of moving blades and/or multiple sets of blades move together. Optionally, the various modes enable selection between more or less aggressive modes of cutting In some embodiments, the rotational movement of the blades is provided by a motor located at the handle of the device or proximally to the user. In some embodiments, a transmission is connected to the motor, on one side, and to the rotating tubes on the other. In some embodiments, the user controls the action of the motor and thereby the action of the rotating tubes.

4.2.2 Exemplary Circumferential Rotating Blades

In some embodiments, a plurality of independent rotating blades are arranged circumferentially around a central lumen 64. Optionally, the blades are located at the tip of the LE device, as shown for example in FIGS. 5e-f. In some embodiments, the rotating blades are sharp. For example, the blades may be configured to cut the tissue. Alternatively, or additionally there are blades that are configured to spread the tissue. Optionally, the blades are relatively blunt.

Figure 5D:
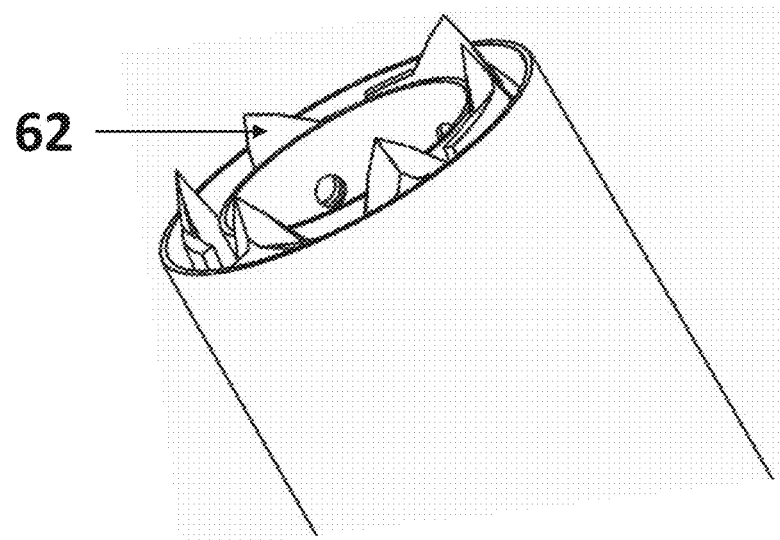
Figure 5E:
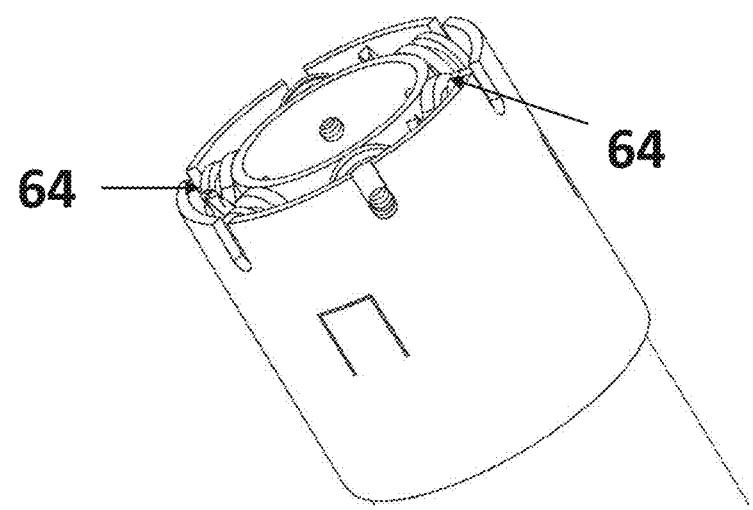
Figure 5F:
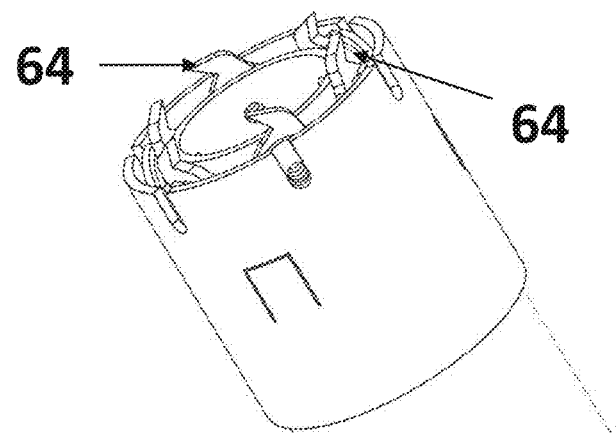

In some embodiments, rotating blades rotate continuously in one direction. Alternatively, or additionally a blade rotates a partial rotation and/or oscillate back and forth. Optionally, multiple rotating blades rotate altogether in the same direction. Alternatively, or additionally, some blades rotate clockwise while others rotate counter-clockwise. For example, alternating blades rotate in opposite directions. In some embodiments, some blades rotate clockwise or counter-clockwise for 360 degrees or 400 degrees or 500 degrees or 720 degrees or few turns in one direction and then to the other direction. In some embodiments, some blades rotate clockwise or counter-clockwise from about 15 degrees to about 1800 degrees; optionally from about 90 degrees to about 900 degrees; optionally from about 180 degrees to about 720 degrees. Alternatively, or additionally, some blades rotate clockwise or counter-clockwise and when the user turns off the rotation, the blades will turn the other way for about 360 degrees to about 720 degrees; optionally for about 90 degrees to about 180 degrees; optionally for about 120 degrees to about 160 degrees, to pull-in the blades into the protective cover. In some embodiments, the cover will move forward to protect and cover the blades and prevent an injury of the vein or lead or other. Optionally, the rotation of blades in opposing directions is balanced to avoid twisting of the distal end of the device. For example, the balance results in a very small and/or negligible net rotational force on the tissue and/or the sheath. Additionally, or alternatively, each blade acts as a tissue anchor for another blade (not in the triangular blade embodiment), for example for the blade adjacent to it. In some embodiments, balancing rotation of different blades facilitates increased tissue spreading and/or cutting with reduced bulk tissue movement. In some embodiments, the blades always protrude from the tip of the device, for example as illustrated in FIG. 5d. Optionally, the blades only rotate when activated. In some embodiments, the blades are configured such that when they are not activated they do not protrude from the tip of the device. For example, the blades only protrude when they are activated, for example as illustrated in FIGS. 5e-f. In some embodiments, there are between 4-12 blades. Alternatively, or additionally there are more or fewer blades.

4.2.3 Exemplary Impact Tip

Figures 6A, 6B, 6C:
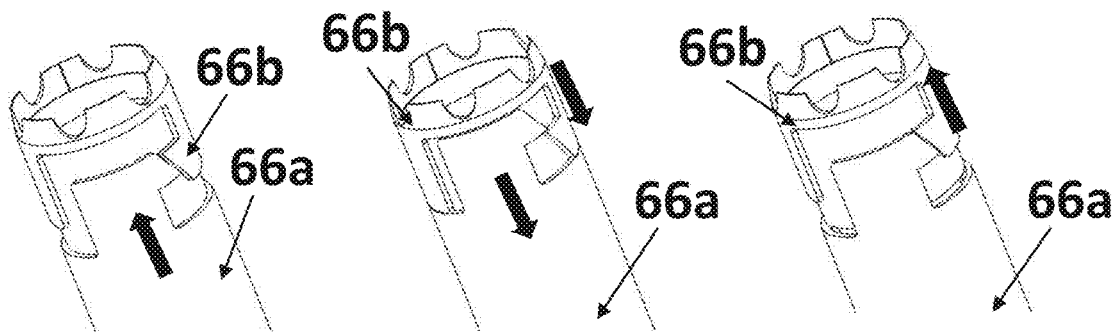
FIGS. 6a-g are schematic views of exemplary embodiments of some exemplary mechanisms of action performed by some operational components located at the distal head, according to some embodiments of the present invention.

Removing tissue surrounding the lead can be difficult. In some cases, the tissue is strongly lodged around the lead and simply trying to separate them does not work. In these cases, a more aggressive procedure is required. In some embodiments, more aggressive procedures include hitting the tissue with something sharp and/or with something blunt. Contrary to prior art techniques, in which the force necessary to dislodge the tissue was apparently difficult to control, the following exemplary procedures are controlled, localized and the range of motion of the hitting element is controlled as well. In some embodiments, the distal tip includes a mass which is pulled proximally and/or pushed distally. In some embodiments, the mass is pulled against a spring and then released. Upon release the mass optionally accelerates distally until it impacts the fibrous tissue, and/or impacts another component of the tip which contacts the fibrous tissue. In some embodiments, the momentum of the accelerated mass enhances the penetration and/or dilation of fibrous tissue, for example as illustrated in FIGS. 6a-c. In this example, the impact tip is designed so the moving mass impacts directly on the tissue that it is intended to penetrate. FIG. 6a shows how the actuator 66a moves distally to engage the mass 66b. FIG. 6b shows how the actuator 66a moves proximally pulling the mass 66b with it against the spring (not shown). FIG. 6c shows how the actuator 66a releases the mass 66b, which accelerates distally until it impacts on the tissue.

In some embodiments, the mass is a tubular structure. In some embodiments, the tubular structure rides either inside and/or outside of a concentric tubular structure. In some embodiments, the mass is pulled proximally while the inner and/or outer tube remains stationary. In some embodiments, pulling the mass proximally optionally separates the mass from fibrous tissue. In some embodiments, after pulling the mass proximally, the mass comprises the space necessary to accelerate when it is released. In some embodiments, after accelerating, the mass optionally impacts fibrous tissue. In some embodiments, the mass impacts the tissue when it passes the distal end of the inner and/or outer tube.

Figures 6D, 6E:
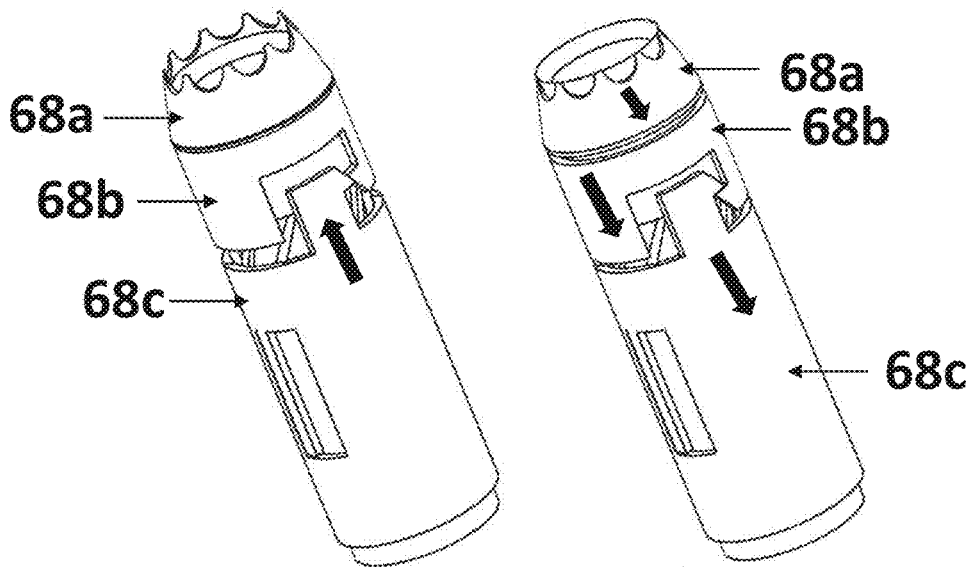
Figures 6F, 6G:
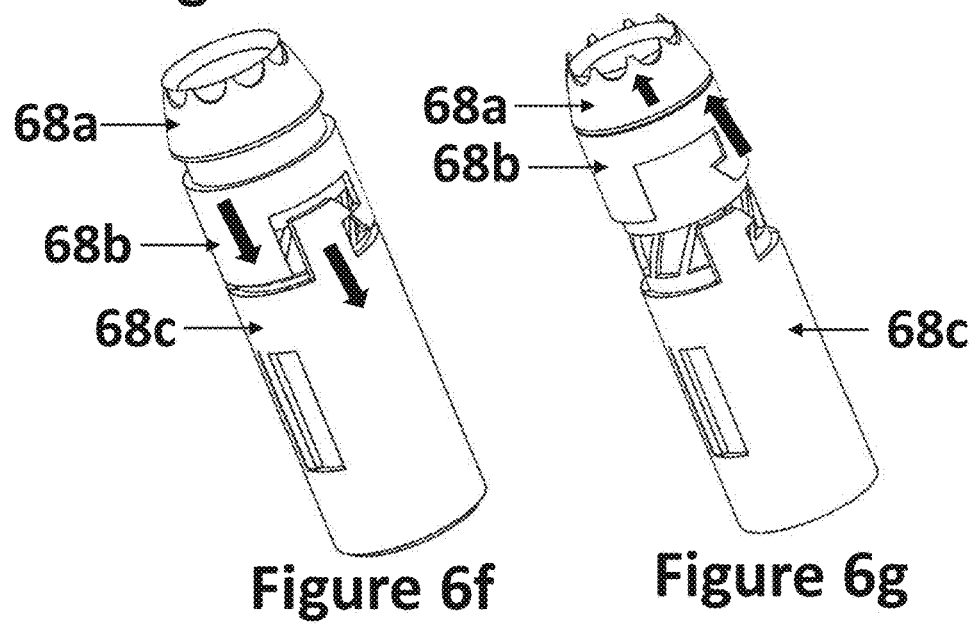

In some embodiments of the invention, the mass impacts on a tissue-contacting component, thereby transferring its momentum to the tissue-contacting component. Optionally, the tissue-contacting component penetrates the fibrous tissue, for example as illustrated in FIGS. 6d-g. In these examples, an impact tip is design so the moving mass 68a impacts on a separate tissue-contacting component 68b that is intended to penetrate the fibrous tissue. In the exemplary configuration, the tissue-contacting component 68b may remain in contact with the tissue continuously, and/or the mass 68a may impact upon the proximal end of the tissue-contacting component 68b, transferring momentum to the tissue-contacting component 68b and/or causing it to penetrate the tissue. FIG. 6d shows how the actuator 68c moves distally to engage the mass 68a. FIG. 6e shows how the actuator 68c moves proximally pulling with mass 68a with it against a spring and/or allowing the tissue-contacting component 68b to move proximally. FIG. 6f shows how the actuator 68c continues to move proximally pulling with mass 68a with it against the spring (not shown) and/or separating the mass 68a from the tissue-contacting component 68b. FIG. 6g shows how the actuator 68c releases the mass 68a, which accelerates distally eventually impacting on the tissue-contacting component 68b and/or transferring momentum to the tissue-contacting component 68b and/or causing it to penetrate the tissue. Optionally, the accelerating mass may not contact the tissue. In some embodiments, this mode optionally enables a separation between the tissue contacting surface and an accelerating mass. For example, the mass remains clear of the tissue and/or is free to run back and forth with reduced contact with the tissue and/or the mass accelerates with reduced friction. In some embodiments, the tissue-contacting component includes a tubular structure which rides inside and/or outside of a concentric tubular structure. In some embodiments, the tissue-contacting structure is optionally limited in its longitudinal movement relative to an inner and/or outer tube. In some embodiments, the range of movement may be less than 2 mm, for example in the range between about 0.1 mm to about 1.9 mm; optionally from about 0.2 mm to about 1.5 mm; optionally from about 0.5 to about 1.0 mm. In some embodiments, the tissue-contacting component is in constant contact with tissue. For example, its distal end penetrates deeper into the tissue with each impact of the mass on its proximal end.

In some embodiments, the proximal movement of one or more tension wires induces the mass to be pulled proximally and then released.

In some embodiments, the proximal movement of one or more tension wires, which induces the mass to be pulled proximally and then released is induced by the user by pulling a trigger. In some embodiments, the pulling of the trigger induces a single impact. In some embodiments, the pulling of the trigger induces multiple impacts. In some embodiments, the impacts are induced by an automated mechanism which induces repeated impacts as long as the mechanism is activated.

In some embodiments, catch and/or release components of the impact mechanism are located in the handle of the device. Optionally the catch and/or release components communicate with the mass and/or spring components of the impact mechanism via tension wires. For example, the wires run through the shaft of the device and/or from the handle to the distal end of the device where the mass and/or spring components are located. In some embodiments, the mass and/or spring components are located near the distal end of the device. In some embodiments, the mass and/or spring components are located proximal to another tissue cutting and/or tissue spreading mechanism. For example, in an exemplary embodiment, the handle of the device comprises a trigger interconnected to a tension wire that runs distally along the shaft and is connected to the actuator. Once the user presses the trigger, the actuator pulls back the mass, crunching the spring and loading the mass, which provides the momentum to the mass to move distally, hitting the tissue-contacting component, which then impacts the tissue.

In some embodiments, an impact mechanism is combined with other tissue cutting and/or tissue spreading mechanisms. For example, combining mechanisms may improve the effectiveness of tissue loosening, spreading and/or penetration of the device. For example, the impact mechanism is combined with a blade rotating mechanism.

4.3 Exemplary Motion Mechanisms

Figure 7A:
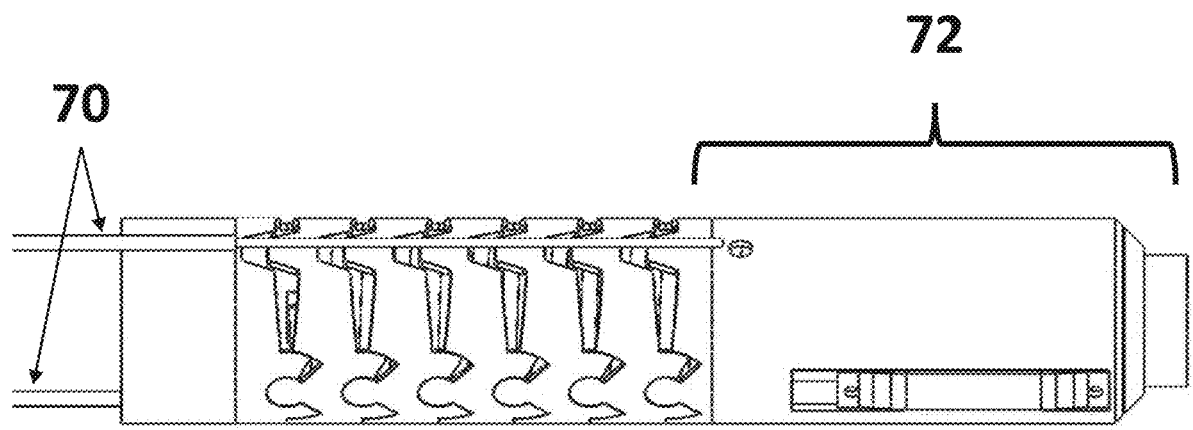
FIGS. 7a-b are schematic views of exemplary embodiments of some exemplary mechanisms of movement performed at the distal head, according to some embodiments of the present invention.

In some embodiments, the motion of the mechanisms of the distal tip is induced through flexible tension wires. For example, flexible tension wires may run from the handle of the device and/or through a flexible shaft of the device to the tip of the device. For example, as illustrated in FIG. 7a, pulling and/or pushing of the tension wires 70 may induce linear movement and/or rotational movement of the components of the tip 72. Some of the components of the tip may be configured such that they convert linear motion of the tension wire into rotational motion of the tip component. Optionally movement and/or changes of movement modes may be at different frequencies. In some embodiments, motion mechanism is used for steering and/or vibrating and/or impacting and/or cutting.

Figure 7B:
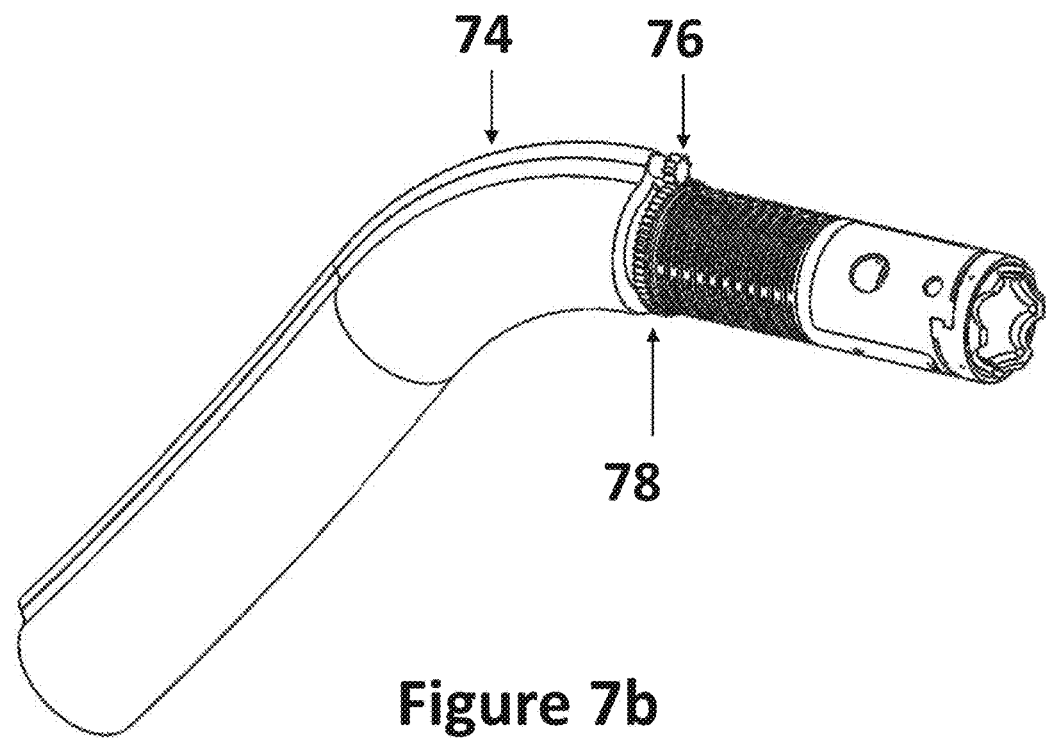

In some embodiments, the motion mechanism runs from the handle, for example, through the sheath, up to the distal head in a dedicated external lumen 74, as shown for example in FIG. 7b. In some embodiments, the motion mechanism is a liner mechanism. In some embodiments, the motion mechanism is a rotational mechanism 76, as shown for example in FIG. 7b. In some embodiments, the rotational mechanism engages a dedicated gear 78, which operates the tool located at the distal head. In some embodiments, an external motion mechanism may be advantageous since no movement is performed inside the lumen of the device, which may reduce the friction of the lead with the lodged tissues while passing through the device. In some embodiments, an external motion mechanism may be advantageous since delivery of the momentum from the handle to the tool is delivered by a wire, for example, using a very small radius. In some embodiments, the radius is from about 0.5 mm to about 3 mm; optionally the radius is from about 1 mm to about 2.5 mm; optionally from about 1.5 mm to about 2 mm. In some embodiments, an external motion mechanism may be advantageous since the OD of the device is smaller than a device with an internal motion mechanism.

4.4 Exemplary Vibration of the Distal Head

In some embodiments, the distal head is vibrated by means of the motion mechanisms described above. In some embodiments, vibration may help is loosening the tissue surrounding the lead since the resonant tends to react and/or break differently to vibrations. In some embodiments, vibration may help in the cutting action. In some embodiments, the distal head of the device includes one or more flexible regions, which are actively controlled. In some embodiments, the active regions are induced to bend or move laterally in one or more directions.

Optionally, the active regions are induced to bend back and forth repeatedly and/or to induce a vibration of the device. In some embodiments, vibration is induced in a distal portion and/or the distal end of the device. Optionally, vibrations soften, separate, disconnect and/or cause the device to penetrate the tissue. In some embodiments, the vibration affects fibrous tissue that is obstructing the movement of the lead by weakening the attachment of the tissue to the lead. This vibration is optionally induced by pulling alternatively on one or more pull-wires. In some embodiments, a pull wire induces the bending of an active region.

Figure 8A:
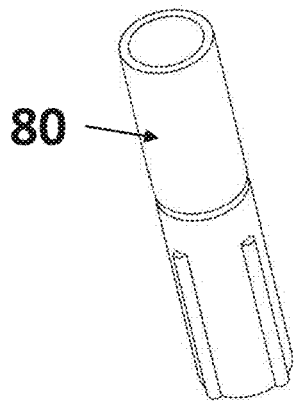
FIGS. 8a-f are schematic views of exemplary embodiments of exemplary activation movements of the distal head, according to some embodiments of the present invention.
Figure 8B:
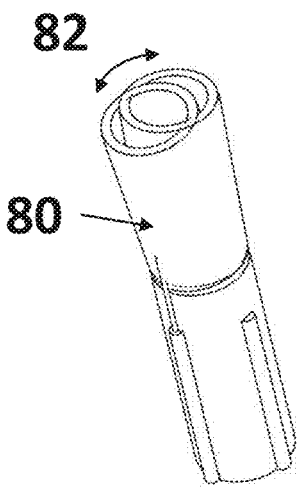
Figure 8C:
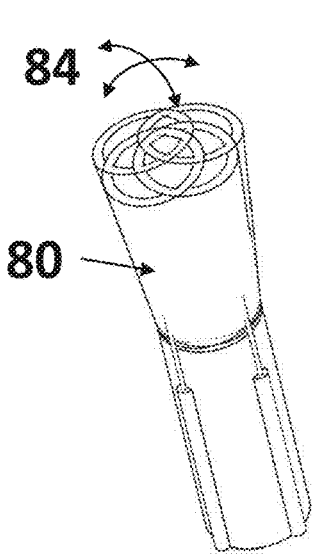
Figure 8D:
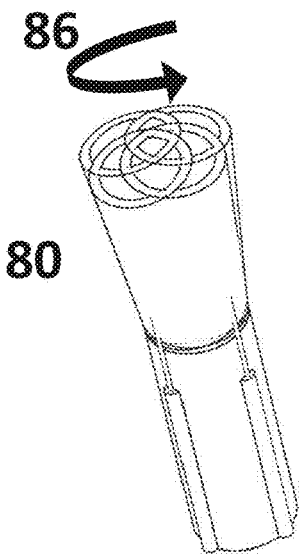
Figure 8E:
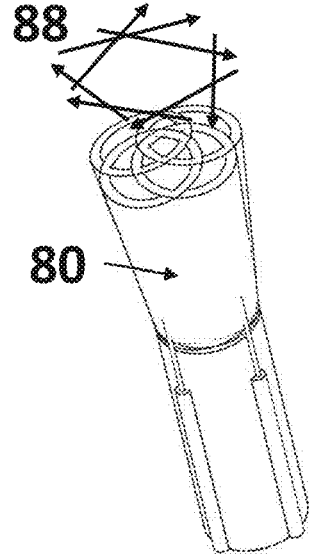

In some embodiments, vibration is back and forth along a single axis of rotation. Alternatively, or additionally, vibration is cyclic and/or among multiple axes of rotation. In some embodiments, vibration is configured to induce a circular, random, and/or other pattern of motion of the distal tip, for example as illustrated in FIGS. 8a-e. FIG. 8a shows an example of a non-activated distal end 80. FIG. 8b shows an example on a one axis vibration 82 of the distal end. FIG. 8c shows an example of a two-axis vibration 84 of the distal end. FIG. 8d shows an example of a circular vibration 86 of the distal end. FIG. 8e shows an example of a random vibration 88 of the distal end. In some embodiments, the amplitude, frequency, and pattern of the vibration are adjusted according to the type of tissue that is being affected. For example, the type of tissue that is causing an obstruction.

In some embodiments, the amplitude of the vibration is in the range of, for example, between about 0.1 mm to about 4 mm; optionally between about 0.5 mm and 3 mm; optionally between about 1 mm and 2 mm. The frequency of vibration is, for example, in the range of between about 1 Hz to about 100 Hz; optionally between about 5 Hz to about 60 Hz; optionally between about 10 Hz to about 20 Hz. In some embodiments, the range of the movement is selected to distinguish tissue types. For example, 2 mm range of movement is compatible for use in the vein wall, but it is not compatible with calcified tissue. In some embodiments, different combinations of amplitude, frequency, and patterns of vibration are used on different types of tissue. For example, larger slower vibration is used to separate softer tissues. Alternatively, or additionally, smaller faster vibrations are used to break up harder tissues. Optionally, combinations of different amplitudes and frequencies are used to achieve the results for different tissue types and/or unknown tissue and/or combinations of different tissue. In some embodiments, the circuitry comprises a lookup table so when the user selects a desired effect and/or type of tissue, the parameters are ready and used. In some embodiments, vibrations are induced manually for example with a trigger activated device handle and/or automatically for example using an automated actuator. In some embodiments, an active vibrator includes a motor, solenoid, pneumatic and/or other type of automated mechanical actuator.

In some embodiments, a bending vibration mechanism is combined with fixed protrusions from the distal tip of the device and/or tissue cutting mechanisms and/or tissue spreading mechanisms at the tip of the device. In some embodiments, the combination increases the effectiveness of the tissue penetration. In some embodiments, cutting, spreading and vibration are synchronized. For example, different modes may be activated separately (for example to avoid uncontrolled damage) and/or different modes may be activated simultaneously (for example to cut more aggressively). In some embodiments, the circuitry comprises a lookup table so when the user selects a desired mode, the parameters are ready and used.

Figure 8F:
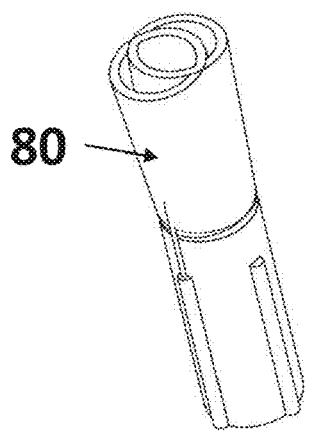

In some embodiments of the invention, the device includes a stiff tube. For example, an inner tube that is stiff. Alternatively, or additionally, the device includes a stiff outer tube. In some embodiments, the stiffness is defined as the stiffness necessary to transmit the vibrations in an amplitude of motion that is no more than half, or ⅓, or ⅕ or ¹⁄₁₀ of the amplitude of the vibrating tube. Optionally, the stiff tube does not bend significantly due to vibrations. Optionally, the inner tube holds the lead wire centered while the outer tube vibrates, moving the tissue relative to the lead wire, for example as illustrated in FIG. 8f.

In some embodiments, the stiff tube is semi-rigid. In some embodiments, the stiffness is defined as the stiffness necessary to transmit the vibrations in an amplitude of motion that is no more than half, or ⅓, or ⅕ or ¹⁄₁₀ of the amplitude of the vibrating tube, while also having a bending radius of about 10 cm without kinking. For example, the semi-rigid tube is flexible enough to bend slightly in order to navigate easily through the vasculature but does not flex easily or quickly enough to vibrate together with the outer tube during vibration. For example, the inner tube resists the movement of the lead with the vibration of the outer tube. In some embodiments, this resistance optionally causes the vibration to separate the tissue from the lead.

Figure 9A:
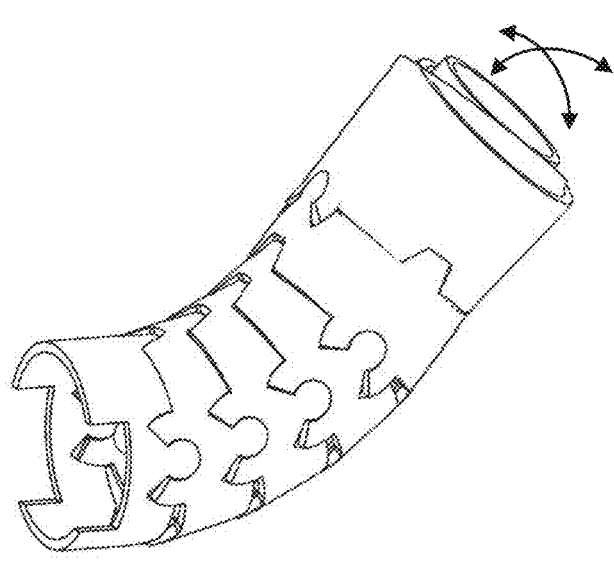
FIGS. 9a-b are schematic views of exemplary embodiments of vibration of the outer tube, according to some embodiments of the present invention.
Figure 9B:
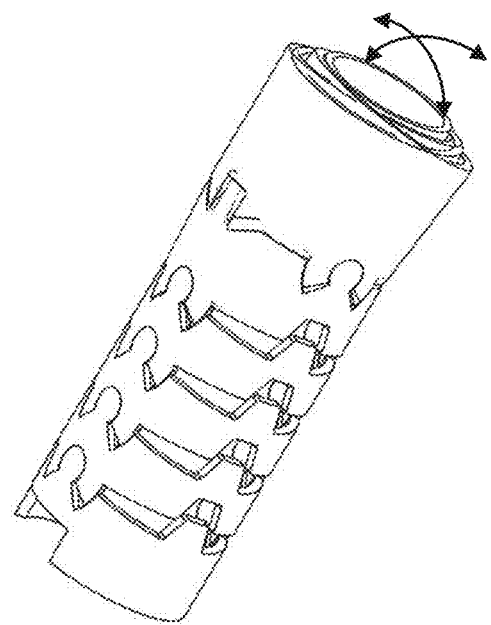

In some embodiments, a tube (for example an inner tube) bends in a controlled fashion. For example, controlled bending is achieved through the use of two tension wires on opposite sides of an axis of bending. For example, controlled bending of an inner tube may facilitate aligning a distal portion of the device with the orientation of the lead wire, as it bends within the vasculature, or with the orientation of the blood vessel itself. For example, during operation, the inner tube may be held at the appropriate bending angle, while the outer tube is vibrated around the inner tube. Optionally, vibration of the outer tube may loosen or detach the tissue from the lead wire, for example as illustrated in FIGS. 9a-b. FIG. 9a shows an example of a vibration about one axis with built-in hinge. FIG. 9b shows an example of a vibration about two-axes with built-in hinge.

4.5 Exemplary Eccentric Rings

Figure 10A:
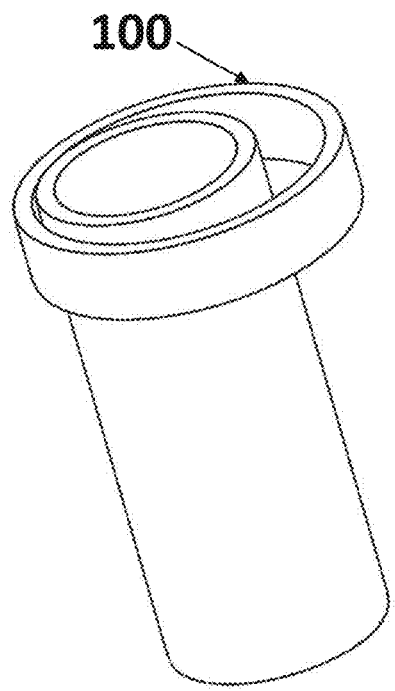
FIGS. 10a-e are schematic views of exemplary eccentric rings, according to some embodiments of the present invention.
Figure 10B:
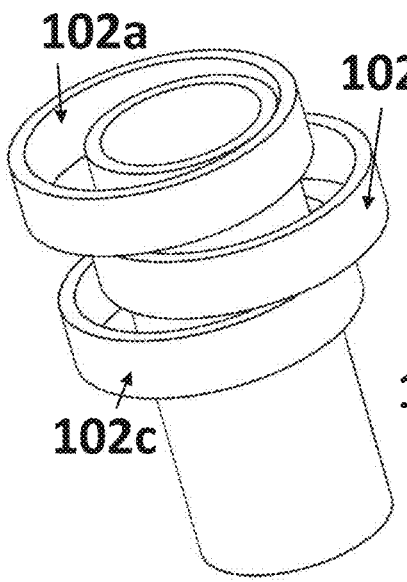
Figure 10C:
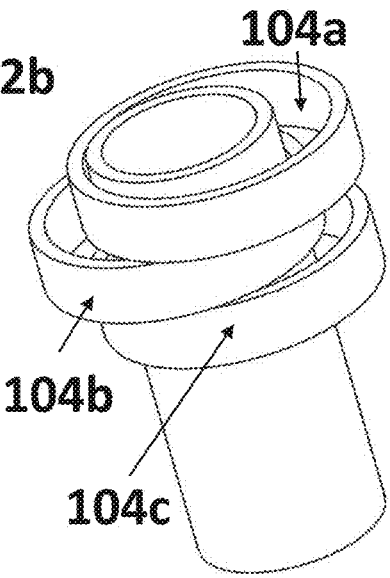

In some embodiments, the distal head of the device comprises a mechanism for breaking and/or separating and/or weakening the tissue surrounding the lead by exerting radial force. In some embodiments, the tissue breaking mechanism contains one or more eccentric rings. In some embodiments, the cross section of a ring may be circular, elliptical, egg shaped, or any other shape. In some embodiments, the ring is a complete ring. In some embodiments, the ring is a broken ring. Optionally, the position of the ring is at or near the distal end of the device. In some embodiments, rotation of the one or more eccentric rings causes them to exert force radially. Alternatively, or additionally, during rotation a ring exerts forces in different directions to induce stretching, breaking, tearing, loosening, and/or detachment of the tissue around the lead, as illustrated, for example in FIGS. 10a-c. FIG. 10a shows an example of an embodiment with one ring 100. FIG. 10b shows an embodiment with multiple rings 102a-c. FIG. 10c shown an embodiment of multiple ring of different sizes 104a-c.

In some embodiments, the device comprises more than one eccentric ring, and/or the largest radial extension of the rings increases with their distance from the distal end of the device to form a tapered form such that, as the device is advanced through the tissue, the opening in the tissue is enlarged. In some embodiments, adjacent rings rotate in opposite directions. In some embodiments, rotation in opposing directions may increase the effectiveness of the tissue separation.

Figure 10D:
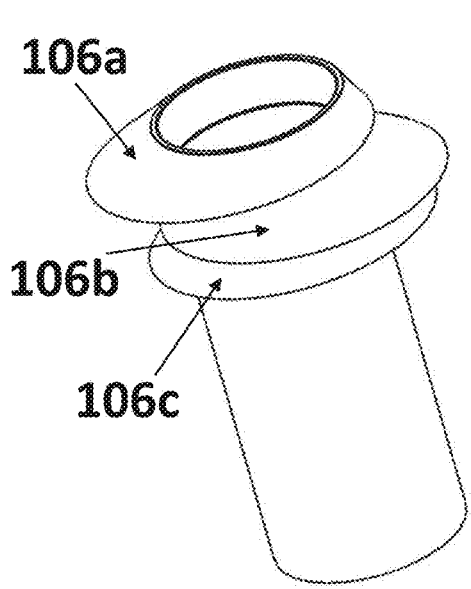
Figure 10E:
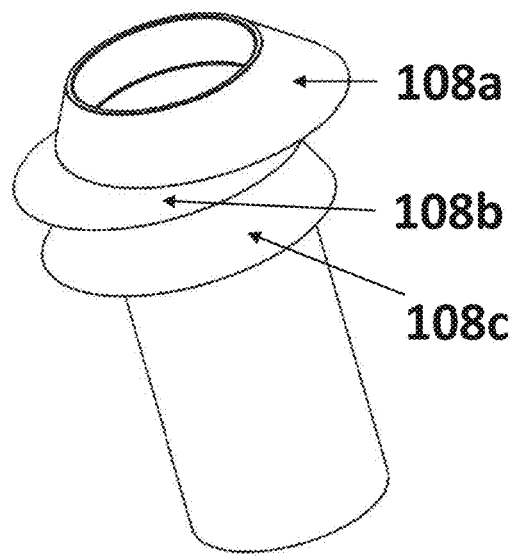
Figure 12A:
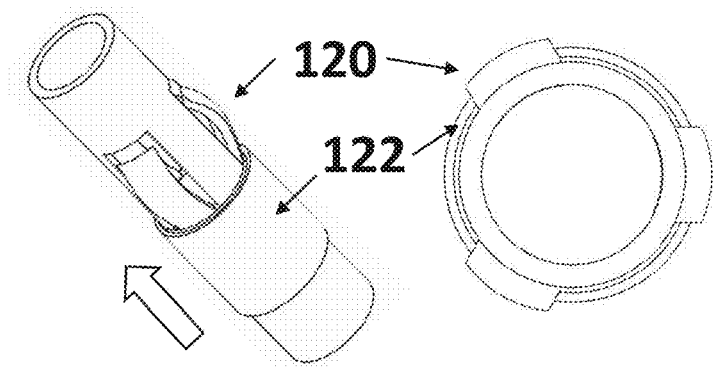
FIGS. 12a-d are schematic views of exemplary lead wire grasping tool, according to some embodiments of the present invention.
Figure 12B:
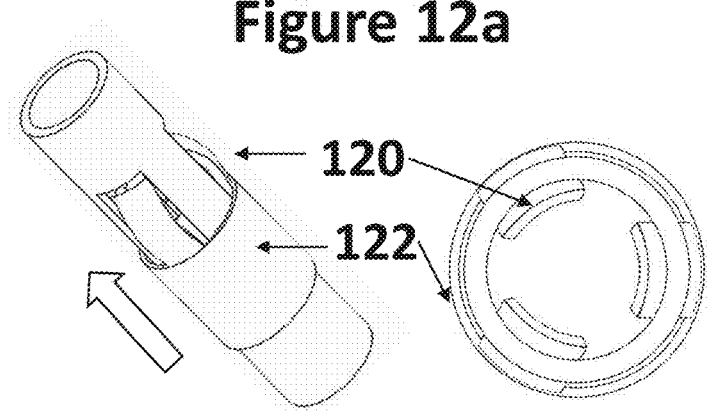
Figure 12C:
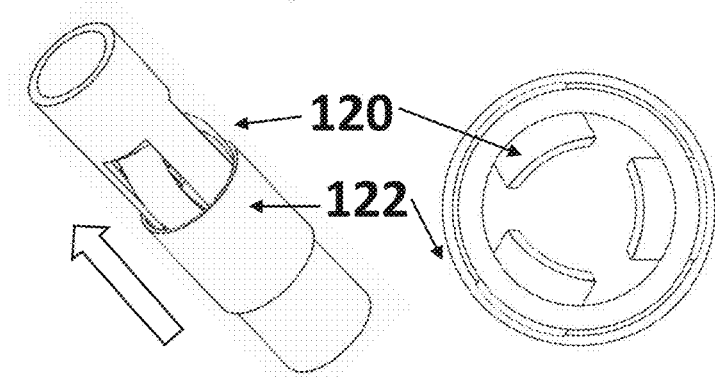
Figure 12D:
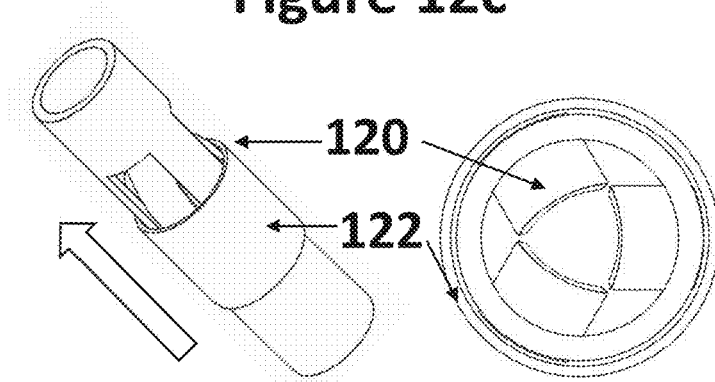

In some embodiments, each eccentric ring is cone shaped, having a smaller radius at its distal edge and a larger radius at its proximal edge to make it easier for the device to advance into the fibrous tissue and the make it more effective at separating the fibrous tissue, as illustrated, for example in FIGS. 10d-e. FIG. 10d shows an embodiment of multiple cone shaped rings 106a-c. FIG. 10e shows an embodiment of multiple cone shaped rings of different sizes 108a-c. In some embodiments, there are gaps between the rings. In some embodiments, the connection between the rings provides a continuous slope.

4.6 Exemplary Tissue Spreaders

In some embodiments, the distal head of the device comprises a mechanism that enters between the tissue surrounding the lead and the lead. In some embodiments, the tissue is expanded locally, radially and in a limited manner. In some embodiments, the device comprises tissue spreaders at or near the distal end of the device. In some embodiments, tissue spreaders include components located at or near the distal end of the device that spread tissue in a radial direction.

In some embodiments, the tissue spreaders function by bending radially outwards. For example, they bend outward after they have penetrated the tissue or scrapped between the lead and the tissue. In some embodiments, the tissue spreaders are bent radially outwards. For example, when the spreaders are pulled into a tube of the device they straighten and/or when they are pushed distally to penetrate the tissue they at first protrude penetrating the tissue and/or when they protrude from the tip of the device they may bend radially outwards. In some embodiments, the radial protrusion optionally pulls the penetrated tissue radially outward away from the lead wire, for example as illustrated in FIGS. 11a-c.

In some embodiments, the tissue spreaders include round or flat wires (parallel to the device) and/or they may be flat and/or they may be significantly wider than they are thick. In some embodiments, the spreaders comprise a thickness from about 0.1 mm to about 1 mm; optionally from about 0.3 mm to about 0.8 mm; optionally from about 0.4 mm to about 0.6 mm. In some embodiments, the spreaders comprise a wideness from about 1 mm to about 5 mm; optionally from about 1.5 mm to about 4.5 mm; optionally from about 2 mm to about 4 mm. Optionally, the tissue spreaders are distributed around the circumference of the distal tip of the device. In some embodiments, there may be between three to 20 or 30 spreaders. Optionally, the spreaders are rigid enough to penetrate and/or push away tough fibrotic tissue. Optionally, the spreaders are strong enough, for example 0.01 Newton, or 0.1 Newton, up to 1 Newton, to spread and/or tear the tissue radially outwards. In some embodiments, the force of spreading may be due to the bending forces in the spreader. In some embodiments, the force of spreading is due an inner tube that presses the spreaders radially. In some embodiments, the spreaders may be made of Nitinol or another super-elastic material. In some embodiments, the spreaders are straightened while inside the tip of the device and bend forcefully outwards to spread the tissue. FIG. 11a shows an example of an embodiment of 8 tissue spreaders retracted. FIG. 11b shows an example of an embodiment of 8 tissue spreaders 110 partially extended. FIG. 11c shows an example of an embodiment of 8 tissue spreaders 110 fully extended and bent outwards.

In some embodiments, the spreaders extend distally from the distal end of a tube and are arranged around the circumference of the distal end of the tube, as illustrated for example in FIGS. 11d-e. In some embodiments, the spreaders are formed from longitudinal cuts in a tube. In some embodiments, the spreader flaps formed by the cuts are forced to bend radially outward by a ring located inside of the flaps and pulled proximally. In some embodiments, the ring is connected to a puller tube located proximal to the ring which slides along the outside of the cut tube by a number of connecting ribs which pass between the flaps. In some embodiments, the flaps have a defined living hinge, which is more flexible than the rest of the flap. In some embodiments, this hinge point is made more flexible by cuts in the tube at the location of the living hinge. In some embodiments, the flaps are bent such that they bulge radially outwards around the ring and then bend back inwards distal of the ring. FIGS. 11d-f show an example of an embodiment of a device tip with optional spreaders 112 formed from cuts in a tube, which are pushed radially outwards by a ring 114 located inside the flaps which is pulled proximally.

In some embodiments, the spreader includes a circumferential band around the circumference of a distal portion of the device. In some embodiments, the circumferential band is optionally expanded radially outward by pushing or pulling the ends of the band along the circumference of the distal portion such that a portion of the band bulges radially outward. In some embodiments, the band optionally cover a portion of the circumference of the tip region, such as a portion (for example one third, one half, and/or two thirds of the circumference or may cover the entire circumference of the tip region of a tube). Optionally, there are multiple bands. In some embodiments, the ends of the bands are located at different points around the circumference, whereby pushing or pulling the ends of the multiple bands induces bulging radially outward at multiple regions around the circumference. In some embodiments, an end of each band 116a is connected to an outer tube 116c and the other end of each band may be connected to an inner ring 116b. For example, a portion of the band may pass through a window in the outer tube 116c. In some embodiments, rotation of the inner ring 116b relative to the outer tube 116c optionally causes the band 116a to bulge radially outwards, for example as illustrated in FIGS. 11g-i. FIG. 11g shows an example of an embodiment of a "bulging band" 116a spreader mechanism in a contracted configuration. FIG. 11h shows an example of an embodiment of a "bulging band" 116a spreader mechanism in a partially expanded configuration. FIG. 11i shows an example of an embodiment of a "bulging band" 116a spreader mechanism in a fully expanded configuration.

In some embodiments, the spreader mechanisms are combined with a rotational movement and/or with a longitudinal movement and/or with an impact mechanism. For example, the combined mechanisms aid in the loosening and/or spreading of the tissue and/or with the tissue penetration of the device.

4.7 Exemplary Lead Wire Grasping

In some embodiments, the device includes a mechanism to grasp a lead wire within an inner lumen of the device. For example, the wire is grasped near the distal end of the device. For example, grasping occurs during actuation of the distal tip of the device. In some embodiments, the grasping mechanism includes an inflatable component that reduces the inner diameter of the inner lumen of the device. In some embodiments, the grasping device includes a mechanical component that protrudes inward from the wall of the device into the inner lumen reducing the diameter of the inner lumen of the device. In some embodiments, the grasping component comprises bent flaps. For example, the flaps may be formed by cutting the wall of a tube. Optionally, the flaps 120 are pushed inwards to contact the lead, for example, by sliding an outer tube 122 over the protruding portions of the flaps 120, as illustrated for example in FIGS. 12a-d. FIGS. 12a-d show an exemplary lead grasping mechanism made from 3 flaps 120 cut in the wall of a tube and bent to form grasping components that are pushed inwards to contact the lead by the movement of an outer tube 122 over the protruding portion of the flaps. Left: oblique view, Right: top view. In some embodiments, for example, the use of the lead wire grasping tool may ensure that the user applies force to the lead at the place where lead is lodged in the tissue.

In some embodiments, a mechanism to grasp the lead wire within an inner lumen of the device is combined with other mechanisms such as cutting blades, circumferential expansion, tissue spreading, or any other mechanism. For example, the other mechanisms may apply forces on tissue in order to loosen it and/or separate it from the lead wire and/or the vessel and/or heart wall.

4.8 Exemplary Tissue and Binding Site Assessment

In some embodiments, during the lead extraction procedure, the lead extraction device comprises the ability to distinguish, in real time, between different types of matter that the distal end of the device encounters during the procedure. In some embodiments, this ability assists in the intra-procedural decision-making and increase safety. In some embodiments, for example, an indication that the LE device cutting or ablating head is facing a blood vessel tissue, rather than plaque or blood fluid, may suggest to the clinician to steer the device head, if possible, or at least to stop activating the device in that direction. In some embodiments, for example, the device comprises the ability to classify a binding site based on the chemistry of the plaque, and judge whether it is more fibrotic or more calcified. In some embodiments, this ability aids in the selection of the appropriate tool (for example: some laser LE devices are more suitable for cutting through fibrotic plaque than for penetrating a calcified plaque).

Figure 13:
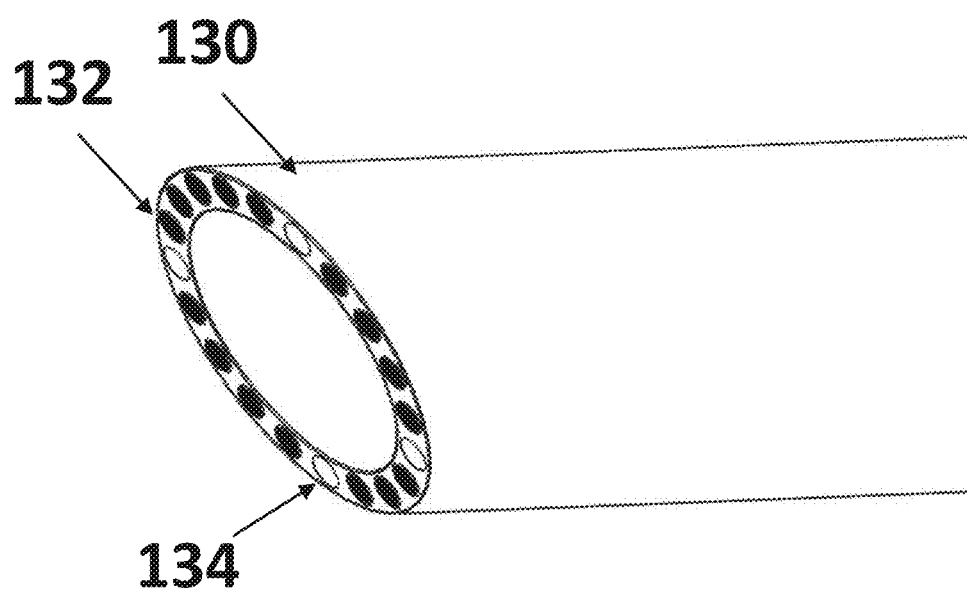
FIG. 13 is a schematic view of an exemplary integration of spectroscopy components with ablation components at the distal head, according to some embodiments of the present invention.

4.9 Exemplary IR (Infrared) Spectroscopic Classification of Matter Distally to the Device Head In some embodiments, the device comprises integration of spectroscopy components with ablation components, either within the lead extraction (LE) device structure or as part of an add-on or accessory device (see below—section 12), to assemble a spectroscopy system for the classification of objects distally and around the device head (FIG. 13). In some embodiments, for example, the classification is between blood fluid, blood vessel tissue, fibrotic plaque, calcified plaque and the lead itself. In some embodiments, the system provides a feedback to the clinician in the form of a score or a color scale, to distinguish between the possible objects. In some embodiments, the system provides indication that the device head is in proximity to the object in front of it, and, in some embodiments, comprises an alarm feature, to warn the clinician from further advancement.

In some embodiments, the system includes a single or multiple light emitting components, such as optical fiber tip or a light emitting diode (LED). In some embodiments, these components are mechanically positioned to radiate in a direction aligned with the LE device head. In some embodiments, depending on the light emitting technique, the signal to be radiated is carried in, to the tip of the device, by optical fibers or electrical wires along the length of the catheter. In some embodiments, the reflected signal is collected by a lens and transmitted either to an optical fiber (to be carried outside the body) or to a photodiode to convert the light to an electrical signal (to be carried outside the body by an electrical wire). In some embodiments, the system comprises a control unit used to induce either light or electrical signal, and to analyze reflected signal, whether optical or electrical. In some embodiments, the system comprises dedicated software and algorithms with examples of functions, lookup tables, activation/deactivation rules, machine-learning models, neural network models, other models, and/or ranges to classify tissue based on spectroscopic values.

In some embodiments, the fibers used for spectroscopy are integrated as part of the fibers 130 that perform the ablation functionality—as can be seen, for example, in FIG. 13. FIG. 13 shows an example of an embodiment of a laser lead-extraction device comprising ablating fibers 130 (ablating fibers are 'black' circles 132, spectroscopy fibers are 'white' circles 134).

4.10 Exemplary Ultrasonic Classification of Matter Distally to the Device Head

In some embodiments, the system comprises an ultrasound system for the assessment of mechanical properties of a matter, for example, based on echo analysis. In some embodiments, the generated sound waves by the transducers, propagates through the matter and is reflected according to its acoustic or mechanical properties.

In some embodiments, this modality is used to classify between blood vessel tissue, blood fluid, fibrotic plaque, calcified plaque or the lead itself, based on their acoustic properties.

In some embodiments, ultrasound transducers are embedded and/or incorporated on the head of the LE device for the purpose of matter classification. In some embodiments, the ultrasonic transducer is designed as a single piezoelectric transducer that mechanically rotates several thousand times per minute around the LE device head and thus creates a beam that is centered on and around the catheter head and projects the region ahead of it. In some embodiments, an electronic phased array of transducers are stationary placed around the device head and sequentially activated to create a focal point—of ultrasonic energy in a process known as beam forming. In some embodiments, the element 130 in FIG. 13 can be a piezo electric transmitter and/or receiver. In some embodiments, the ultrasonic system is also used to detect device proximity to the object and provides alerts on being at close proximity (e.g. 1-2 mm) to the blood vessel wall or the lead itself.

4.11 Exemplary Lead Cutter

In some cases, during the lead extraction procedure, the user arrives at the conclusion that the lead cannot be taken out from the tissue without causing too much damage. In these cases, it may be preferable to cut the reminder of the lead instead of forcing it out.

In some embodiments, the distal end of the LE device comprises a lead cutter. In some embodiments, the lead cutter works on a lead that is located at the lumen of the device. In some embodiments, the cutting of the lead is done by bending the lead where a blade, along the tube, can cut it. In some embodiments, the bending of the lead is done within the tube or outside the tube. In some embodiments, the lead is actively bent towards the blade. In some embodiments, the blade is a dedicated blade for lead cutting. In some embodiments, the blade is a tissue cutting blade.

Figure 14A:
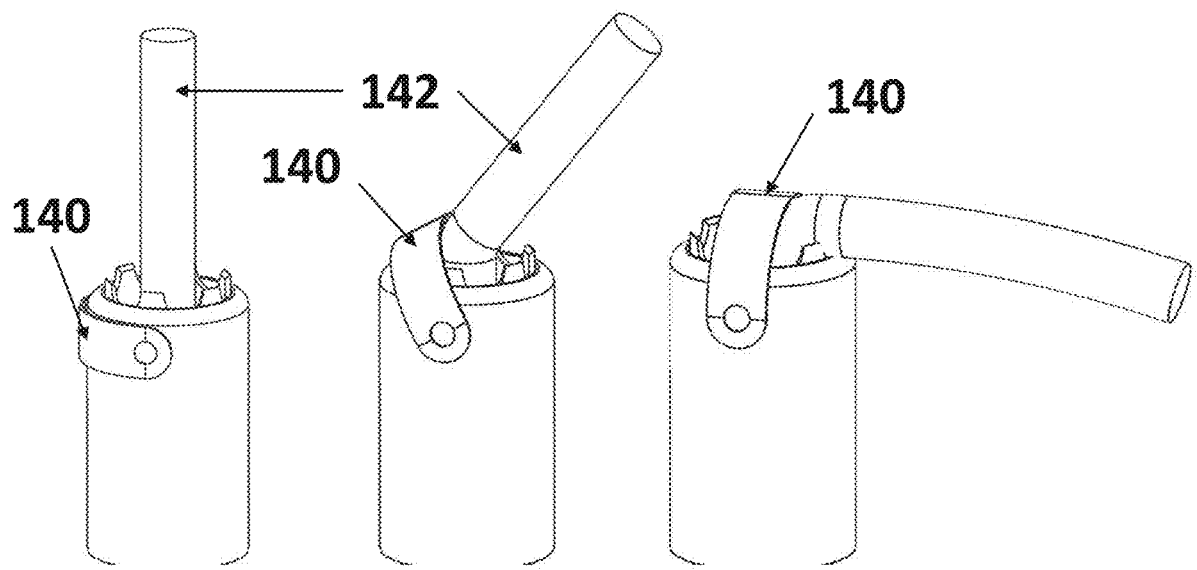
FIGS. 14a-b are schematic views of exemplary lead cutter tool, according to some embodiments of the present invention.

In some embodiments, the lead cutter comprises a small moving part 140, optionally as an add-on or accessory (see below—section 12), that slides and engages the lead 142 when the extractor is out or while the extractor is still in position where a cut is needed by the user, as shown for example in FIG. 14*a*.

In some embodiments, the lead cutter can be redrawn and/or reloaded after a cutting attempt was done for relocating or replacing a tool, according to the user decision.

Figure 14B:
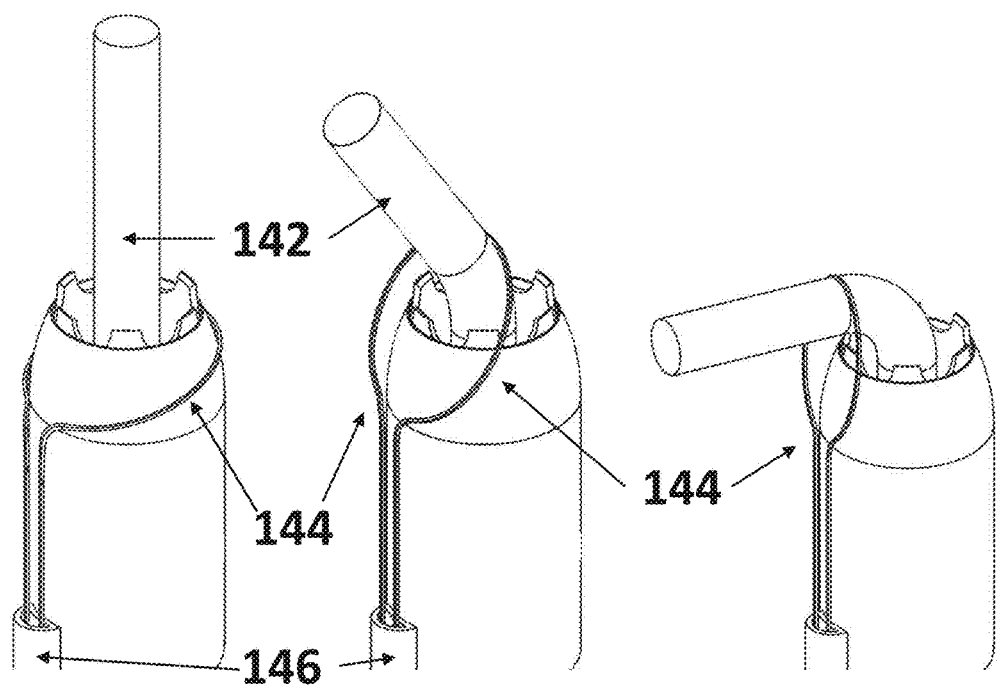

In some embodiments, the lead cutter comprises a wider device, optionally as an add-on or accessory (see below—section 12), that goes around the extractor, as shown for example in FIGS. 14*b*. In this embodiment, a wire-like 144 is shown to exit from an external additional elongated tube 146 running parallel to the LE device. In some embodiments, the wire-like 144 is made, for example, of nitinol or any other material. In some embodiments, the wire is in a non-deployed state hugging the LE device (left side). In some embodiments, a dedicated groove (not shown) is used to keep the wire in its non-deployed state. In some embodiments, the groove is perpendicular to the LE device. In some embodiments, the groove is non-perpendicular to the LE device, having a diagonal orientation. In some embodiments, the wire "natural" memory state is in an opposite orientation related to the non-deployed state. This means that, once deployed, the wire will try to return to the "natural" memory state, which is moving apart from the LE device.

In some embodiments, the external additional elongated tube 146 running parallel to the LE device and containing the wire is irreversibly attached to the LE device. In some embodiments, the external additional elongated tube 146 running parallel to the LE device and containing the wire is reversibly attached to the LE device. In some embodiments, the external additional elongated tube 146 running parallel to the LE device and containing the wire is adapted to move forward and backwards in relation to the LE device.

In some embodiments, the lead is cut by using the existing deployable blades in the LE device. Since the lead is attached on its distal part to the heart and is being pulled from its proximal part by the user, a tension is created on the lead. In some embodiments, a steering movement of the distal part of the LE device while maintaining the tension created on the lead induces a sharp bending radius to the lead and forces the lead to "lean" on the edge of the distal end where the rotating blades are located and deployed. The steering mechanism is strong enough to provide the force necessary to cut the lead by means of the blades and the tension created on the lead itself.

5. Exemplary General Mechanisms/Characteristics of the Device 5.1 Exemplary Motion Repetition In some embodiments, a movement of one or more of the components is repeated. In some embodiments, repetitions are due to manual repetition. In some embodiments, repeated motions are motor driven. In some embodiments, the user controls the rate of repetition. In some embodiments, a repetition rate may range between 0.1 Hz to 300 Hz; for example 1-100 Hz, for example 25-80 Hz, for example 50 Hz, for example 1-10 Hz. In some embodiments, the frequency is selected among several predefined frequency modes, alternatively or additionally, a frequency is selected over a continuous range of frequencies. Alternatively or additionally, a frequency is adjusted automatically. In some embodiments, a combination of multiple frequencies is used. In some embodiments, the frequency regime is chosen to achieve a clinical goal. In some embodiments, the clinical goal may be related to the tissue type and/or breaking of the tissue from the lead and/or separating the tissue from the lead. In some cases, it is preferred that a lodged segment of 1 cm of the lead, be breached in less than 1 minute, better in less than 30 seconds, better in less than 10 seconds. In some embodiments, the device makes a forward progress of at least 0.1 mm, better 0.2 mm, better 0.3 mm per each activation cycle of the device (e.g. per hit, or cut motion, or vibration, or a combination of these). In some embodiments, this progress is achieved with minimal force applied by the user from the proximal end of the device or in pulling the lead, for example with a force less than 10 Newton, for example less than 5 Newton, for example less than 3 Newton, for example less than 2 Newton. In some embodiments, a repetition rate of 3-10 cycles per second should provide, for example, a total progress rate of 3 mm-1 cm in 10 seconds. Optionally, the frequency regime is adjusted depending on tissue types and/or with different challenges and/or for selecting a speed of progression. For example, the frequency ranges between 5 Hz to 10 Hz. For example, the frequency is less than 70 Hz, and/or less than 30 Hz and/or less than 20 Hz. Optionally, the frequency ranges between 5 to 20 Hz. In some embodiments, higher frequency ranges are selected for one or more of the components. In some embodiments, one or more of the components, having an interface with and/or in proximity to the tissue, is activated with repeated motion at one or more frequencies of above 100 Hz. In some embodiments, the frequency ranges between 500 Hz to 2 KHz and/or between 2 KHz to 5 KHz and/or between 5 KHz to 10 KHz and/or between 10 KHz to 15 KHz, and/or between 15 KHz to 20 KHz or above. In some embodiments, the one or more frequencies may be supersonic and/or ultrasonic. In some embodiments, the system comprises dedicated software and algorithms with examples of functions, lookup tables, activation/deactivation rules, machine-learning models, neural network models, other models, and/or ranges to activate frequency regime based on the type of tissue.

In some embodiments, the one or more frequencies and/or one or more frequency controls for one component of the catheter differs from another component. In some embodiments, frequencies of different components may be independent. Alternatively or additionally, frequency of one component may be dependent on a frequency of another component. In some embodiments, bending may be repeated at one or more frequencies in one axis while repeated in a different one or more frequencies in a second axis. In some embodiments, bending is repeated in one or more frequencies while the impact is at another one or more frequencies. In some embodiments, the bending is at one or more frequencies while cutting blades and/or spreading mechanism act at one or more other frequencies.

In some embodiments, one or more of the components of a catheter have power control for regulating a force being applied to it or by it to another component and/or by it to tissue. In an example, the catheter may include one or more force limiters. In some embodiments, a force limiter might be, for example, a spring with a spring constant k, which is large. In some embodiments, the spring lies in series with the force-applying element. In some embodiments, when the force applied is close to the designed limit, the spring starts to respond and compress, taking some of the force instead of the target.

In some embodiments, one or more of the components of a catheter may have motion magnitude control for regulating the extent of motion being applied to it or by it to another component and/or by it to tissue. For example, a catheter may include one or more motion limiters.

In some embodiments, the one or more frequency and or one or more power controls for moving one or more of the components is controlled-based, at least in part on input from a sensor. For example, the sensor relates to force applied to the tissue. Optionally or additionally, for example, the sensor relates to the power needed to move a component of the catheter. For example, the sensor relates to magnitude of motion.

In some embodiments, one or more motion limiters and/or force limiters is controlled, at least in part by a sensor.

In some embodiments, a system provides to an operator (for example a physician) one or more indications of the force and/or the motion and/or the location, and/or the bending angle of one or more of the components of the catheter. In some embodiments, the operator receives information based on a sensor. In an example, the handle includes an indicator of the position of wires and their extension. For example, from the indicator, the operator may observe the motion of a certain component. In some embodiments, the system provides information about bending (e.g. angle) of the catheter and/or its tip. In some embodiments, the system provides information about a lateral forces and/or a longitudinal force and/or a pressure on tissue and/or a friction applied on a portion of the catheter by tissue and/or by a vein and/or the system may provide information on a central lead and/or other leads.

5.2 Exemplary Modifiable Mechanical Properties

In some embodiments, the catheter comprises a mechanism that adjusts mechanical properties of the catheter. For example, the catheter's shaft includes one or more lumens, which are used for the insertion of property adjusting elements. For example, a property-adjusting element may include stiffening rods. In some embodiments, stiffening rods are made of stainless steel, nitinol, polymers having various mechanical properties, or any material that has advantageous mechanical properties to modify the mechanical properties of the catheter shaft. In some embodiments, the stiffening rod is made of nitinol and is configured to make the catheter shaft more pushable without significantly increasing the stiffness. In some embodiments, the stiffening rod is made of stainless steel and is intended to significantly increase the stiffness of the catheter shaft. In some embodiments, the stiffening rods are coated with PTFE or another highly lubricious material to aid in insertion into the lumen. In some embodiments, the one or more lumens are lined with PTFE or another highly lubricious material to aid in insertion of the rods into the lumens. In some embodiments, the stiffening rods are inserted into and/or removed from the catheter shaft without having to remove the device from the patient. In some embodiments, the modification of mechanical properties is controlled manually or automatically. In some embodiments, the user manually modifies the mechanical properties from the handle of the device. In some embodiments, sensors located on the shaft and/or on the distal head receive inputs that modify automatically the mechanical properties. In some embodiments, the system comprises dedicated software and algorithms with examples of functions, lookup tables, activation/deactivation rules, machine-learning models, neural network models, other models, and/or ranges to activate the modification of the mechanical properties based on the input received by the sensors and/or from the user.

5.3 Exemplary Combinatorial Use of Components/Embodiments

In some embodiments, one or more components and/or subcomponents and/or embodiments and/or sub-embodiments described therein are used and/or included once or more than once within an embodiment. For example, one or more components are combined with other one or more component and/or a subcomponent and/or embodiment and/or sub-embodiment described in the present invention and together their combination forms an embodiment described therein.

5.4 Exemplary Characteristics of the Pull-Wires and Lumens of the Device

In some embodiments, the device comprises pull-wires, which run through the catheter shaft to actuate a distal portion of the catheter. In some embodiments, a pull wire runs inside a sleeve, which passes through a lumen in a multilumen catheter shaft. In some embodiments, a lumen is larger than the outer diameter of the sleeves so that the sleeve is free to bend slightly within the lumen. In some embodiments, bending of a sleeve within a lumen allows the sleeve to compensate for bending of the shaft. In some embodiments, the compensation does not change the total length of the lumen within the catheter shaft. In some embodiments, a sleeve is rigidly connected to the catheter shaft at both ends and/or is free to move within the lumen along the length of the shaft, thereby maintaining the same pull-wire length independent of the shaft bending. In some embodiments, a multilumen shaft twists along its length, doing one full revolution every 20-100 cm, optionally there is a twist over fixed and or varying intervals ranging between 20 to 30 cm and/or between 30 to 50 cm and/or between 50 to, 75 cm and/or between 75 to 100 cm. In some embodiments, each braid may increase the flexibility of the shaft when pull-wire and pull-wire sleeves are passed through the lumens. In some embodiments, the pull wires, which go through the sleeve, shrink or stretch when the catheter is bent. In some embodiments, controlling the tension in the pull wires during the shrinking or stretching is done, for example, by twisting the multilumen shaft, which causes a wire in one segment to shrink and to stretch in another, with the total canceling out.

In some embodiments, tensile elements (for example wires and/or cables) run through the flexible shaft of the device. For example, tensile elements run from a handle of the device to a distal tip of the device. In some embodiments, wires are optionally connected and/or grouped. In some embodiments, one wire running along the shaft may connect to multiple wires near the tip. In some embodiments, grouping may reduce the number of tensile elements running through the flexible. In some embodiments, grouping may reduce the number of tensile elements connected to a handle. In some embodiments, the tensile elements will run independently and/or separately through the flexible shaft. In some embodiments, some tensile elements are used to adjust properties of the device and/or some tensile elements may be for feedback and/or some tensile elements will be used for control.

In some embodiments, the device includes a mechanism to compensate the tension of the tensile elements due to curves in the flexible shaft or/and in a hinge or/and during vibration. In some embodiments, the compensation is controlled. In some embodiments, the compensation is controlled automatically, using a spring in the tip or/and in the handle.

5.5 Exemplary Tension Control and Movement Limiting Mechanism

In some embodiments, incorporating an automated tension control mechanism into a lead extraction sheath may increase ease of use and/or safety of the device. In some cases, applying the appropriate tension to the lead as the extraction sheath is inserted, manipulated, and/or activated, may be complex and/or require more than two hands. In some embodiments, an automated lead tensioning mechanism is supplied. Using an automatic lead tensioning mechanism may facilitate performance of the procedure by a single operator. Alternatively, or additionally, the lead tensioning mechanism provides increased control over the procedure. In some embodiments, an automated lead tensioning mechanism limits the tension to a level at which such complications (for example breakage of the lead and/or tearing of tissue) are less likely to occur.

Figure 15A:
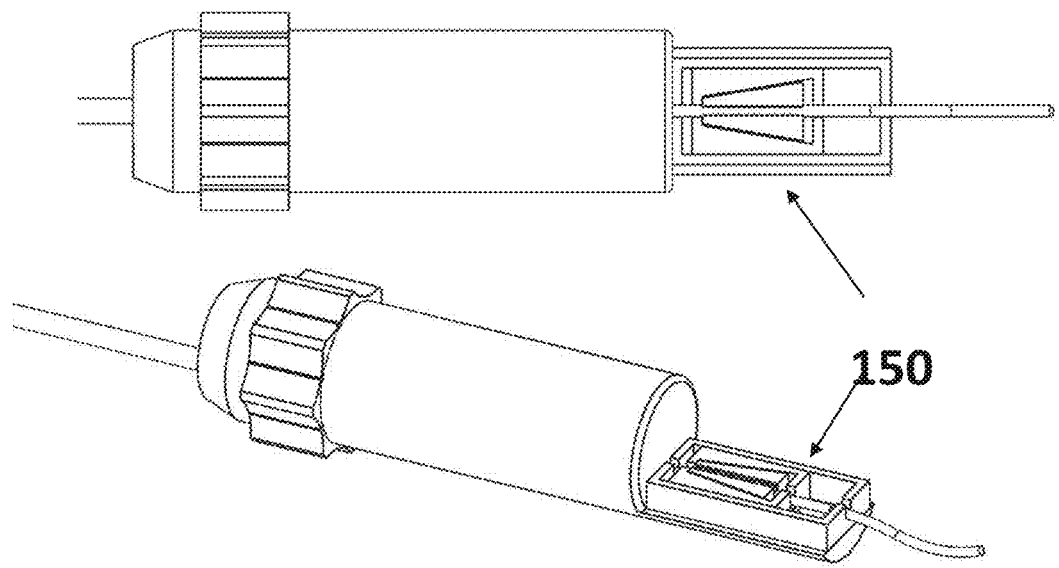
FIGS. 15a-e are schematic views of exemplary tension control and movement limiting mechanism, according to some embodiments of the present invention.
Figure 15B:
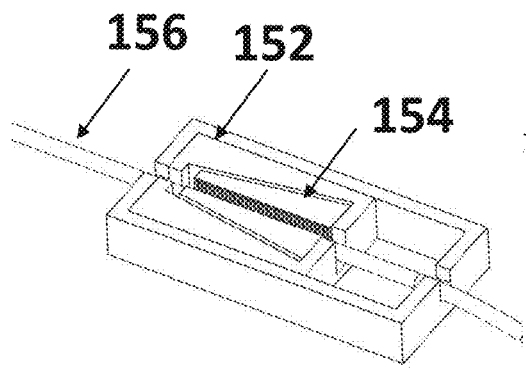
Figure 15C:
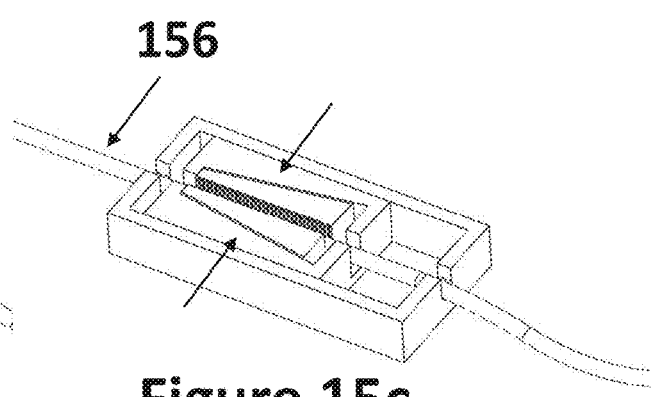
Figure 15D:
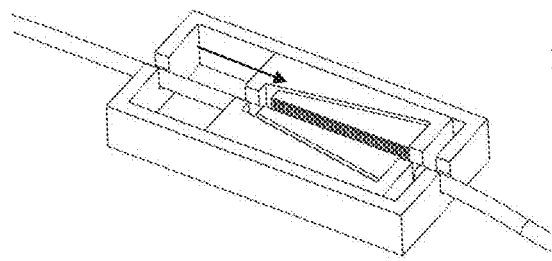
Figure 15E:
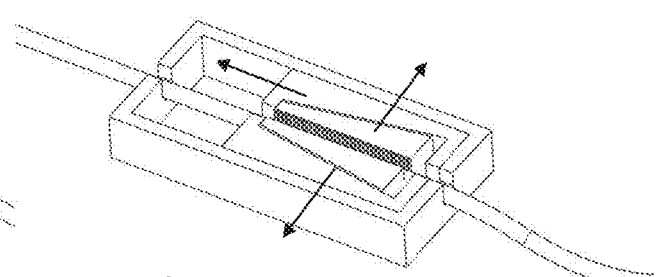

In some embodiments, the device handle includes an automated controlled lead tensioning mechanism 150, as shown for example in FIG. 15a (upper—top view, bottom—perspective view). Referring now to FIG. 15b, showing a schematic representation of the lead tensioning mechanism 150. In some embodiments, the lead tensioning mechanism 150 comprises a body 152, gripping teeth 154 and a motor (not shown) adapted to move the gripping teeth. Referring now to FIG. 15*c*, showing the gripping teeth sliding inwards in the direction of the arrows and gripping the lead 156. Referring now to FIG. 15*d*, showing the gripping teeth sliding back (proximally), following the arrow, and pulling the lead in the proximal direction. Referring now to FIG. 15*c*, showing the gripping teeth sliding outwards, following the arrows, and then sliding forwards (distally) to the initial position ready to re-engage the lead. Optionally, the automated controlled lead tensioning mechanism grasps a proximal portion of the lead. Optionally, the mechanism includes a locking stylet that applies a controlled tension to the lead in relation to the LE device. For example, the stylet pulls in the proximal direction. For example, the stylet maintains the lead in constant tension as the sheath is inserted, manipulated, and/or activated.

Another potential source of complications is uncontrolled movement of the lead, for example when the lead is under tension and abruptly freed. For example, this may result in the tension being suddenly applied to a new location in a vein or heart. Sudden changes in tension may result in a tear in a vein or heart wall. In some cases, this type of complication may result from elasticity of the lead and/or from the uncontrolled movement of a tension producing mechanism (for example the hand of the operator). For example, uncontrolled movement may occur under the sudden release of tension. In some embodiments, a locking stylet is used.

In some embodiments, the locking stylet reduces the elasticity of the system. In some cases, a locking stylet is used while manually holding the lead. In some cases, another possible complication may be the uncontrolled movement of the hand of the user. In some embodiments, the device includes a mechanism that limits the movement and/or the velocity of a lead and/or a stylet. The limitation mechanism is optionally independent of the tension applied. For example, the limiting mechanism prevents sudden movements. For example, sudden movements are prevented when a very high tension is applied and/or when the lead is suddenly released.

In some embodiments, the device includes a mechanism for limiting the movement and/or the velocity of the lead. Optionally, the limiting mechanism inhibits sudden movements of a stylet and/or lead. In some embodiments, the limiting mechanism includes a clamp that attaches to a stylet and/or lead. For example, the clamp may have a limited motion range and/or limited velocity.

6. Exemplary Characteristics of Force Measurements in the Device

In some embodiments, the LE device comprises elements which allow the sensing of force and/or pressure applied by the device tip and/or segments along the catheter length. In some embodiments, the basic approach common to all methods is the translation of the force or pressure applied by the device, into a mechanical displacement and/or material deformation, which is translated to a sensible signal that is captured and processed to provide force or pressure indication. In some embodiments, the methods provide indication on force applied in 1, 2 or 3 dimensions. In some embodiments, the dimensions may be independent or relative to the axes of the catheter position.

6.1 Exemplary Force Transducer in the Distal Portion of the Device

In some embodiments, the device comprises a force sensor. For example, the sensor may include an axial force sensor, which measures the force that the device is exerting in the distal direction upon tissue, for example at the distal tip of the device. In some cases, difficulties in performing lead extraction are due to variable and/or unknown flexibility and/or friction along the path that the lead extraction device takes from the user's hands to the distal tip. These factors may make it difficult to judge the amount of force that the distal tip is applying on the tissue based on the force being applied by the user. In some embodiments, a force sensor near the distal tip of the device provides information about the amount of force being applied by the distal portion of the device on the tissue. In some embodiments, this information aids in the safe and effective performance of the lead extraction procedure.

In some embodiments, the force sensor is comprised of a mechanically weakened region of the wall of the shaft of the device and/or a sensor, which senses the force-dependent distortion of the wall of the shaft of the device near the weakened region. In some embodiments, the weakened region includes cuts in the wall of the shaft of the device. In some embodiments, the sensor includes a strain gauge.

6.2 Exemplary Model and Shape Based Force Estimation

Figure 15F:
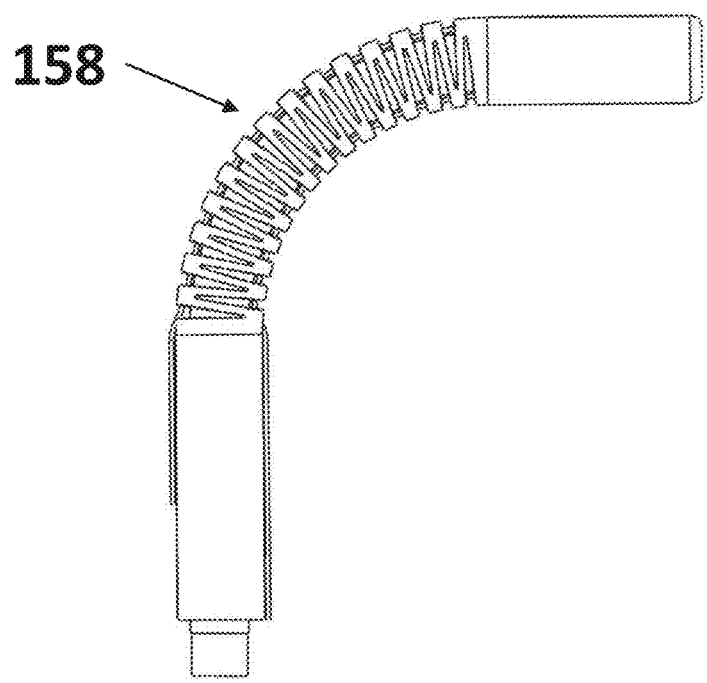
FIGS. 15f-g are schematic views of exemplary articulated structures intended for catheter steering, according to some embodiments of the present invention.
Figure 15G:
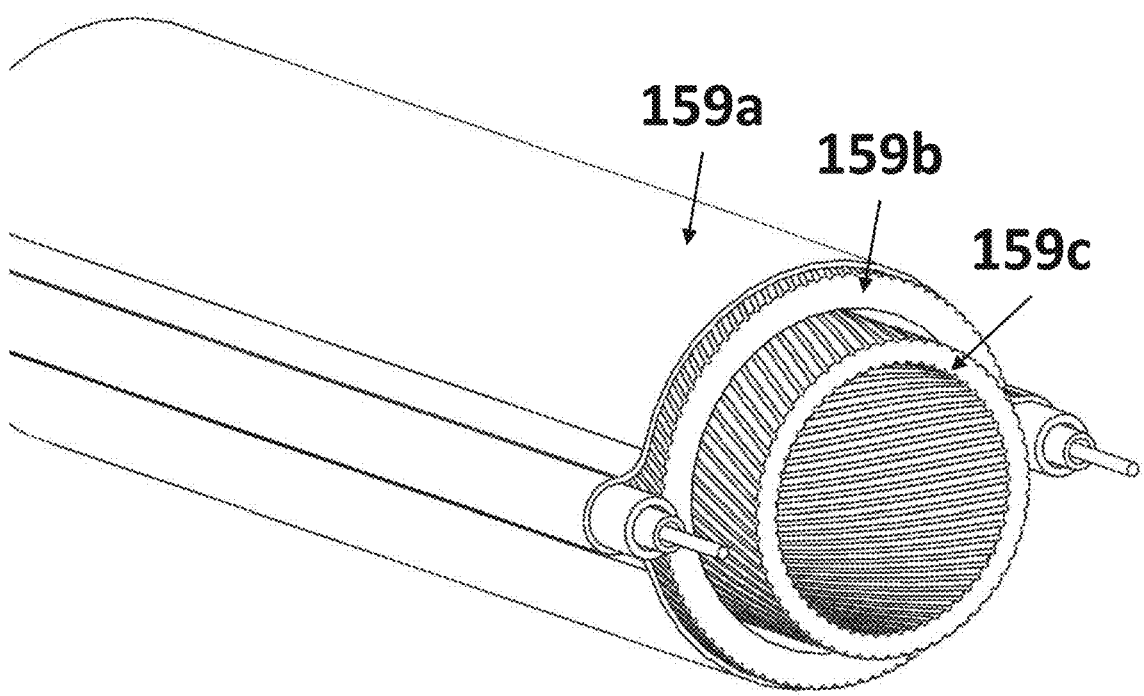

In some embodiments, the estimation of forces applied by the LE device is performed without the need for integration of sensors on the device itself or any other device add-on (such as an additional outer sheath). In some embodiments, the estimation of forces is performed by the activation of an external imaging or tracking system to track the shape and position of catheter inside the body. In some embodiments, for example, such a system, which is also in common use in LE procedures, is the X-RAY system, used for tracking and navigation of the device inside the body. In some embodiments, access to the raw data of the X-RAY machine provides the necessary and sufficient data for this method. In some embodiments, radio opaque markers may be incorporated along the length of the LE device for easier and more accurate extraction of data on the catheter's shape. In some embodiments, a force displacement model is developed per each LE device type intended to be used with this method. In some embodiments, the force estimation is performed by force-displacement modeling of special mechanical structures within the device such as: an articulated structure that is intended for catheter steering (see FIG. 15*f*-Articulated structure 158 of an LE catheter) or a multi-luminal structure designed for instance to support rotational force transfer from the proximal end of the catheter to distal end (see FIG. 15*g*-Multi-luminal structure 159*a-c* (lumens) of a LE catheter). In some embodiments, the model allows for a shape-based force estimation equation to be solved, with real-time coordinates of the catheter as inputs, for the force applied by the tip or by every point along the length of the catheter.

6.3 Exemplary Opto-Mechanical Methods

In some embodiments, opto-mechanical methods for force and/or pressure estimation are used and may have the advantage of being free of electrical currents inside the patient's cardiovascular system and hence are possibly safer than electro-mechanical methods. In some embodiments, in addition, sensing is not influenced by electromagnetic fields or RF power that may exist in the environment.

In some embodiments, laser LE devices are based on catheter advancement through binding sites, by laser ablation, where light is emitted on the target by an array of optical-fibers. In some embodiments, for such devices, opto-mechanical methods for force sensing at the distal end of the device are based on taking up some fibers from the array and using them for force sensing, for example, in one of the methods described below.

6.3.1 Exemplary Optical Methods Based on Reflective Intensity of Light

In some embodiments, light is transmitted at a reflector and the reflected light intensity is modulated by the applied force, using a mechanical force-to-displacement translation unit, such as a flexure, a diaphragm or similar.

Figure 16:
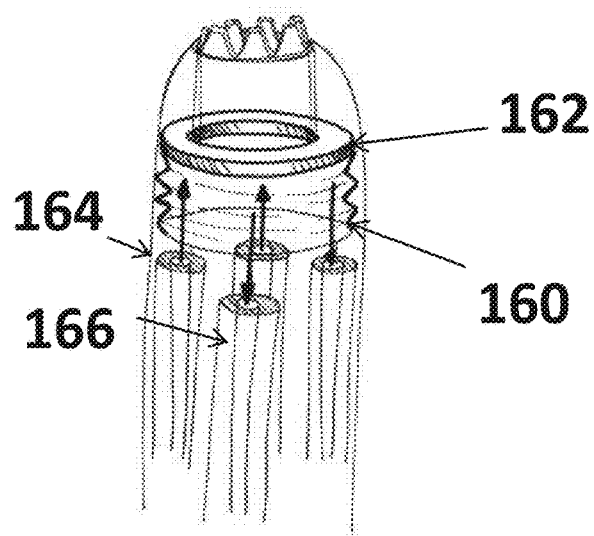
FIG. 16 is a schematic view of an exemplary optomechanical tool located at the distal head, according to some embodiments of the present invention.

In some embodiments, a flexure 160 is used to convert force to displacement, to be sensed by light reflectance. In some embodiments, the flexure is an integral part of the catheter head, as shown in FIG. 16. In some embodiments, the flexure 160 is structured within the articulated structure designed for a steering capacity, in a steerable catheter. In some embodiments, the flexure 160 is part of an add-on sheath, separated from the LE device. In some embodiments, the flexure 160 holds a reflecting structure—the reflector 162, designed to enable force sensing, with no interference to the penetrating mechanism of the catheter head. In some embodiments, the reflector is shaped as a ring 162, positioned above the tips of the light transmission medium, as shown for example, in FIG. 16. In some embodiments, light is transmitted along the length of the catheter by a single or a multiple of optical fibers 164, and is emitted towards the reflector 162. In some embodiments, a single or multiple of optical fibers 166 are used to receive the reflected light, and carry it to a control unit outside the body. In some embodiments, the control unit includes the light source of the transmitting fibers, and a reception sub-unit in charge of translation of light intensity into force indication.

Figure 17A:
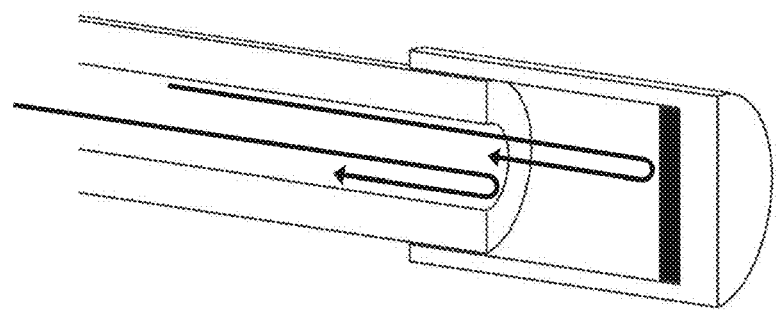
FIGS. 17a-b are schematic views of an exemplary optomechanical tool located at the distal head, according to some embodiments of the present invention.
Figure 17B:
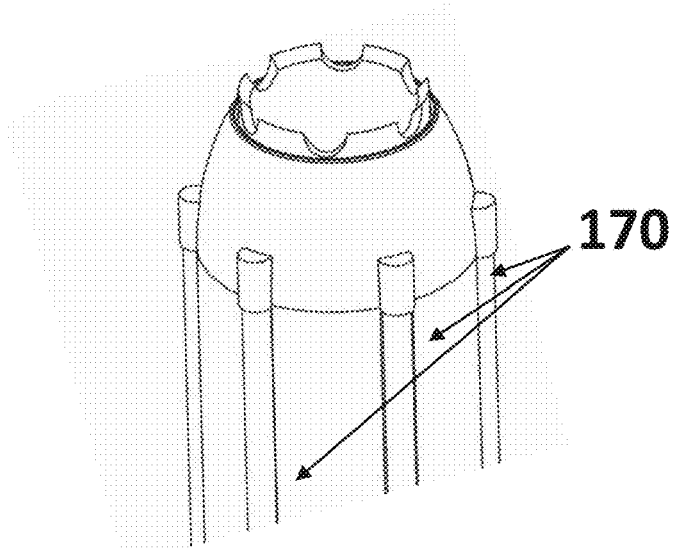

In some embodiments, light interference patterns are sensed by a Fabry-Perot interferometer, based on the principle of interferometry. In some embodiments, a single fiber is used for transmission of emitted and reflected light. In some embodiments, a cavity is located on the tip of a single-mode optical fiber and enclosed by a miniature glass diaphragm. In some embodiments, light is reflected both from the end face of the fiber and from the diaphragm. In some embodiments, the two reflected signals interfere with each other and have a phase difference, as shown for example in FIG. 17a (Illustration of the Fabry-Perot effect), since light from the diaphragm has traveled an extra distance through the cavity. In some embodiments, the phase difference depends on the diaphragm distance from the fiber tip. In some embodiments, the intensity of the light penetrating back into the fiber is a function of the phase difference between the interfering signals and hence related to the diaphragm displacement resulting from pressure applied on it. In some embodiments, a single fiber with a cavity and diaphragm is used. In some embodiments, multiple of fibers 170 are used to sense forces in multiple directions and orientations, as shown for example in FIG. 17b (Exemplary optical force sensor based on Fabry Perot interferometer, embedded on LE device). In some embodiments, a control unit is in charge of providing the light source for emission and for receiving the Fabry-Perot interference signal and deducting force indications based on the intensity.

6.3.2 Exemplary Fiber Bragg Grating Methods Based on Wavelength Shift

In some embodiments, Fiber Bragg Grating (FBG) structure is constructed by creating a periodic variation in the refractive index of the fiber core. In some embodiments, when created in a short segment of an optical fiber, FBG reflects particular wavelength and transmits all the others and therefore can be used as an inline optical filter. In some embodiments, the wavelength at which high reflectivity occurs is determined by the periodicity of the gratings. In some embodiments, when the FBG segment in the fiber is stretched or compressed, the dimensions of the grated area are shifted, resulting in a shift in the reflected wavelength. In some embodiments, this property is used for sensing the pressure applied on the fiber.

Figure 18A:
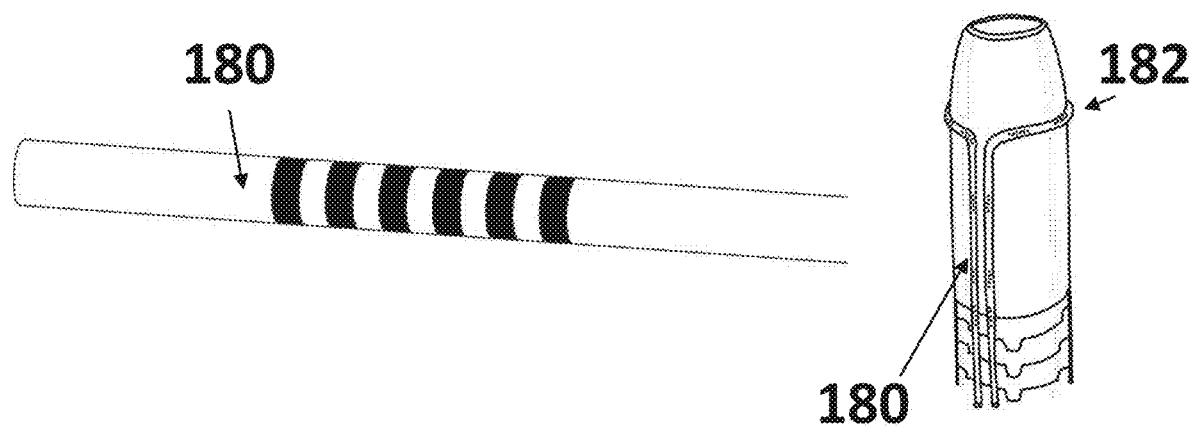
FIGS. 18a-b are schematic views of an exemplary optomechanical tool located at the distal head, according to some embodiments of the present invention.
Figure 18B:
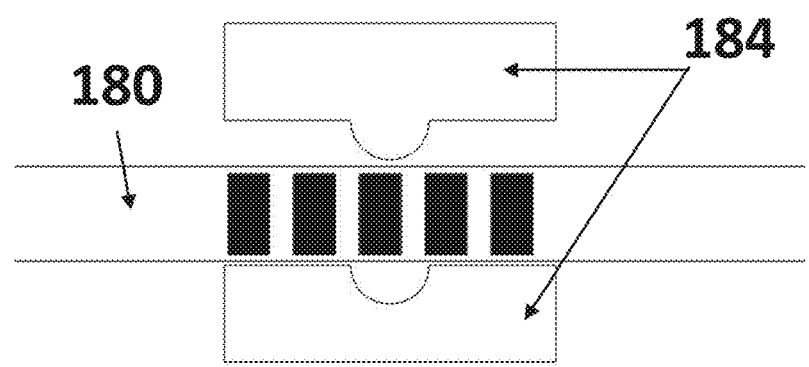

In some embodiments, FBG sensors are integrated on the device. In some embodiments, an optical fiber embedded with FBG segments 180 is spread along the length of the catheter and wrapped in a ring shape 182 around the device head. In some embodiments, each FBG segmented is formed to reflect a different wavelength, this way frequency analysis of the reflected and transmitted signals at a control unit can estimate the forces sensed at different locations along the length and around the head of the device, as shown for example in FIG. 18a (FBG segmented fiber integrated in an LE device.). In some embodiments, for the FBG segments along the length of the catheter, bending and deformation as a result of contact and friction with the blood vessel wall, are translated directly to a wavelength shift that can be sensed. In some embodiments, for the ring shaped section, wrapping the head of the catheter, a mechanical unit for the translation of longitudinal forces to FBG segment strain or bending, might be needed. In some embodiments, for example, a mechanical structure composed of a top circular plane with protuberances 184 positioned above the FBG segments in the fiber ring and bottom circular plane with sockets located straight under the FBG segments and the protuberances, as shown for example in FIG. 18b (Force to FBG bending mechanical translation unit.). In some embodiments, such structure allows for forces on the head of the catheter to translate into FBG segment bending and therefore to a reflected wavelength shift.

In some embodiments, the measurement of the shift in the reflected wavelength is performed, for example, by laser interferometry. In some embodiments, the sensor mounted in the LE device produces a signal with a wavelength varying depending on the stress acting on the device. In some embodiments, this signal is compared to a nearly-identical sensor that is left outside and/or inside the catheter in a part that do not deforms, in an external analysis unit. In some embodiments, when the LE device is not under any strain, both sensors provide a nearly identical wavelength. In some embodiments, this is calibrated as the reading "zero".

In some embodiments, when the LE device sensor experiences any stress, its wavelength shifts and this is measured by the interferometer.

Figure 19A:
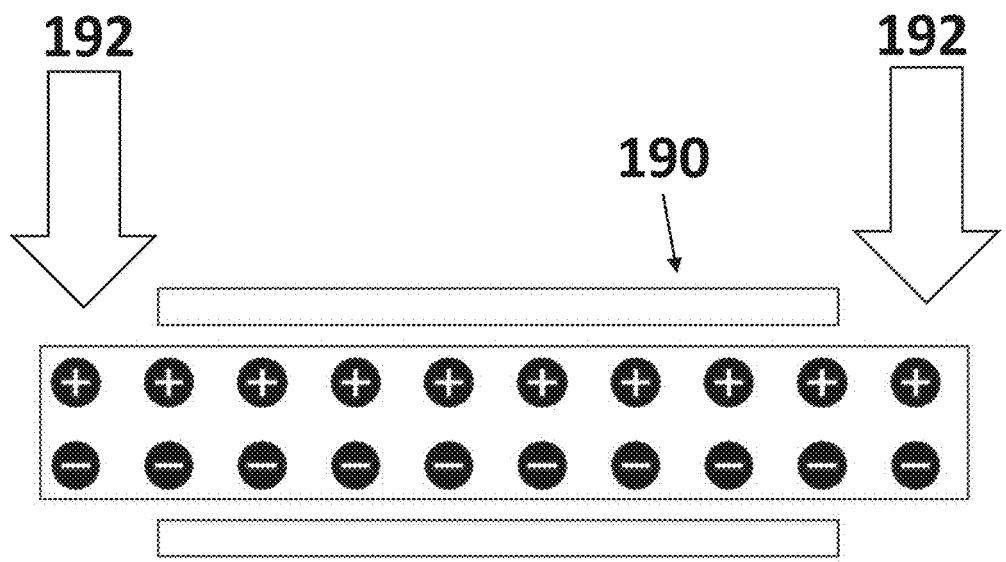
FIGS. 19a-b are schematic views of an exemplary electromechanical tool located at the distal head, according to some embodiments of the present invention.

6.4 Exemplary Electro-Mechanical Methods
6.4.1 Exemplary PVDF Force Sensing Polyvinylidene Difluoride (PVDF) is a chemically stable piezoelectric polymer with high piezoelectric properties. PVDF films have been used as force sensors in various applications. When a load is applied on the top of a PVDF film 190, the polymer accumulates electric charge on both sides of the material, which has equal number and opposite polarity. This charge is proportional to the applied force 192 and can be sensed electrically, as shown for example in FIG. 19a (Piezoelectric principle in PVDF).

Figure 19B:
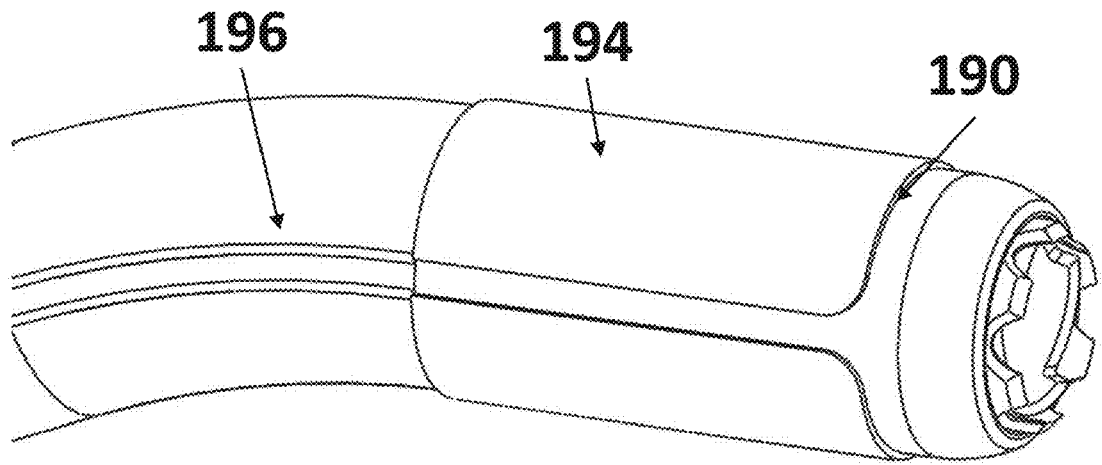

In some embodiments, PVDF film segments are used to wrap parts of the catheter where force sensing is desirable, for instance: the LE device head, for the purpose of spatially continuous sensing of force in all directions. In some embodiments, the PVDF sensor is composed of PVDF film 190, an outer coating of insulated and damp proof rubber film 194 and 2 conductive wires 196 attached to electrodes on both sides of the PVDF film. In some embodiments, the wires are spread along the catheter length and serve as inputs to a control unit, where measured voltage is analyzed and translated to force indication, as shown for example in FIG. 19b.

6.4.2 Exemplary Capacitive-Inductive Force Sensing

An electric circuit made up of a capacitor and an inductor is called an LC circuit, and is characterized by a resonance phenomenon at a frequency Fr=1/[2pi*sqrt(L*C)], with L being the inductance in Henry, and C being the capacitance in Farad.

In some embodiments, such a design is used as a pressure sensor, when the capacitor is made up from two electrode plates with a soft dielectric material between them. In some embodiments, when an electrode plate is pressed, the capacitance increases and with it the resonance frequency of the circuit.

Figure 20A:
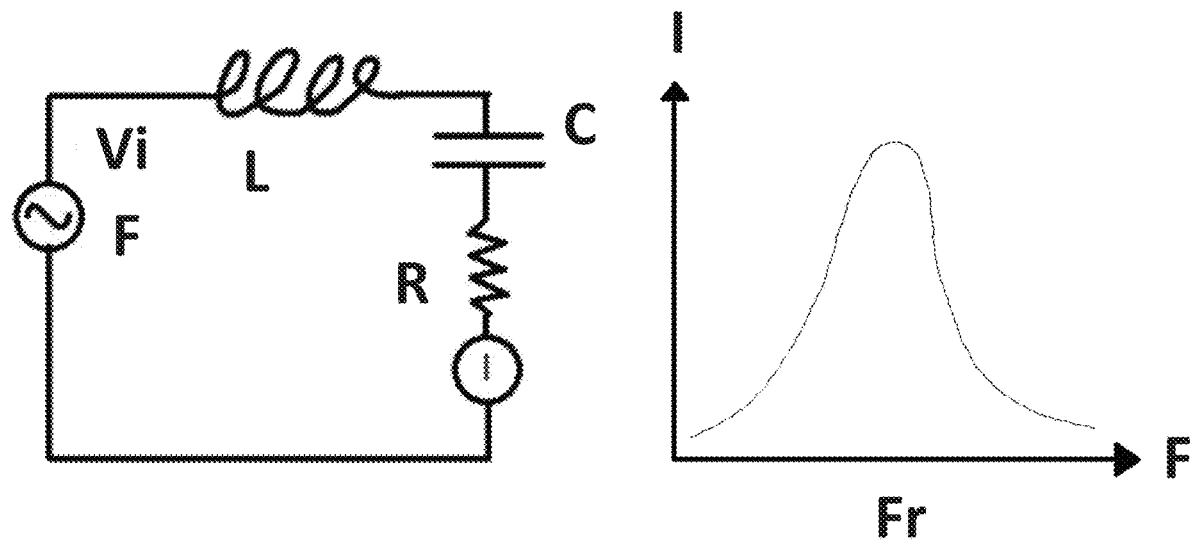
FIGS. 20a-b are schematic figures related to capacitive-inductive force sensing, according to some embodiments of the present invention.

In some embodiments, if the circuit is driven at a frequency f close to the resonance frequency, and the transmitted amplitude is measured, then it is highly sensitive to a change in resonance frequency, as shown for example in FIG. 20a.

$$i=Vi/\text{sqrt}[R^2+(wL-1/wC)^2]$$

$$w=2*pi*f$$

Figure 20B:
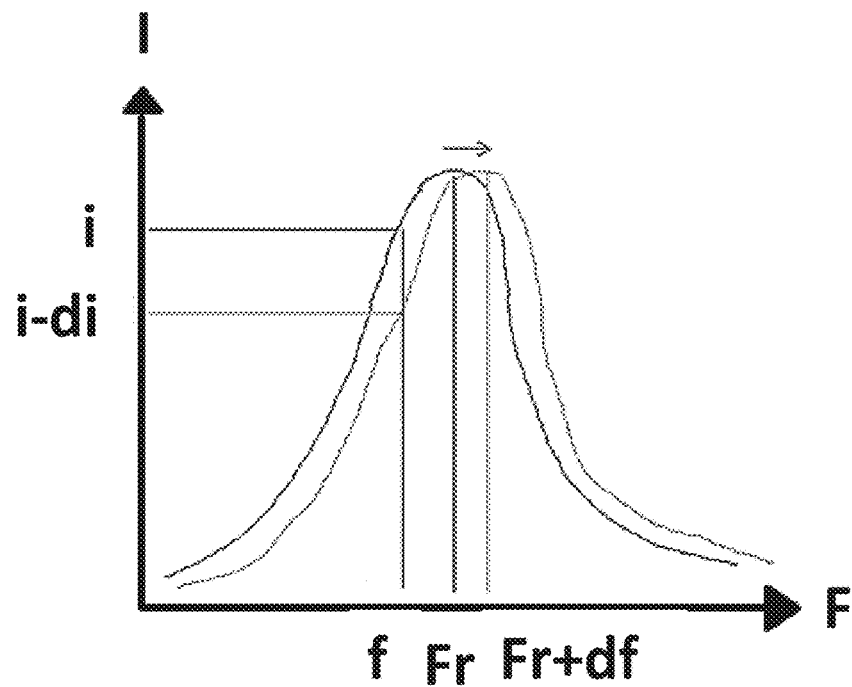

In some embodiments, when the capacitance changes, the resonance frequency shifts. As a result, the attenuation of the signal at frequency f changes. In the example in FIG. 20b, the electric current decreases (if the capacitance increases and f<Fr).

In some embodiments, the circuit can be very sensitive to a change in current, if the quality factor is high (the parasitic resistance low).

Figure 21:
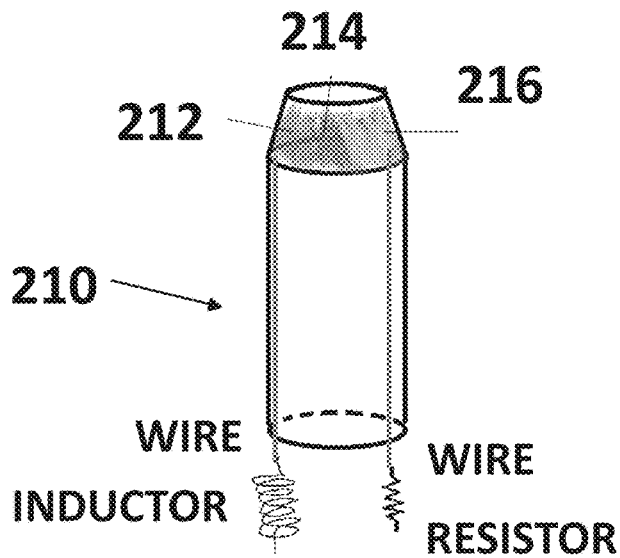
FIG. 21 is a schematic view of an exemplary LC based force sensor, according to some embodiments of the present invention.

In some embodiments, an LC based force sensor is integrated in the device. In some embodiments, current is measured by a 4-wire current probe, using a series resistance low enough not to disrupt the quality factor of the circuit too much. In some embodiments, for use on a catheter, the sensor 210 is made up of an inner electrode 212, thin and soft dielectric foam 214, and an outer electrode 216, as shown for example in FIG. 21.

In some embodiments, the electrodes are connected by wires to the catheter handle, were the inductor and 4-wire current probe resistor are located. In some embodiments, the electrodes are located along the sides of the tip, along the length of the shaft, as patches on a hinge (see FIG. 19b) or any other location on the exterior of the catheter. In some embodiments, a sensor may also be located in the interior of the device, as a reference sensor against which the external sensors' signal can be compared (in an electronic differential manner).

In some embodiments, force is sensed by the capacitive-inductive resonance method described above and shift in resonance is detected and measured wirelessly, through resonant inductive coupling. In some embodiments, the sensor circuit is made up of a small capacitor as described above, with the inductor arrayed next to it or around it. In some embodiments, there are no wires connected to it.

Figure 22A:
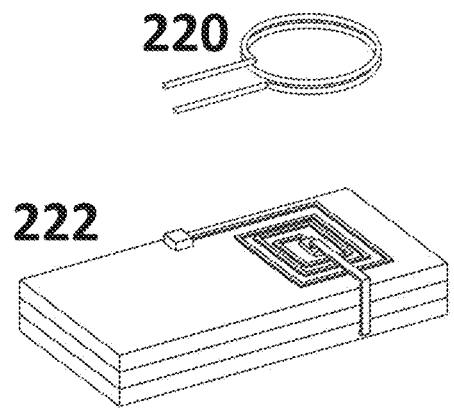
FIGS. 22a-b are schematic figures related to exemplary sensors, according to some embodiments of the present invention.
Figure 22B:
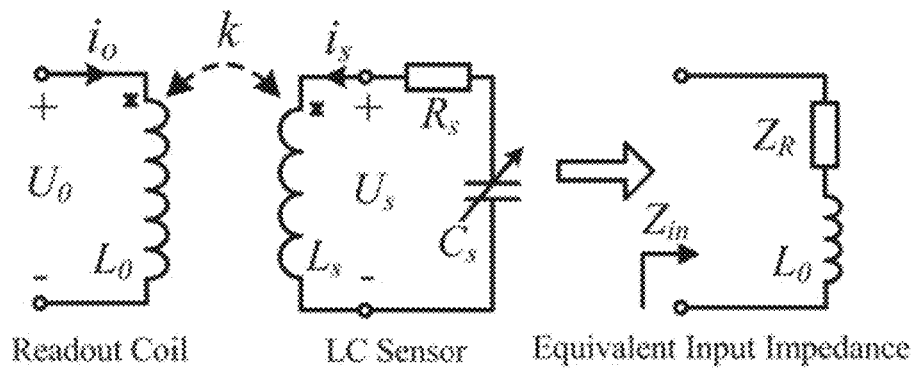

In some embodiments, the sensor is probed by an external read-out coil 220, inductively coupled to the sensor inductor, as shown for example in FIG. 22a-b. In some embodiments, the effective impedance of the readout coil is affected by the resonance frequency of the sensor circuit.

In some embodiments the readout coil 220 is positioned externally to the patient, and the LC pressure sensor 222 is integrated as part of the LE device. In some embodiments, the capacitor dielectric material is soft and compressible, thus when it is pressed the capacitance increases. In some embodiments, the coil is insulated from the adjacent capacitor plate.

6.5 Force Analysis Unit—Exemplary Feature

In some embodiments, in each one the force sensing methods, an external control and analysis unit that processes the received optical or electrical signal and produces a force indication for the user is included.

In some embodiments, the analysis unit comprises an algorithmic signal processing capacity to filter out measurement noises and artifacts produced by any mechanical feature of the device such as: a motorized mechanism, cutting head rotation, inner lumen periodic friction etc. In some embodiments, such signal processing algorithmic capacity considers spectral and temporal properties of the device activation mechanism and reduces their impact on the quality of the force measurement, by algorithmic methods such as time domain windowing or frequency domain filtering.

6.6 Lead Centering Detection Unit—Exemplary Feature

In some situations, the physician requires to understand the 3D orientation of the lead, of the vein and of the device, in order to determine how to rotate and steer the lead extraction device in the most effective manner and in a manner that is safe to the veins, such that the forces or energy is not aggressively applied to the vein wall. In some embodiments, the device comprises a sensor which monitors the tissue type or content of matter in different orientations of the tip (e.g. right-left, up/down in the steering orientations). In some embodiments, the device comprises a sensor that displays the lead orientation relative to the center of the lumen of the device, e.g. whether the lead is in the center, or trending towards the right or left side of the catheter, or towards the up (outer curve) or down (inner curve) of the steerable segment. In some embodiments, the information provided by the lead centering detection unit, may be used by the physician to decide to turn the catheter in the direction of the lead, and preferably away from the venous wall.

7. Handle of the Device and Motion

7.1 Exemplary Linear/Hammer Motion of a LE Device

In some embodiments, the LE device comprises an impact generator to provide pulsating strokes at the distal end of the LE device. In some embodiments, the mechanical part provides an additional rotation movement for the cutting, spreading and hammering tip. In some embodiments, the mechanical part enables a controlled, linear movement of blades in a forward-backward (distally-proximally) manner. In some embodiments, the movement of the blades provides a precise and controlled cutting of the tissue in front of the distal end of the LE device. In some embodiments, the linear motion mechanism is a motorized mechanism. In some embodiments, the motorized mechanism is activated by a controller on the handle of the LE device. In some embodiments, the motorized mechanism is activated by a dedicated pedal (or similar mechanism) located in close proximity to the user. In some embodiments, motion mechanisms are divided between the handle of the device and an adjacent unit. In some embodiments, all the motion mechanisms are located outside the handle and they are delivered into the handle from an external connector. In some embodiments, for linear or for radial LE device the speed of the motor can be in the range from about 1 Hz to about 100 Hz for example, and/or from about 1 Hz to about 100 Hz, and/or from about 20 Hz to about 70 Hz, and/or from about 15 Hz to about 80 Hz, and/or from about 10 Hz to about 80 Hz, and/or from about 3 Hz to about 90 Hz, and/or from about 35 Hz to about 60 Hz, and/or from about 1 Hz to about 15 Hz.

In some embodiments, a pedal or a button in the handle activates the linear motion mechanism in an on/off manner or PWM controlled (speed controlled). In some embodiments, a pedal or a button in the handle activates the linear motion mechanism in an incremental motion controlled manner. In some embodiments, a pedal or a button in the handle activates the linear motion mechanism using pneumatic mechanism. In some embodiments, the movement of the blades created by the linear motion mechanism is performed mainly inside the LE device (i.e.: internally—without an external manifestation of the movement) and at the end of the forward cycle the blades protrude from the distal end of the LE device. In some embodiments, the linear motion motor mechanism is located at the LE device's handle. In some embodiments, the linear motion motor mechanism is located outside the LE device. In some embodiments, the linear movement of the cutting mechanism is performed inside the LE device/catheter, therefore protected from the outside environment of the LE device. In some embodiments, the linear movement comprises a catheter structure as shown for example in FIG. 23e, and/or is done with a multilumen sheath or Fort Wayne HHS® or similar material that provides the bending radius/torque/pushability parameters or a combination of materials.

Figure 23A:
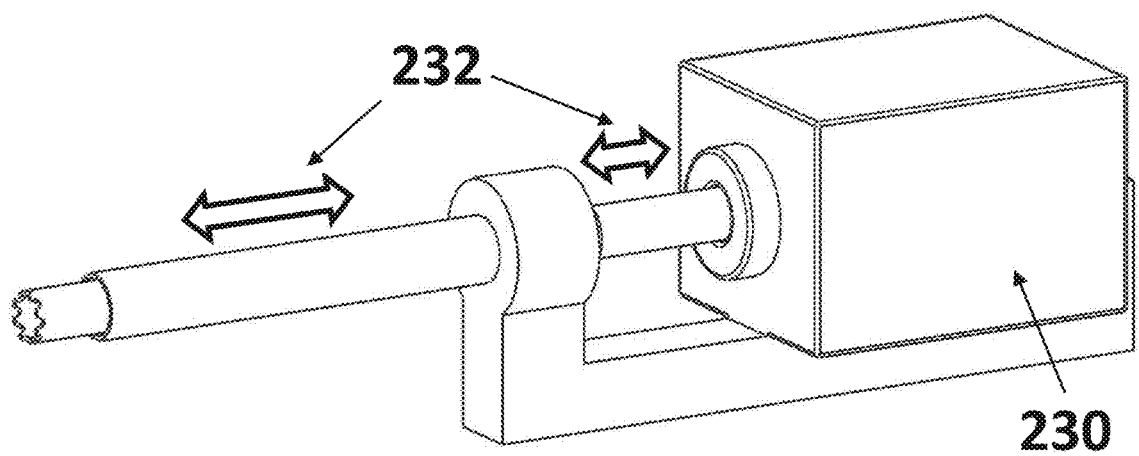
FIGS. 23a-e are schematic views of an exemplary mechanism located at the handle, according to some embodiments of the present invention.
Figure 23B:
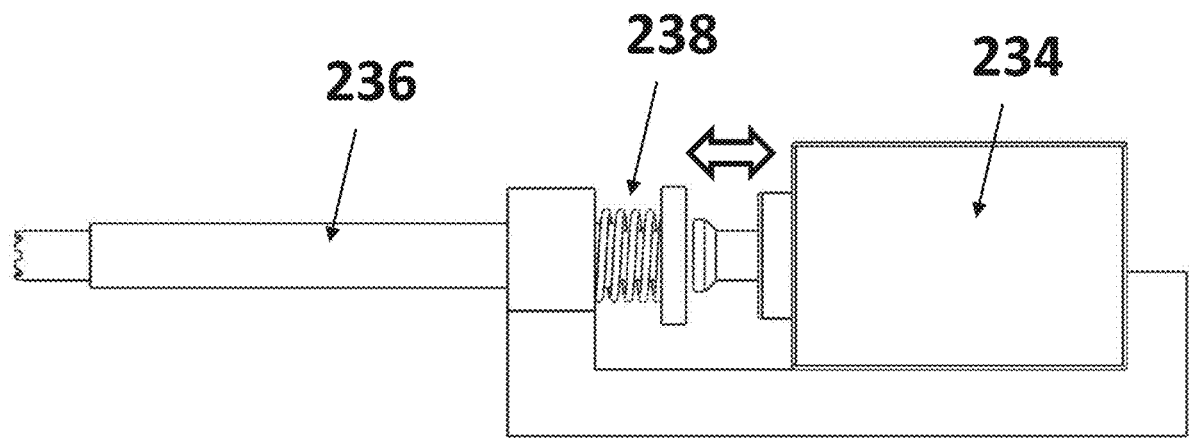
Figure 23C:
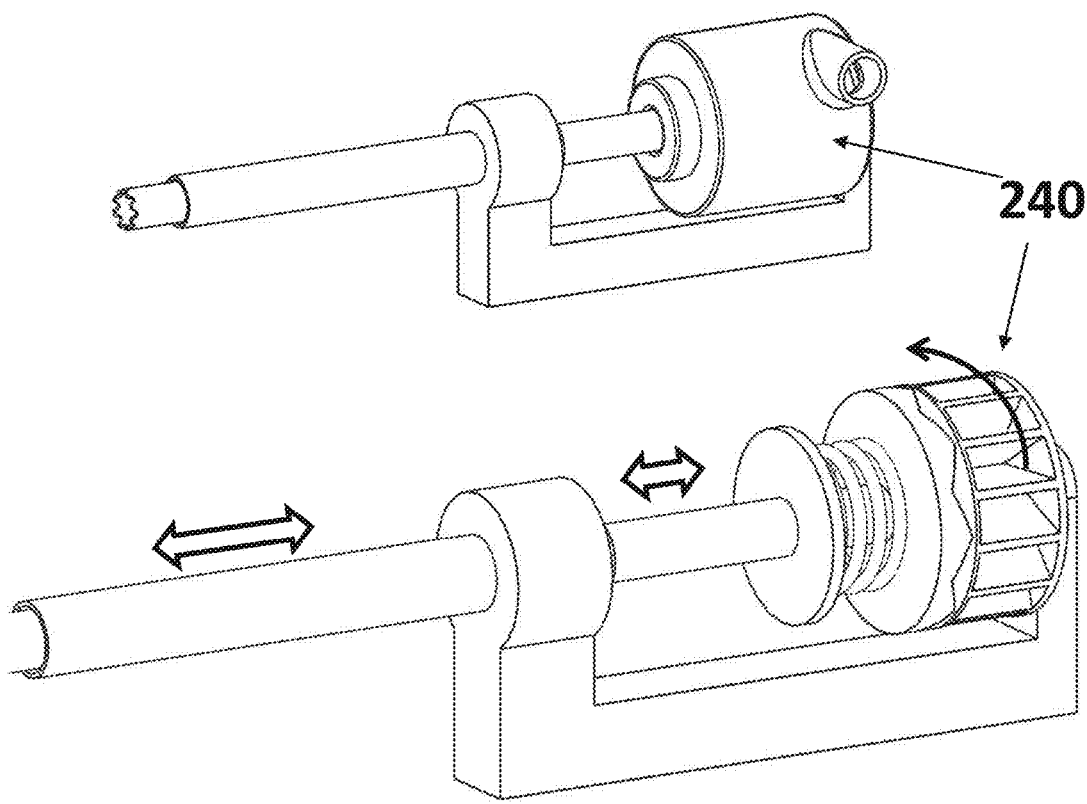

Several possibilities of linear motion mechanisms are shown, for example, in FIGS. 23a-c. As shown in FIG. 23a, the linear motion is created by a motor 230 inside the box and transduced into linear motion 232. FIG. 23b shows an example of a motor 234 which pushes the central shaft core 236, which is adapted to return due to the spring 238. FIG. 23c shows an example of a device in which an external source of energy (not shown) rotates a gear engine 240. The gear engine transforms rotational motion into linear motion.

Figure 23D:
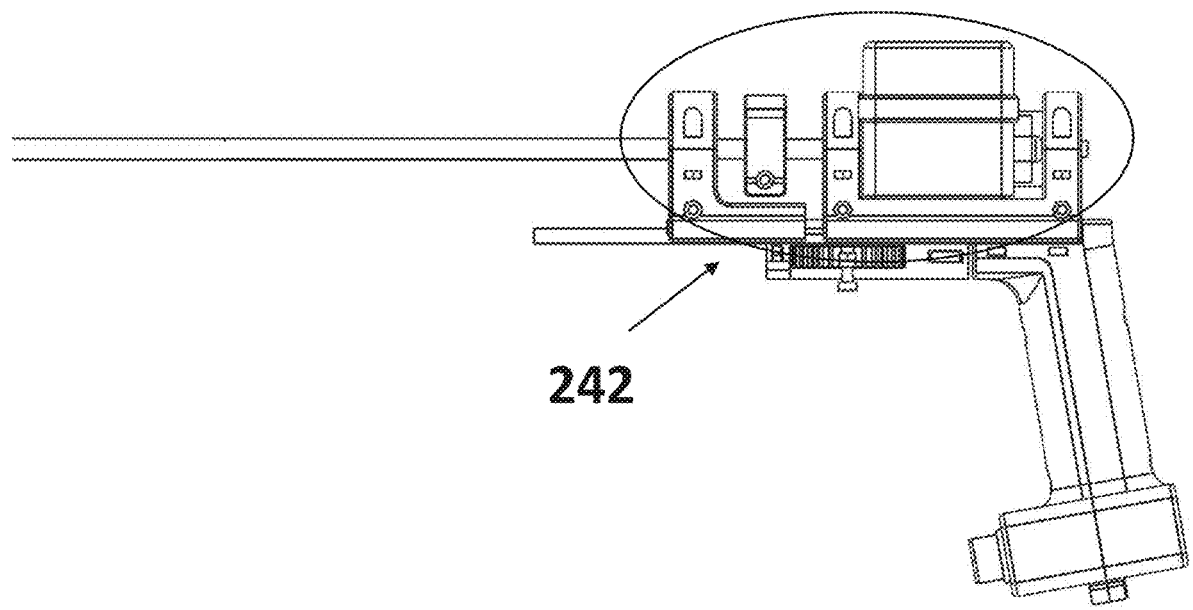
Figure 23E:
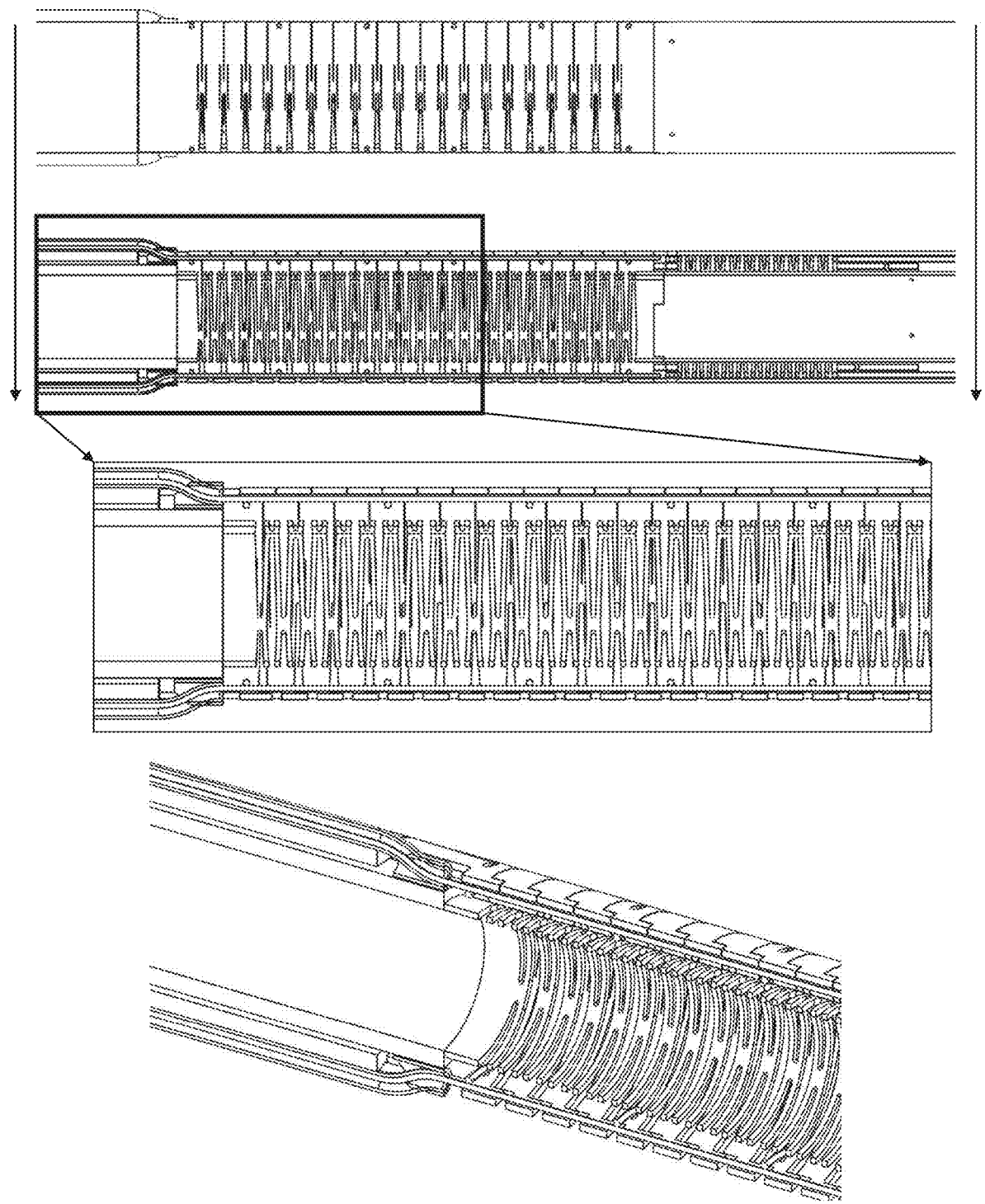

In some embodiments, the motion mechanisms 242 (circled) are incorporated into the handle as shown, for example in FIG. 23d.

7.2 Exemplary Dual Motion Cutting Mechanism—Rotating Hammer

Figure 24A:
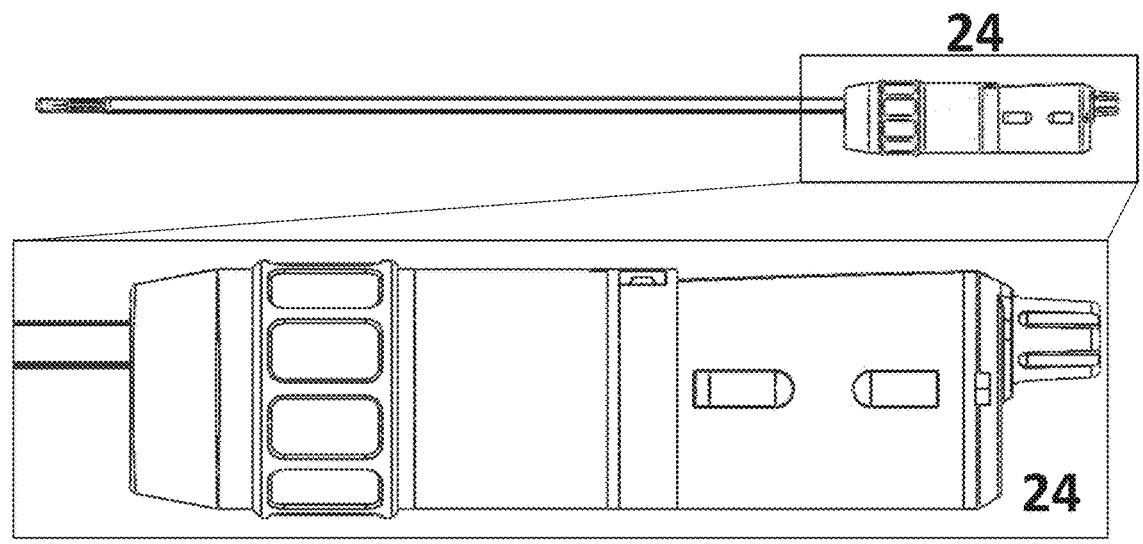
FIGS. 24a-d are schematic views of exemplary mechanisms located at the handle, according to some embodiments of the present invention.
Figure 24A:
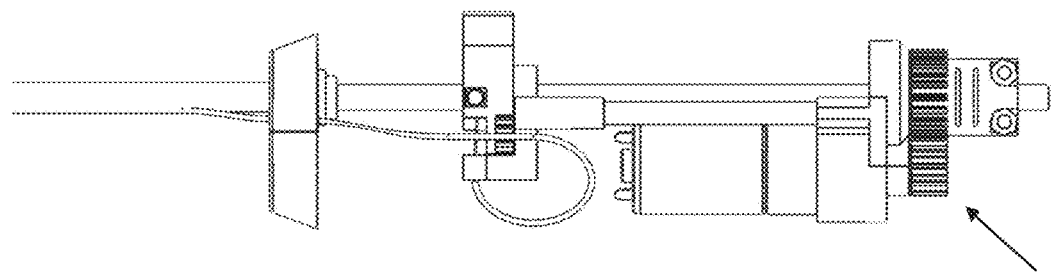
Figure 24B:
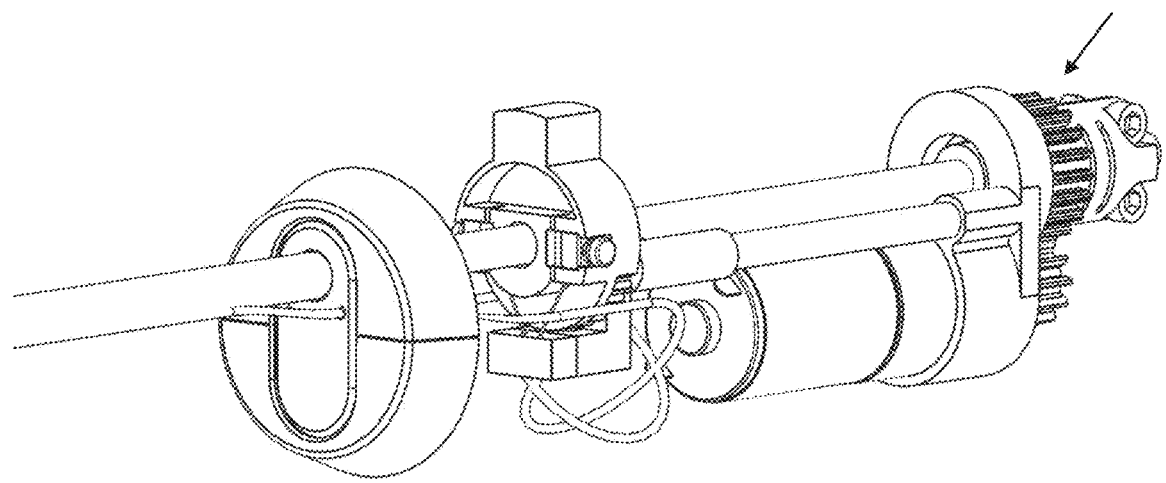
Figure 24C:
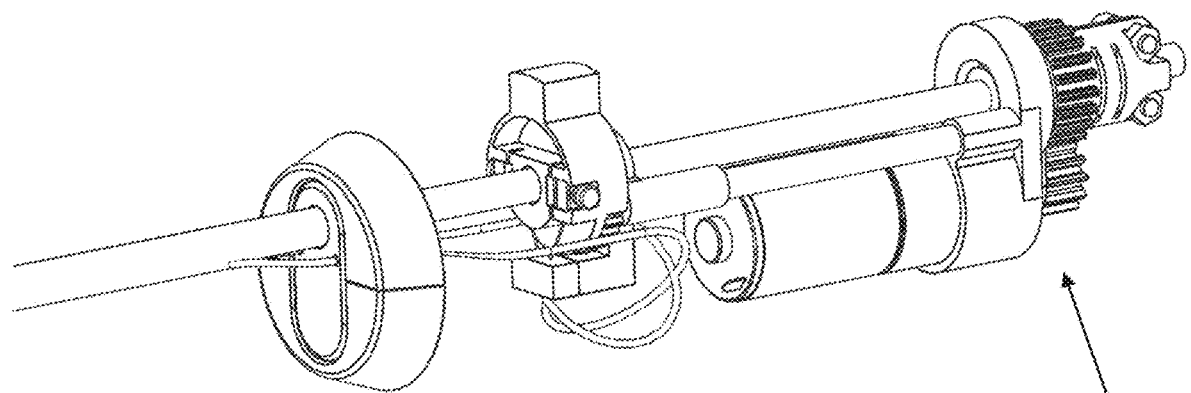
Figure 24D:
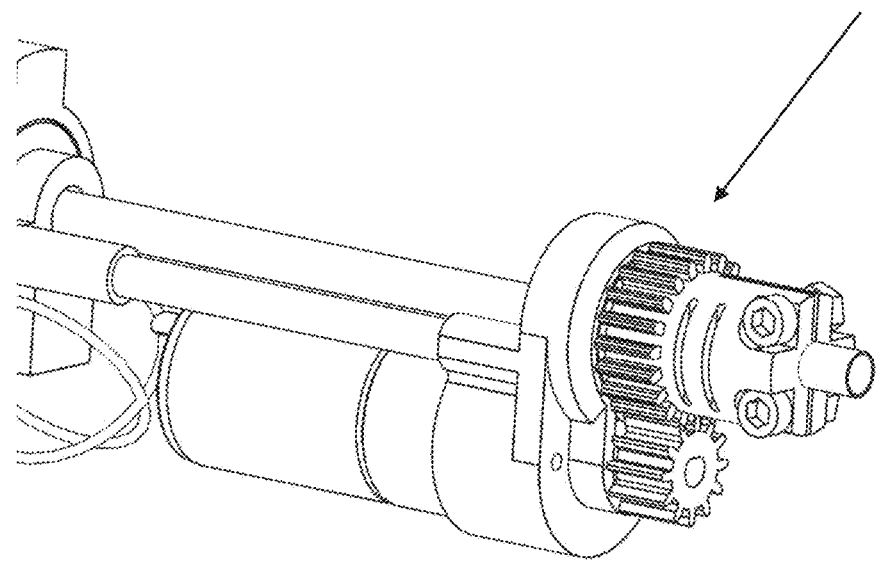
Figure 24E:
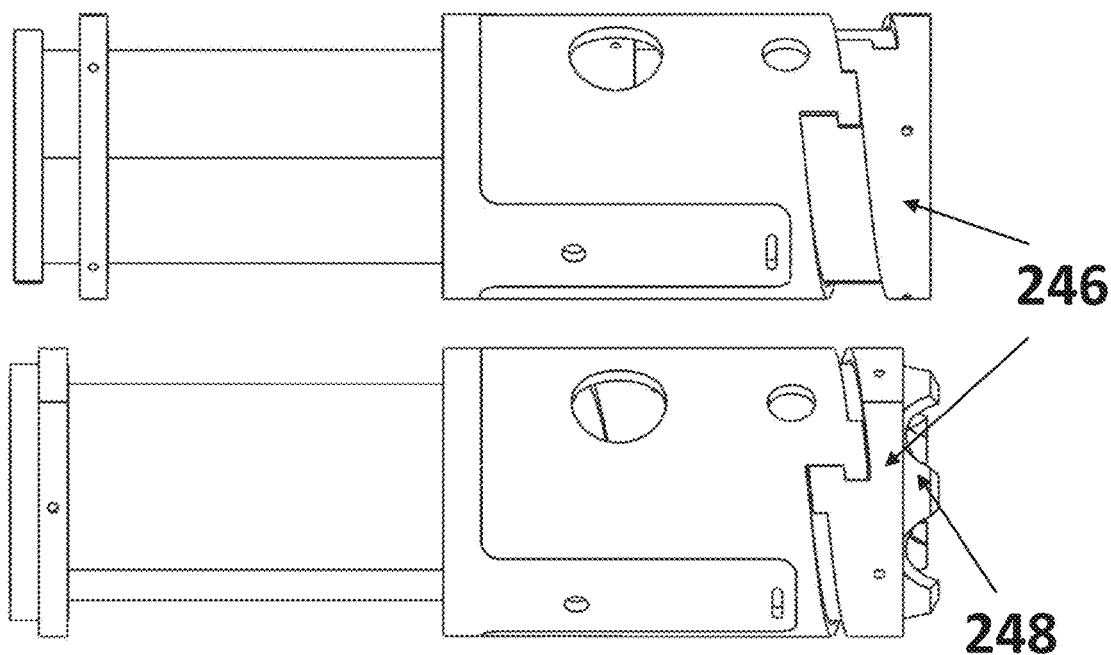
FIGS. 24e-r are schematic views of exemplary mechanisms located at the distal head, according to some embodiments of the present invention.
Figure 24F:
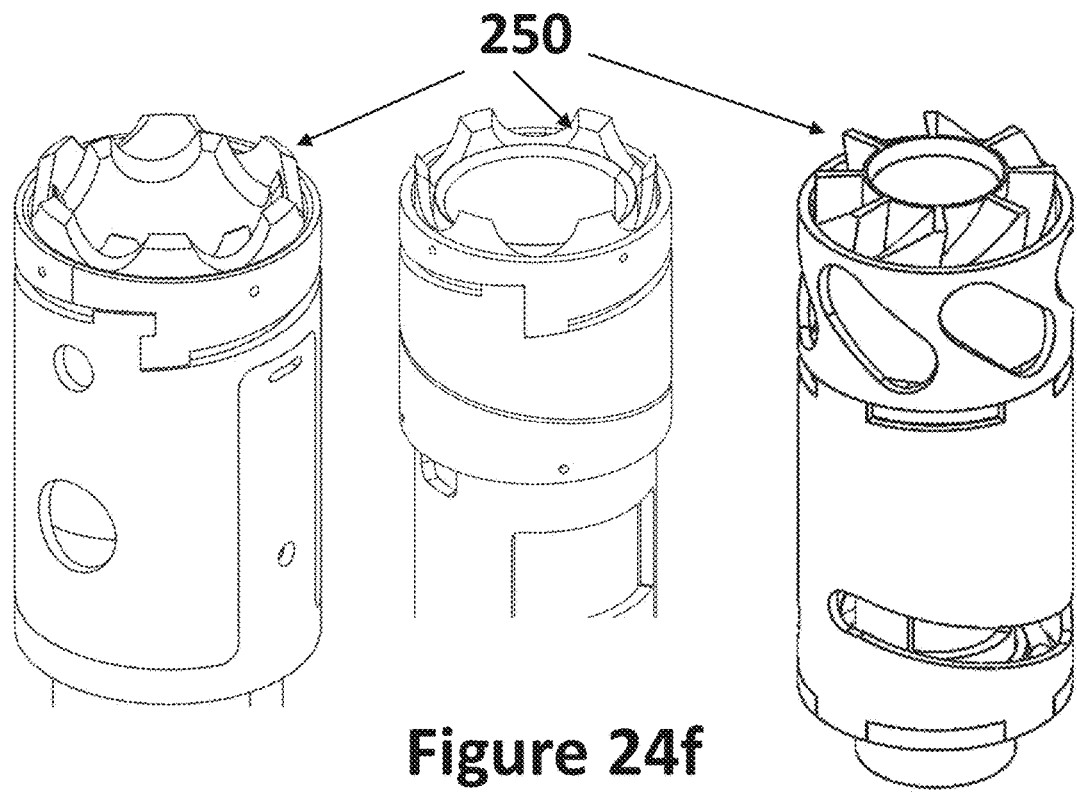
Figure 24G:
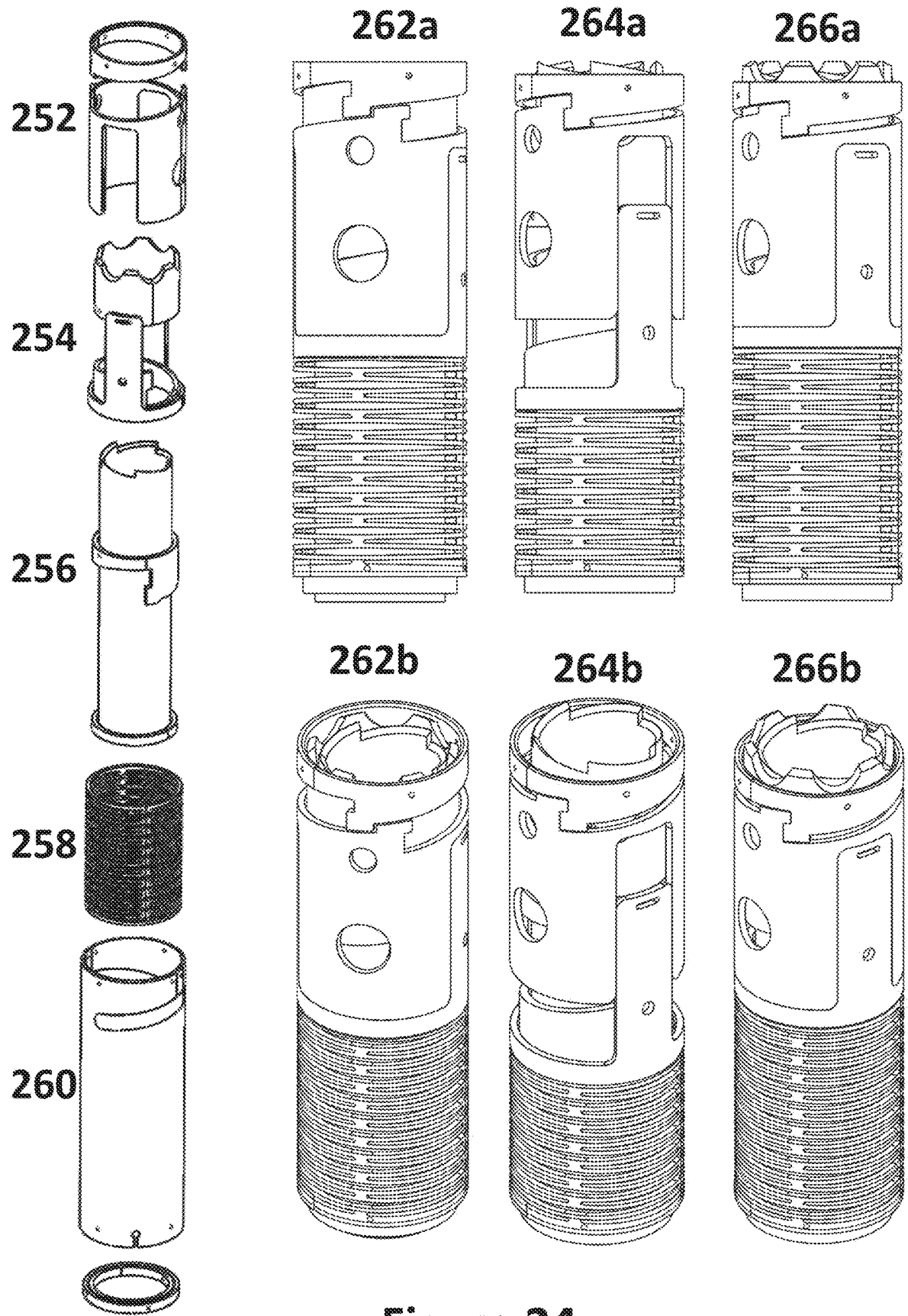
Figure 24H:
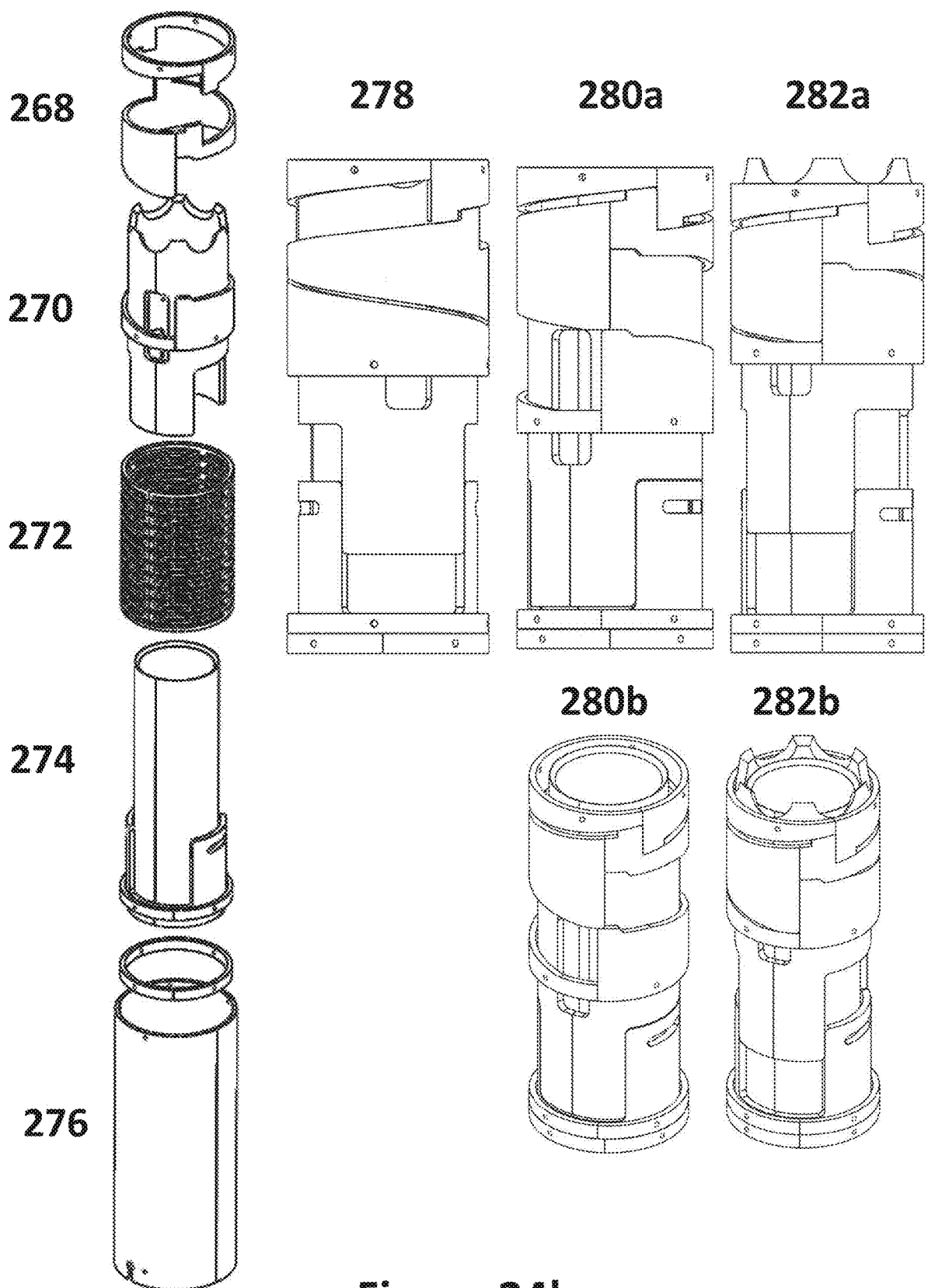
Figure 24I:
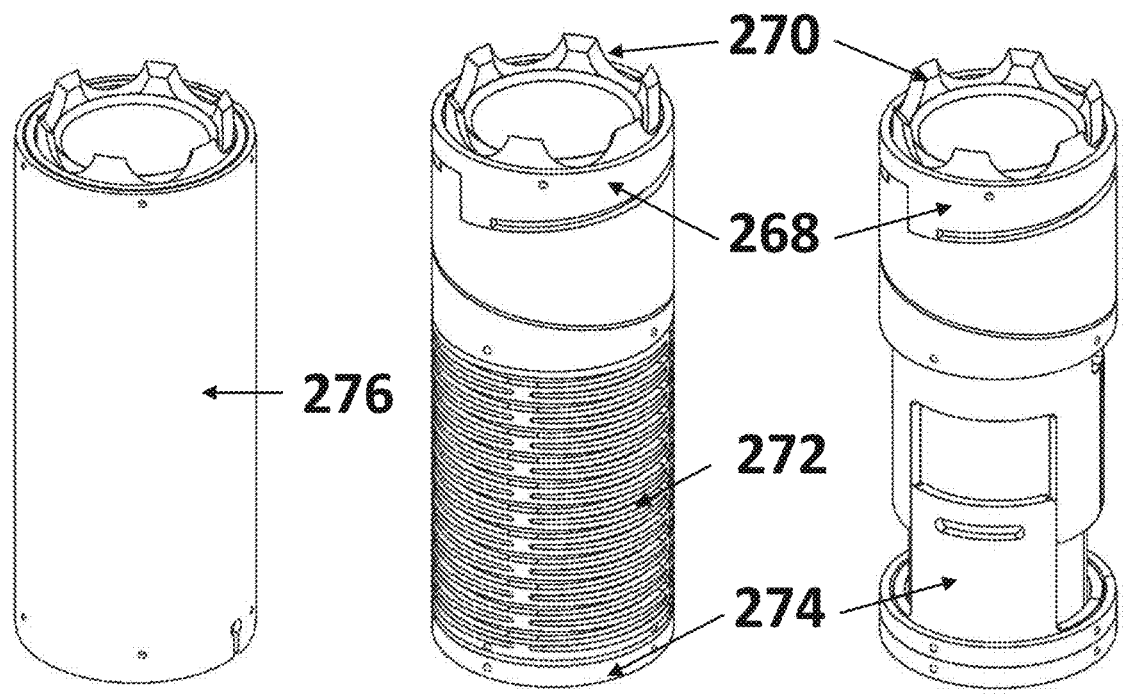
Figure 24J:
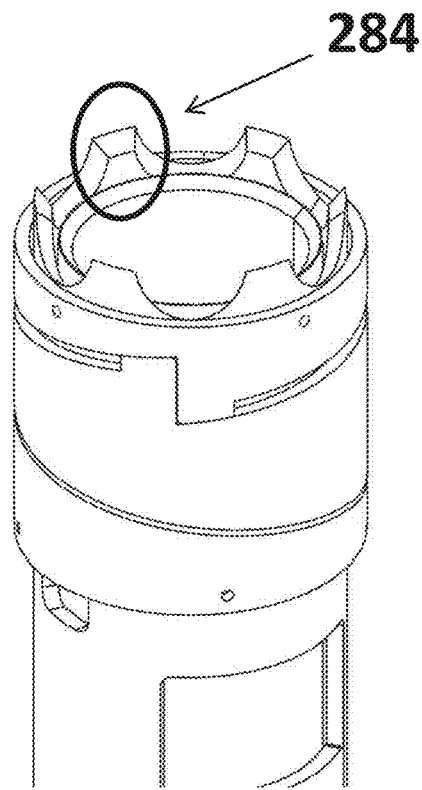
Figure 24K:
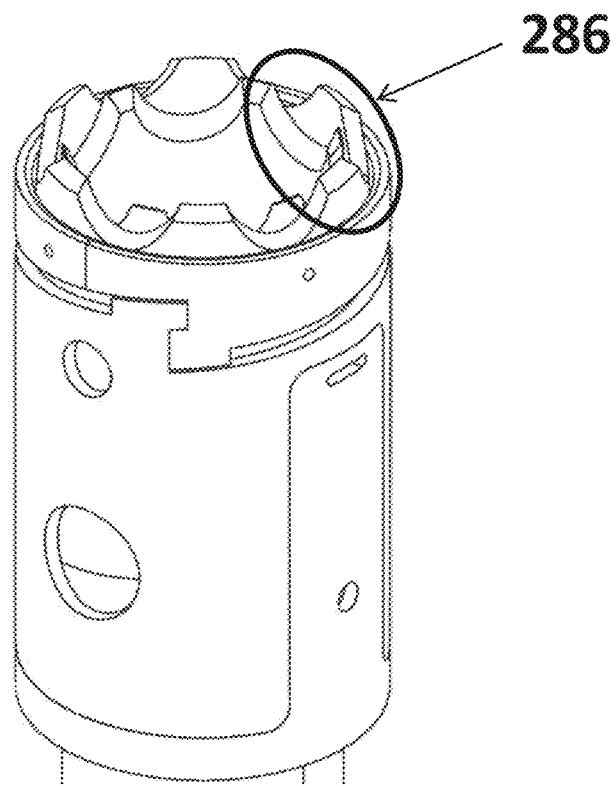
Figure 24L:
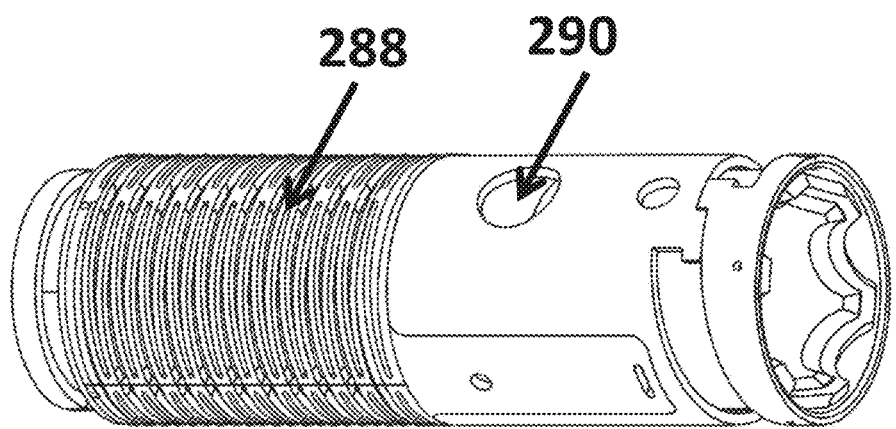
Figure 24M:
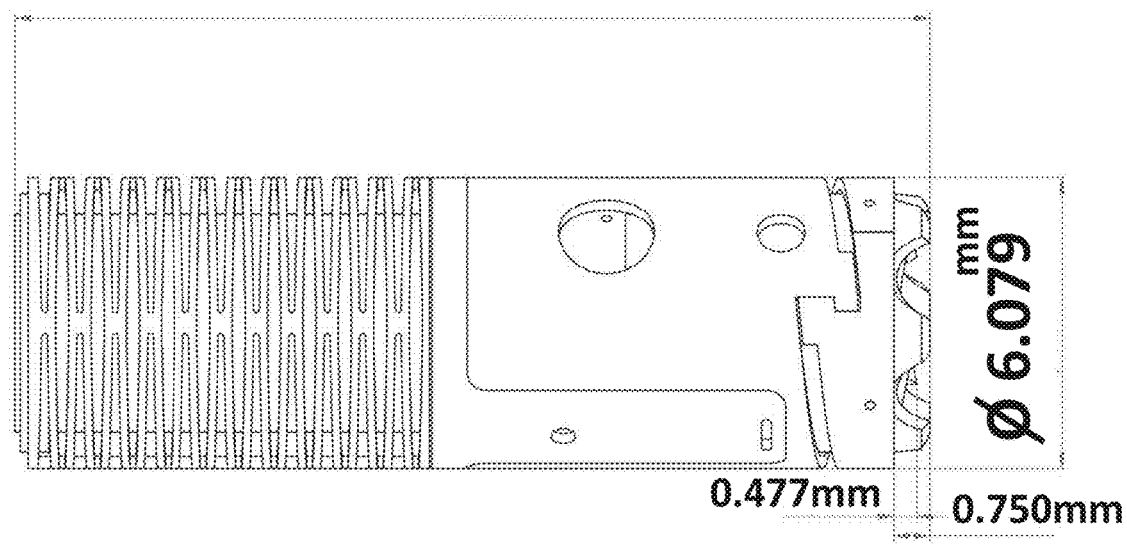
Figure 24N:
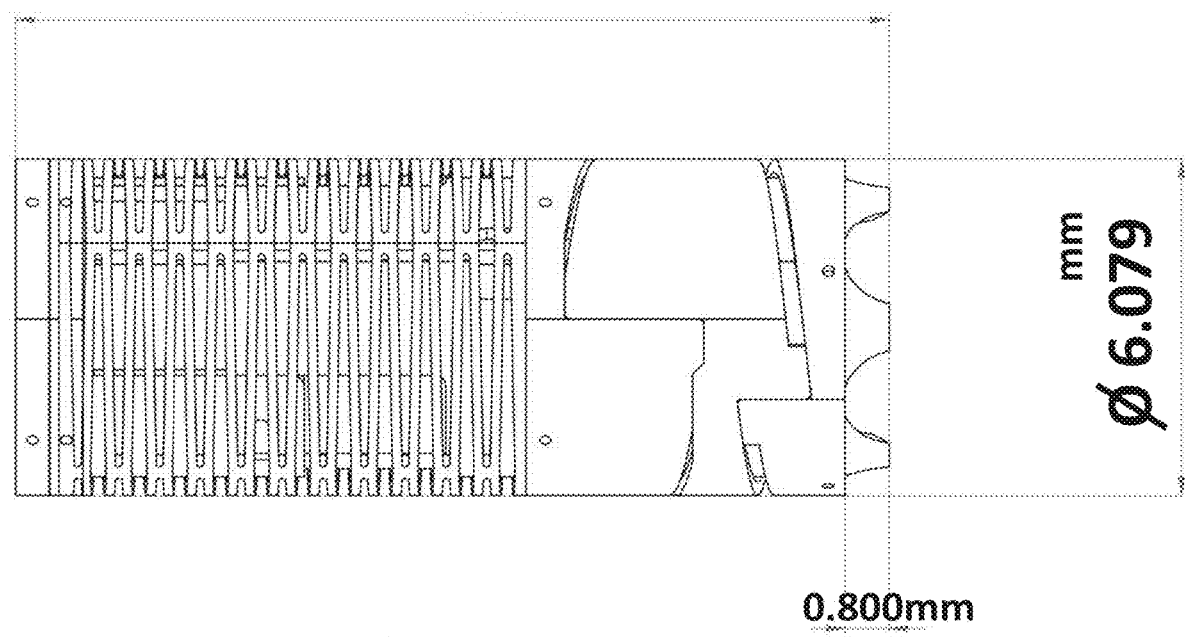
Figure 24O:
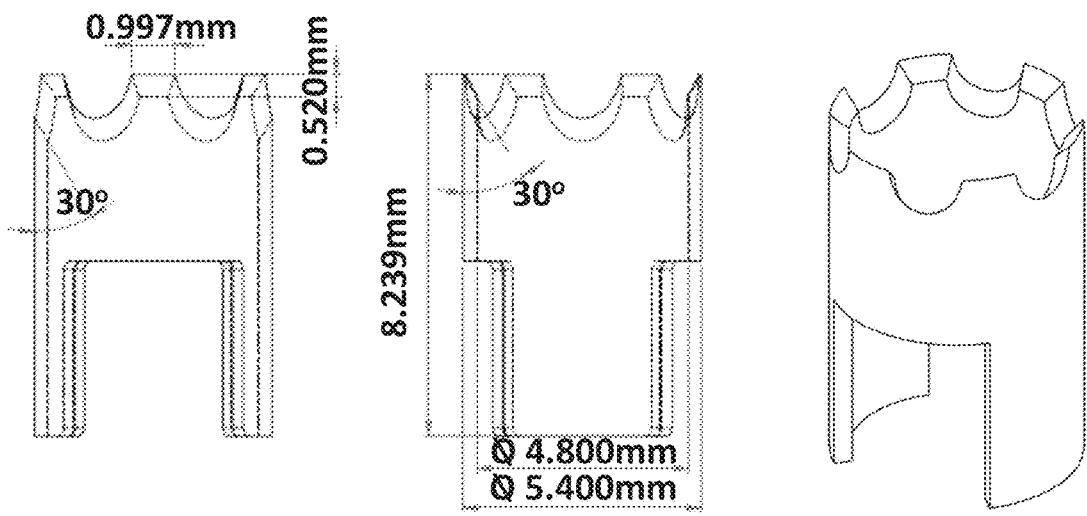
Figure 24P:
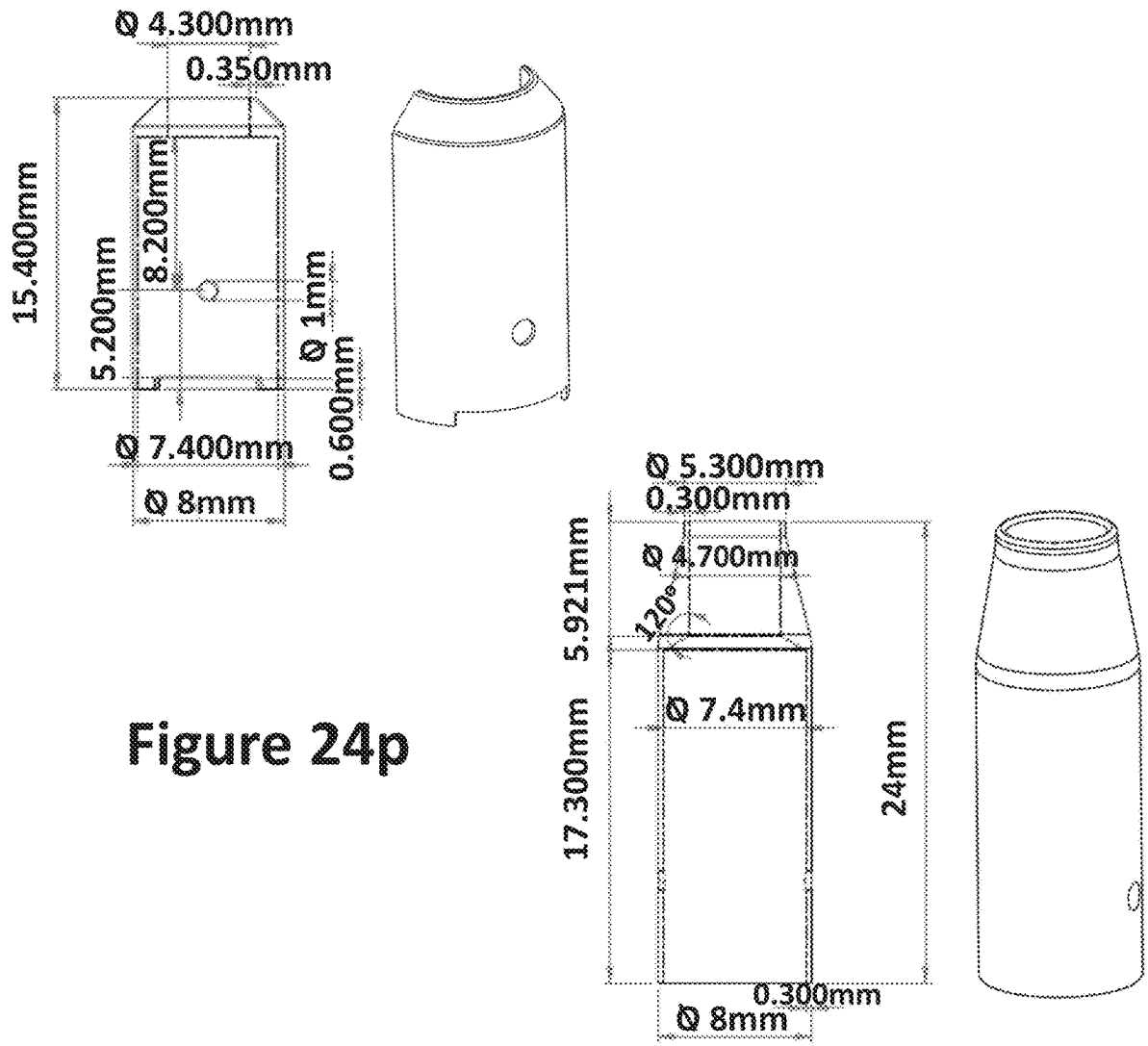
Figure 24Q:
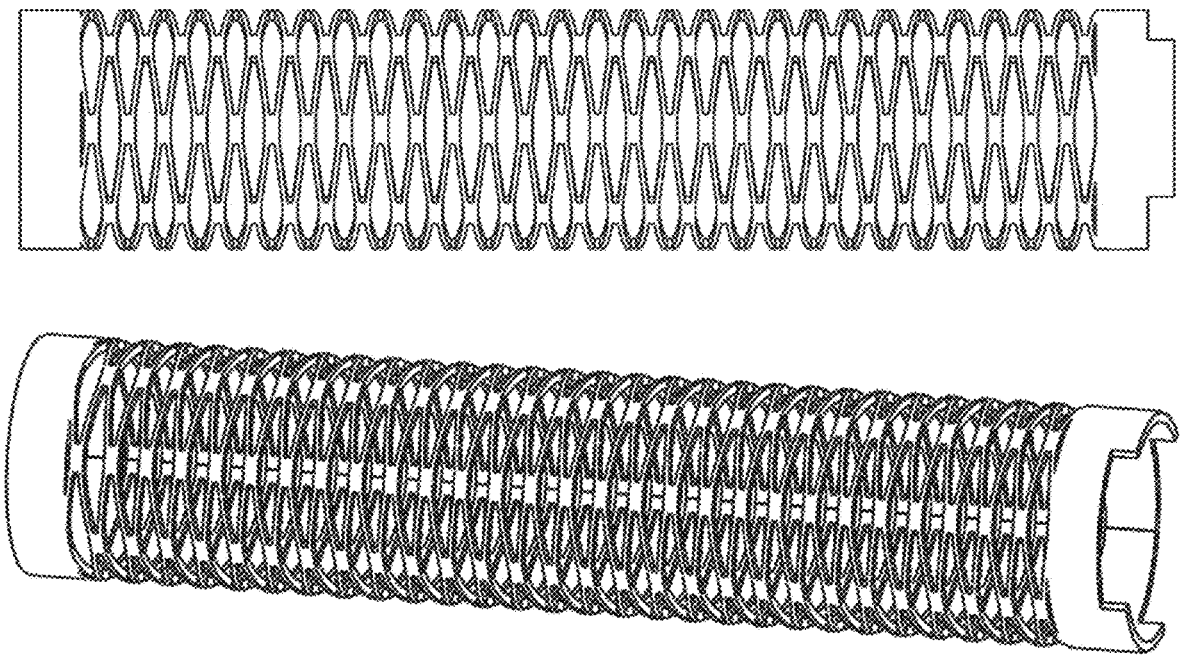
Figure 24R:
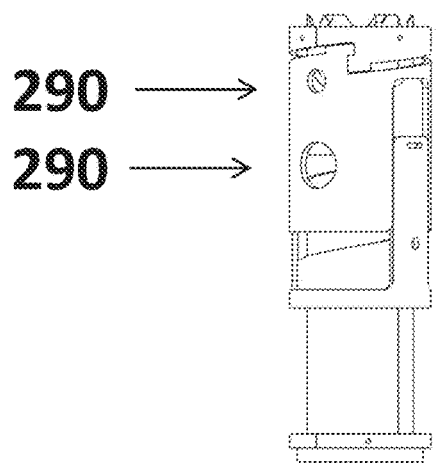

In some embodiments, a rotating motion mechanism is used in addition to the linear motion mechanism, as shown for example in FIGS. 24a-r. FIG. 24a shows a close-up of the handle 24 of the device and an example of a rotating motion mechanism 244 inside it. FIGS. 24b-d show perspective views of the example of the rotating motion mechanism showed in FIG. 24a. In some embodiments, the cutting of the tissue is performed by the linear movement of the first blades together with the rotating movement of the second blades, as will be further explained below. In some embodiments, the rotating mechanism rotates from right to left and/or from left to right. In some embodiments, blades located at the distal end of the device are used as cutting tool. In some embodiments, the cutting action is linear, which means cutting the tissue when moving blades back and forth (proximally and distally). In some embodiments, the cutting action is rotational, which means that the blades rotate CW and/or CCW with one set of blades or by rotating one set of blades against another to shear tissue between them (like scissors).

In some embodiments, the blades 246 are inserted or a cover 248 moves forward to protect from cutting the vein, as shown for example in FIG. 24e.

In some embodiments, the cutting or separating blades 250 are configured for example as shown in FIG. 24f, or other structure of blades or a combination thereof. In some embodiments, the rotating cutting mechanism and/or linear mechanism are as shown, for example in FIGS. 24g-h.

In some embodiments, the rotating cutting mechanism with the linear mechanism comprises, for example, the following parts: upper cradle and cradle 252 hammer, hammer bridge and CAM 254, rotating inner shaft and shaft cam 256, spring 258 and outer tube 260. In some embodiments, the CAM is the element that takes the hammer's blade into the free run area and the CAM is the part that will start the free run and stops the hit of the hammer according to the CAM structure. As can be seen ion FIG. 24g, 262a shows the configuration where the rotating blades and the hammer blade are inside, therefore inactive and guarded from cutting anything; 262b shows the same figure but in perspective—showing the blades inside. 264a shows the rotating blades outside while in action. The rotational action of the blades causes the CAM to move and to push backwards the hammer. It can be seen that the spring is being pulled backwards as well, therefore loading the hammer. 264b shows the same figure in perspective. 266a shows the hammer outside after it was fired and the rotating blades outside as well. 266b shows the same figure in perspective. The mechanism repeats itself with the rotation of the rotating blades. In some embodiments, the slope of the CAM might be linear, or quadratic or exponential to compensate for forces. In some embodiments, the slope translates directly to the force the shaft CAM applies on the CAM. In some embodiments, the more slope there is, there is less force but larger amplitude. In some embodiments, because it is driven by a spring, the force applied depends on the spring compression, and changes during the motion as the spring is released. In some embodiments, the compensation is performed by changing the angle of the slope, for example quadratically, to match the degree of release of the spring, to achieve constant force along the motion. In some embodiments, the CAM can be a structure of two slopes in order to have better aligned and centered linear movement of the hammer blade, when excoriating and moving forward to achieve the hit. In some embodiments, when the blade is rotating back, in case of retraction of the blades, the two cams rotate until they meet.

In some embodiments, the mechanism of friction at the lower cam, helps the device to move in correctly synced steps. In some embodiments, when the blades move forward to perform the hit, they first have to be exposed from the protective cover. In some embodiments, once the blades are exposed and have a clear path to the target, the CAM starts its rotation, loading the spring for the hit. In some embodiments, this order is ensured by the friction mechanism, which is a little 'step' in the two parts of the CAM right before the slope begins. In some embodiments, these matching steps make the two parts move together, pushing each other, until the blades are exposed. In some embodiments, only then they dislodge from one-another and start to slide, with the slope increasing the distance between them and loading the spring. This can be seen, for example, in FIGS. 24g and 24h.

In some embodiments, the cutting action is a combination of linear and rotational. In some embodiments, the linear mechanism and the rotating mechanism are synchronized. In some embodiments, the rotating motion mechanism further comprises a "hammer-drill like" mechanism. In some embodiments, the "hammer-drill like" mechanism enables to "hammer" (controlled strong forward strokes) while rotating the rotating blades. In some embodiments, the movement of the rotating blades together with the linear blades provides a scissor cutting effect. In some embodiments, both cutting mechanisms can be retracted inside the LE device/catheter. In some embodiments, the linear mechanism and the rotating mechanism are activated independently of each other.

In some embodiments, the device applies impact force to the target tissue. In some embodiments, the impact is generated by hitting the target. In some embodiments, in order to hit the target effectively the (one or more) hitting element (s) have a (relatively) "free run" path. In some embodiments, the path in which it accelerates comprises a region with friction, which is lower than the friction force and deceleration that is caused by the impact with the target tissue. An example of this can be seen, for example, in FIGS. 24h-i—showing the different layers of the mechanism: upper cradle and cradle 268, hammer, hammer bridge and CAM 270, spring 272, rotating inner shaft 274, and outer tube 276. In some embodiments, the CAM is the element that takes the hammer's blade into the free run area and the CAM is the part that will start the free run and stops the hit of the hammer according to the CAM structure. 278 shows the hammer mechanism in the inner safe position. 280a and 280b (perspective) show the hammer mechanism fully loaded. 282a and 282b (perspective) show the hammer mechanism after being activated. In some embodiments, the hitting element runs within the encapsulated range (the "free run"/acceleration path) a distance, for example, of 5 mm, 3 mm, 2.5 mm, 2 mm, 1.5 mm, 1.2 mm, 1 mm or 0.7 mm; optionally from about 0.2 mm to about 7 mm; optionally from about 0.7 mm to about 5 mm; optionally from about 1 mm to about 3 mm. In some embodiments, the distance outside of which the hitting element extends from the distal end of the catheter, as shown for example in FIG. 24j—284) is, for example, 0.3 mm, 0.5 mm, 0.8 mm, 1 mm or 1.3 mm; optionally from about 0.1 mm to about 3 mm; optionally from about 0.3 mm to about 2 mm; optionally from about 0.5 mm to about 2 mm. In some embodiments, the hitting element extends from the second blade that rotates, as shown for example in FIG. 24k—286, for example, 0.3 mm, 0.5 mm, 0.8 mm or 1 mm; optionally from about 0.1 mm to about 3 mm; optionally from about 0.3 mm to about 2 mm; optionally from about 0.5 mm to about 2 mm. In some embodiments, the hitting element is also rotating when returning into the "free run" area until it gets to the beginning of the acceleration path. Then, the hitting element, runs within the encapsulated range (the "free run"/acceleration path) a distance, for example, of 5 mm, 3 mm, 2.5 mm, 2 mm, 1.5 mm, 1 mm or 1.3 mm; optionally from about 0.1 mm to about 3 mm; optionally from about 0.3 mm to about 2 mm; optionally from about 0.5 mm to about 2 mm. In some embodiments, the structure of the hitting element is characterized by and internal diameter in range of the sheath. In some embodiments, the structure of the hitting element is characterized by an internal diameter from about 0.5 mm to about 7 mm; optionally from about 1 mm to about 5 mm; optionally from about 2 mm to about 4 mm, for example 1.5 mm, 2.5 mm, 3 mm, 3.5 mm, 4 mm, 4.4 mm, 5 mm, 6, or 7 mm. In some embodiments, the structure of the hitting element is characterized by a teeth number in the range of 0 to 8 units for example 0, 3, 6, 8. In some embodiments, the structure of the hitting element is characterized by a depth between teeth in the range from about 0 mm to about 3 mm; optionally from about 0.1 mm to about 2 mm; optionally from about 0.5 mm to about 1.5 mm, for example 0 mm, 0.5 mm, 1 mm. In some embodiments, the structure of the hitting element is characterized by a width of blade in the range of from about 0.1 mm to about 2 mm; optionally from about 0.2 mm to about 2 mm; optionally from about 0.5 mm to about 1 mm. In some embodiments, the structure of the rotating element is characterized by and internal diameter in range of the sheath. In some embodiments, the structure of rotating element is characterized by an internal diameter from about 0.5 mm to about 8 mm; optionally from about 1 mm to about 6 mm; optionally from about 1.5 mm to about 4 mm, for example 1.5 mm, 2.5 mm, 3 mm, 3.5 mm, 4 mm, 4.4 mm, 5 mm, 6 mm, or 7 mm. In some embodiments, the structure of the rotating element is characterized by a teeth number in the range of 0 to 8 units for example 0, 3, 6, 8. In some embodiments, the structure of rotating element is characterized by a depth between teeth in the range from about 0.1 mm to about 3 mm; optionally from about 0.3 mm to about 2 mm; optionally from about 0.5 mm to about 2 mm, for example 0 mm, 0.5 mm, 1 mm. In some embodiments, the structure of the rotating element is characterized by a width of blade in the range of from about 0.1 mm to about 2 mm; optionally from about 0.2 mm to about 2 mm; optionally from about 0.5 mm to about 1 mm.

In some embodiments, the source for generating the hitting is, for example, as follows:

The linear motion approach: the force is generated at the handle: wherein the generation of the impact motion is at the handle side and is transmitted forward by a coupling item along the catheter, such as a compression coil, or push-able stiff wires (e.g. made of Stainless Steel or NiTi). In some embodiments, the motion is contained within the inner shaft and affecting mostly the inner parts, and not the whole device. This may be advantageous because impact motions will not cause the whole device to move while inside the patient.

The "rotational cam with a spring at the tip" approach:
a. In some embodiments, the force is generated by a rotational sheath (e.g. HSS) that surrounds the lead;
b. In some embodiments, the force is generated by a side wire/cable/NiTi structure, HSS, which does not surround the lead, and rotates and transfers the momentum to the tip;
c. In some embodiments, the force is generated by a combination in which part of the path comprises a rotational sheath (e.g. HSS) that surrounds the lead and part of the path comprises a side wire/cable/NiTi structure, also HSS, that does not surround the lead.

The "linear charging spring at the tip" approach: wherein the spring is at the tip and the tip is being pulled/compressed to "charge" the spring (either compress it or stretch it relative to its rest condition). The tip is then abruptly released. The loading of the spring can be performed by pulling or pushing a side wire/cable/NiTi structure, HSS, that transfers the pulling or pushing force to the tip.

In some embodiments, the impact is characterized by the characteristics, for example, of a spring. In some embodiments, the hammer spring when pressed from starting length of about 8 mm to about 5.5 mm it will give a force from about 150 gf to about 3000 gf; optionally from about 300 gf to about 2000 gf; optionally from about 500 gf to about 1000 gf. For example, it can be 250 gf, 350 gf, 5000 gf, 650 gf, 850 gf, 1000 gf, 1,500 gf, 2000 gf, 2,500 gf or 3000 gf when the spring is pressed by the cam in the head, as shown for example in FIG. 24g—252a-b. In some embodiments, when pushing the blades into a surface, neither the hammer nor the rotating blade retracts due to counter forces. In some embodiments, the system withholds forces up to 250 gf, 350 gf, 5000 gf, 650 gf, 850 gf, 1000 gf, 1,500 gf, 2000 gf, 2,500 g or 3000 gf. In some embodiments, even if the user is pushing the handle, the system will not move since it comprises a "stopper" at the distal head. In some embodiments, the spring comprises a length of from about 2 mm to about 12 mm; optionally from about 4 mm to about 10 mm; optionally from about 6 mm to about 8 mm. In some embodiments, the spiral spring comprises wire diameter in the range from about 0.1 mm to about 5 mm; optionally from about 0.5 mm to about 3 mm; optionally from about 1 mm to about 2 mm. In some embodiments, the complex spring structure comprises struts of from about 0.05 mm to about 0.45 mm; optionally form about 0.08 mm to about 0.40 mm; optionally from about 0.1 mm to about 0.2 mm; for example 0.1 mm, 0.15 mm, 0.21 mm, 0.25 mm. In some embodiments, a complex spring structure is manufactured by cutting a stainless-steel tube or Niti, as shown for example in FIG. 24*l* (288). In some embodiments, the length of the non-engaged spring will be from about 5 mm to about 10 mm; optionally from about 6 mm to about 9 mm; optionally from about 7 mm to about 8 mm; for example: 6 mm, 7 mm, 7.5 mm, 8 mm. In cases where a preload effect is desired, the non-engaged spring will from about 8 mm to about 20 mm; optionally from about 10 mm to about 18 mm; optionally from about 12 mm to about 16 mm; for example: 9 mm 10 mm 13 mm or 14 mm. In some embodiments, the length of the engaged spring will be from about 2 mm to about 10 mm; optionally from about 3 mm to about 8 mm; optionally from about 4 mm to about 7 mm; for example: 3.5 mm, 4 mm, 5 mm, 5.5 mm or 6 mm.

In some embodiments, as examples, the head of the device comprises the following dimensions as disclosed in FIGS. 24*m-n*. FIG. 24*m* shows a distal head with two blades—one rotating and one hammer. FIG. 24*n* shows a distal head with rotating and hammer in the same blade.

In some embodiments, the rotating blade (the lower diameter blade) has a phase of 30 degrees facing to the inner diameter. In some embodiments, the rotating blade comprises a phase of from about 20 degrees to about 90 degrees; optionally from about 30 degrees to about 80 degrees; optionally from about 40 degrees to about 70 degrees; for example 60 degrees, 50 degrees, 30 degrees. In some embodiments, the dimensions of the rotating blade are as shown, for example, in FIG. 24*o*.

In some embodiments, the hammer blade (the higher diameter blade) has a phase of 50 degrees facing to the outer diameter of the tube. In some embodiments, the hammer blade comprises a phase of from about 20 degrees to about 90 degrees; optionally from about 30 degrees to about 80 degrees; optionally from about 40 degrees to about 70 degrees; for example 60 degrees, 50 degrees, 30 degrees.

In some embodiments, the dimensions of the head comprises an arrow-like shape, as disclosed, for example in FIG. 24*p*, arrowhead (right lower corner) compared to non-arrow head (middle).

In some embodiments, the cutting element is characterized by a combination of a rotational set of teeth, so to generate a cutting effect of a dual tooth-saw (as opposed to stretching or single tooth saw approach). In some embodiments, the combination includes one set moving predominantly longitudinally while the other predominantly rotates (which acts like a wiper that removes blocked tissue and avoids congestion, often called "snow plowing effect").

In some embodiments, the device is characterized by a combination of a steering of the head, with a metal-based (articulated) bending structure (i.e. inner bending shaft), so that forces of XYZ or moments of ZYX are transferred to the tip without causing unwanted movements of the bending structure and without blocking of the rotational component or linearly moving components. In some embodiments, the bending component is made of a spring, or a cut tube or an articulated structure as shown for example in FIG. 24*q* (inner bending shaft—showed in two different perspectives). In some embodiments, the inner component (sheath/HSS) that rotates or moves linearly is made of a spring. In some embodiments, the springs can be an extension coil for example OD 5.5 mm WT 0.5 mm-1 mm pitch 0.5 mm-1 mm length can be as the sheath, made of metal like stainless steel (example: manufacture "febrotec" part number 0T49060, 0T49030) In some embodiments, the spring is designed to transfer the motion in/out or rotation, but not to stretch, e.g. by bonding along its inner radius in case of linear motion.

7.3 Exemplary Fluid Dynamics and Forces

Movements of parts often behave differently in an air-based environment and in a liquid-based environment. While parts move freely in an air-based environment, due to lack of resistance, in a liquid-based environment they do not. This can disturb the correct function of parts of the LE device.

In some embodiments, the LE device is characterized by having dedicated holes on parts of the device configured to allow movement/displacement of liquids during activation of moving parts of the device, thereby reducing the resistance of the liquid on the moving parts. Exemplary holes are shown, for example, in FIG. 24*l* (290), and FIG. 24*r* (290). In some embodiments, the holes provide access from the outside of the device to the inside of the device, and vice versa, allowing the flow of liquids to and from the two zones.

8. Exemplary Balloon Embodiment

In some embodiments, the LE device comprises an inflatable system (balloon) adapted to be inflated and deflated by the user. In some embodiments, the inflatable balloon is applied in a variety of uses. In some embodiments, the inflatable balloon is used as a tissue separator. In some embodiments, the inflatable balloon is used for isolating specific zones from the blood flow (see below). In some embodiments, the inflatable balloon is used as anchorage for the LE device. In some embodiments, the inflatable balloon comprises built-in canals, which allow blood flow to run in them.

Figure 25A:
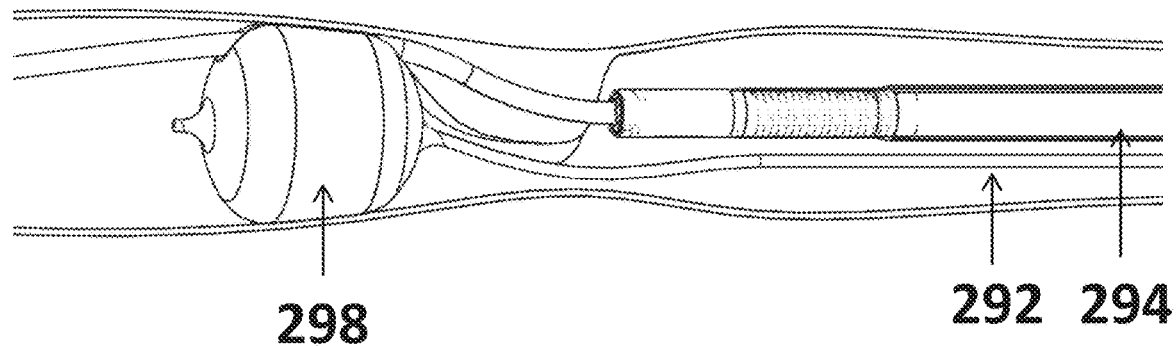
FIGS. 25a-e are schematic views of exemplary balloon embodiment, according to some embodiments of the present invention.

In some embodiments, the inflatable system runs inside the LE device, alongside the lead. In some embodiments, the inflatable system 292 runs outside the LE device 294, as shown for example in FIGS. 25*a-b*. In some embodiments, the inflatable system 292 runs outside the LE device, inside a dedicated elongated canal 296 attached to the LE device 294, as shown for example in FIG. 25*c*. In some embodiments, the balloon 298 of the inflatable system 292 is deployed distally ahead of the LE device when the user encounters a place where the lead has been encapsulated by fibrous tissue, as shown for example in FIGS. 25*a-c*. In some embodiments, the inflatable system 292 can be deployed circumventing the fibrous tissue, as shown for example in FIG. 25*c*. In some embodiments, the inflatable system 292 can be deployed traversing through the fibrous tissue.

In some embodiments, the deployment of the balloon distally of the fibrous tissue, and inflating the balloon 298 as to put the fibrous tissue between the inflated balloon 298 and the LE device 294 is used as a method for providing further support to the LE device. In some embodiments, once the balloon 298 is inflated, the user pulls proximally the inflation system 292 cord thereby providing a stable counter support for the LE device 294, which needs to move forward in a distal direction.

Figure 25B:
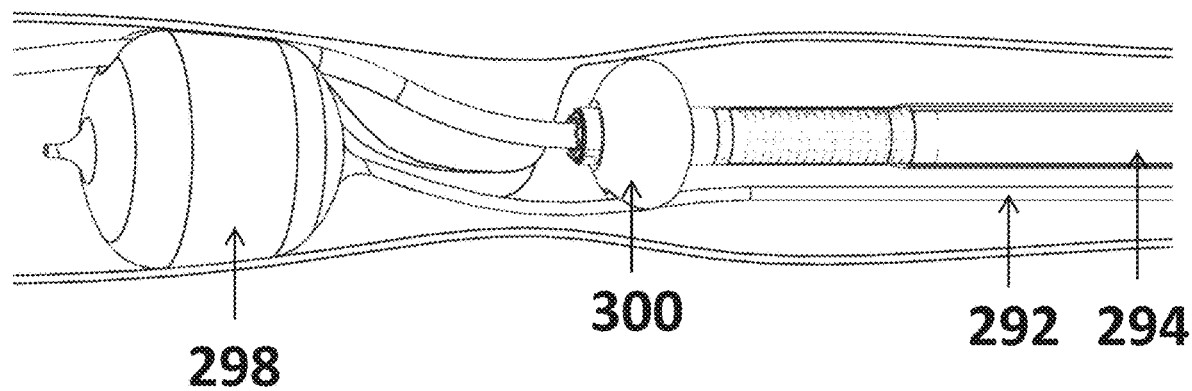
Figure 25C:
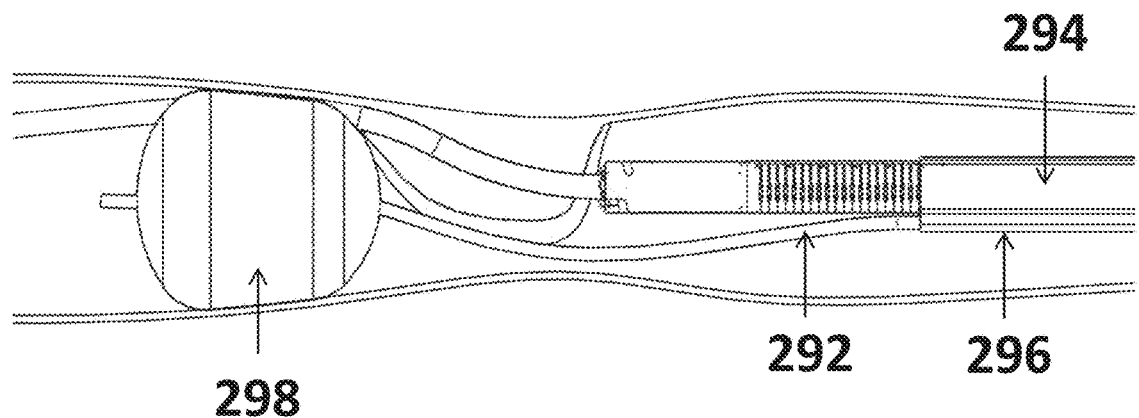

In some embodiments, the inflation system 292 comprises a built-in inflatable ring-like balloon 300 around the head in the distal end of the LE device 294, as shown in FIG. 25*b*. In some embodiments, the ring-like balloon 300 is compartmentalized and each compartment is inflated independently. In some embodiments, the inflated ring-like balloon 300 is used an anchorage to the LE device by pressing the vein walls.

In some embodiments, the ring-like balloon 300 is inflated and also a forward distally balloon 302 is inflated distally of the fibrous tissue. The two inflated balloons (300, 302) create a closed space, which, in some embodiments, can be filled with saline (or other transparent liquid) and enable visibility for microcameras located at the distal end of the LE device 294, for example. This is shown, for example in FIG. 25*b*.

Figure 25D:
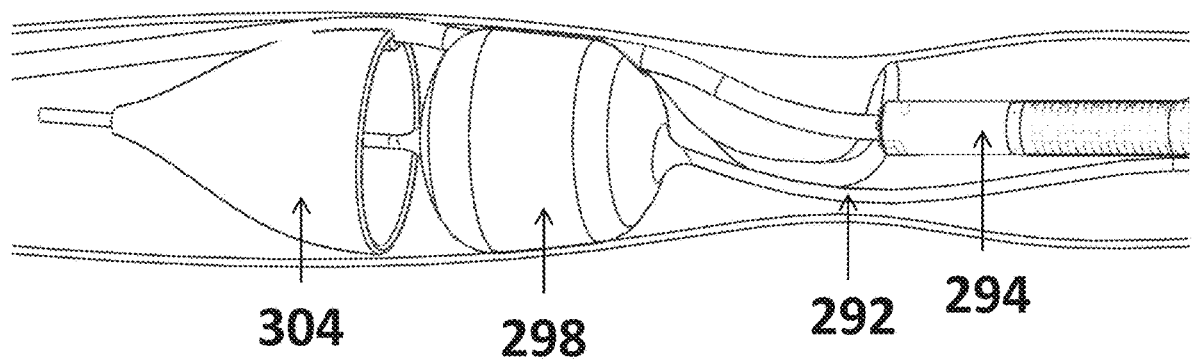

In some embodiments, the inflation system 292 further comprises a deployable net 304, as shown for example in FIG. 25*d*. In some embodiments, the deployable net 304 is configured to allow the passage of blood and to block the passage of debris caused by the elimination of fibrous tissue around the lead during the activation of the LE device. In some embodiments, the deployable net 304 is deployed by itself, regardless of the inflation system 292.

Figure 25E:
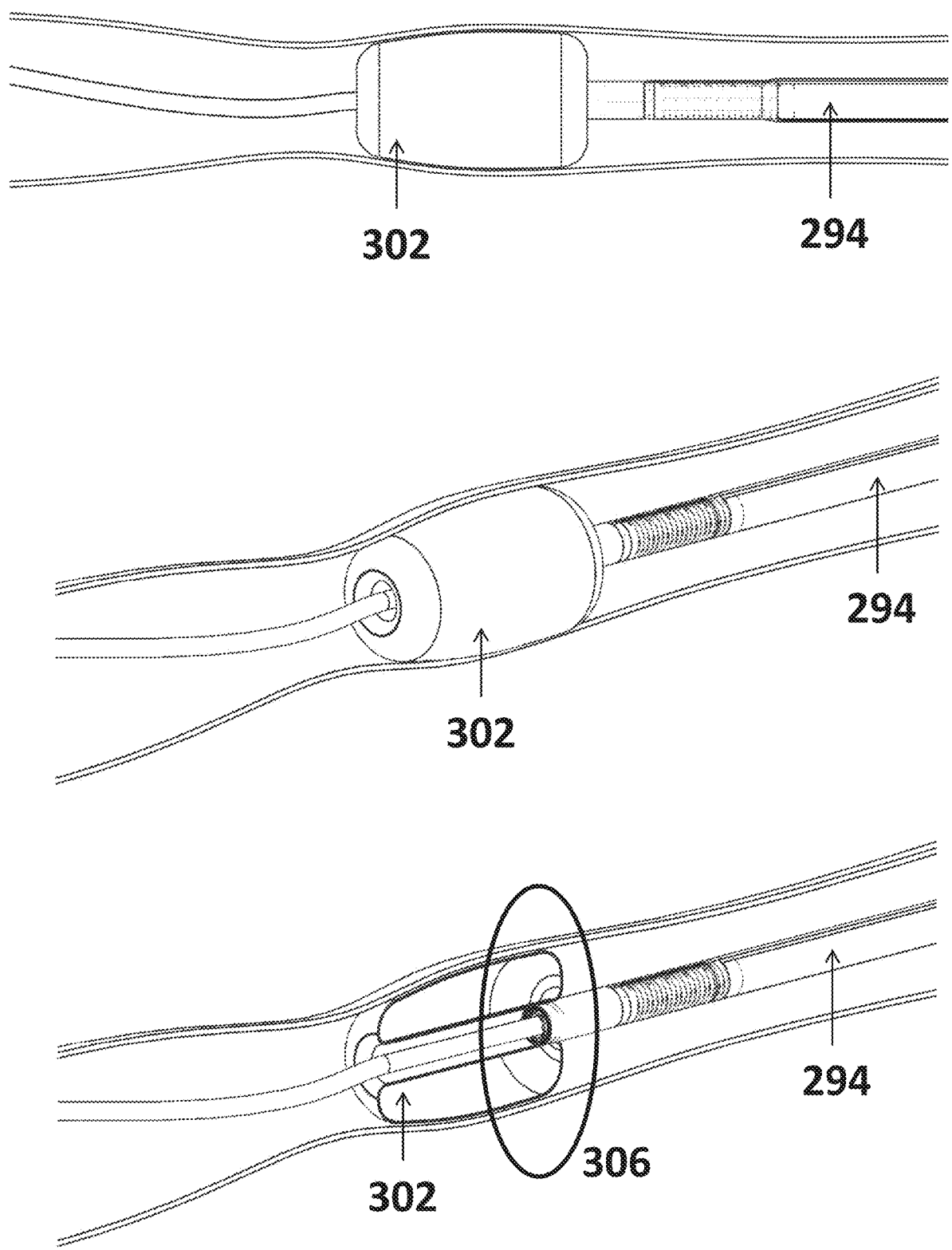

In some embodiments, the inflation system 292 is built-in 306 (circle) in the outside of the head of the LE device 294, as shown in FIG. 25*e*. In some embodiments, the built-in inflation system extends partially along the circumference of the head of the LE device. In some embodiments, the head of the LE device comprises more than one built-in inflation system along its circumference. In some embodiments, the deployed inflated balloon works as a tissue separator. In some embodiments, the deployed inflated balloon surrounds the lead, providing space for the lead to move, while gently pushing the vein walls, as shown for example in FIG. 25*e*. In some embodiments, this method is complementary to the cutting method of the LE device. In some embodiments, this method is substitute to the cutting method of the LE device.

In some embodiments, the balloon, when inflated, can support a force of 1 Newton, or 10 Newton, up to 50 Newton without collapsing or undergoing deformation. In some embodiments, the balloon has a defined form when inflated, and does not stretch and increase in volume under inflation pressure of 2 atmospheres or less. In some embodiments, the balloon can withstand contact with the blades located in the distal end of the device.

9. Additional Information

In some embodiments, the device is used as a lead extraction (LE) device, as an atherectomy device, as an object extraction device, and/or as any device for extracting an object from one or more veins and/or a heart chamber and/or the cardiovascular system and/or any tubular structure/lumen in the body (including GI tract). In some embodiments, the device is used for separating an object and/or tissue from surrounding vascular/lumen tissue and/or to separate and/or dissect fibrous/calcified tissue/plaque. In some embodiments, the object is an implantable pacing or a defibrillation lead. In some embodiments, the lumen is a cardiovascular lumen inside the body. In some embodiments, the lumen is a vein inside the body. In some embodiments, the lumen is a heart chamber inside the body.

In some embodiments, the steering is controlled by: 2 pulling wires and/or one or more pulling wires with one or more springs to straighten the catheter and/or one or more springs to keep the wire tight. In some embodiments, the device includes an extension coil to maintain length while the catheter is flexible along its path. In some embodiments, the steering tool comprises modes: free—to maintain flexibility of the catheter and allow it to freely respond to path curvatures and/or to counter force applied by the tissue or leads; or sets a certain force/pressure/moment but responds (bends/stretches) to changes in the curvature of the path/catheters and/or responds the counter force applied by the tissue of by the leads; or sets fixed elongation/stretch/bending at the tip. In some embodiments, the modes can be changed manually, for example, by engaging the pulling wires and holding them firmly to set a fixed bending, or letting them loose to have the bending angle free to be changed by the path it is in.

In some embodiments, the device provides controlled steering of the tip to control the orientation of the force or applied energy to the desired target tissue and reduce the likelihood of applying the energy to the vein wall.

In some embodiments, the controlled steering mechanism is integrated with extraction tool and forms a single device with steering of its head, which applies cutting, sawing, and/or impact forces to the tissue by its tip. The steering provides control of the orientation of the forces.

In some embodiments, the device is an outer sheath with steerable bending capabilities that provides control over an extraction tool (whether mechanical or laser or thermal or ultrasound, or balloon based, or others) that passes through (internally) the steerable outer sheath device. In some embodiments, the steerable outer sheath is made of stainless steel or plastic. In some embodiments, the steerable outer sheath bends up to 90 degrees or less over a radius of up to 20 mm or larger and length of 100 mm up to 1400 mm; for example 30 mm, 48 mm, 90-1200 mm. In some embodiments, the steering device slides over the extraction tool and can control the location of the bending along the path of the extraction tool.

In some embodiments, the steerable sheath has a circular lumen with a length of at least 5 cm (or up to 10 cm, or up to 20 cm, or at least 20 cm, or 20-30 cm, or 25 to 55 cm or 90-140 cm) through which the extraction tool is passed. In some embodiments, the steerable sheath has a side opening, such that it can be attached to or fitted over an extraction tool from the side of the extraction tool without having to pass the tip of the extraction tool through the steerable sheath. In some embodiments, the steerable sheath has a separator component that opens the side opening to enable passage of the extraction tool through its side into the steerable sheath, and enable closure (whether full or partial) of the steerable sheath over the extraction tool.

10. Exemplary Pulling/Grapping Device 6

Figure 26A:
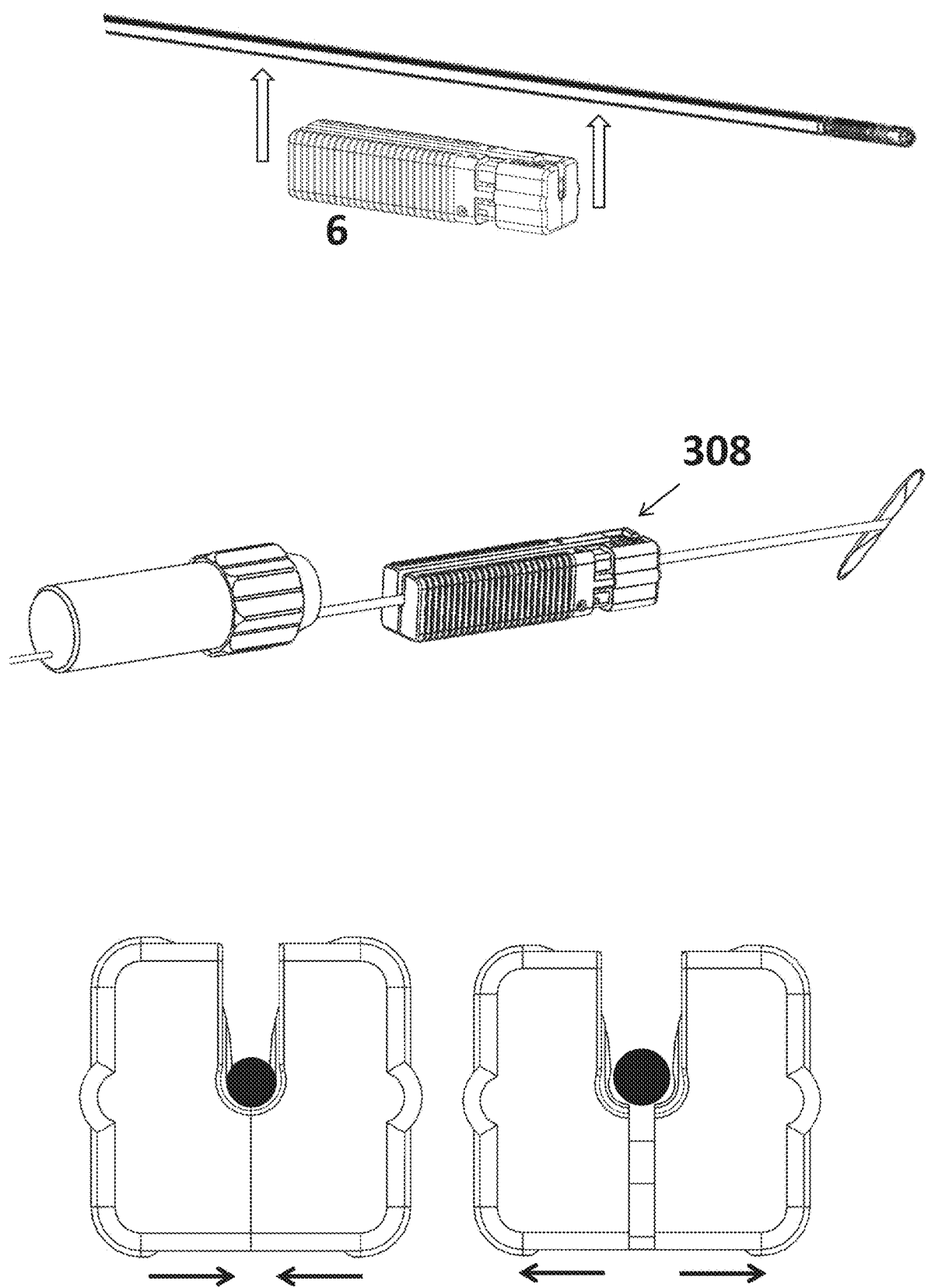
FIGS. 26a-e are schematic views of exemplary pulling/grapping device, according to some embodiments of the present invention.
Figure 26B:
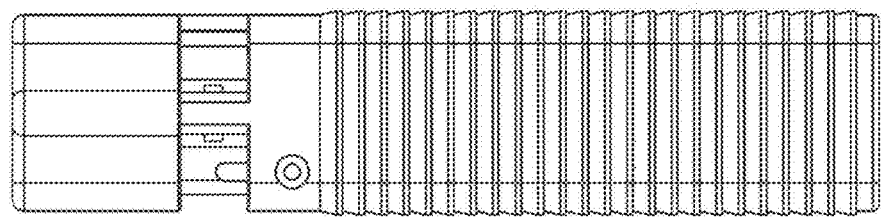
Figure 26C:
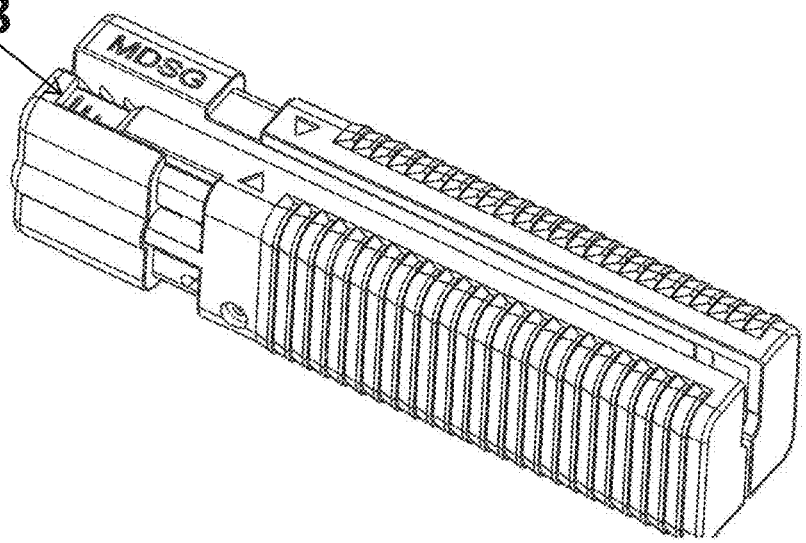
Figure 26D:
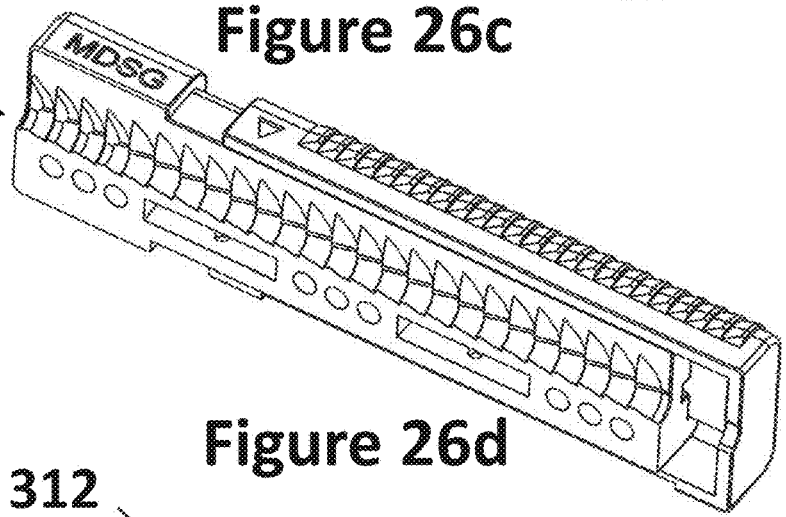
Figure 26E:
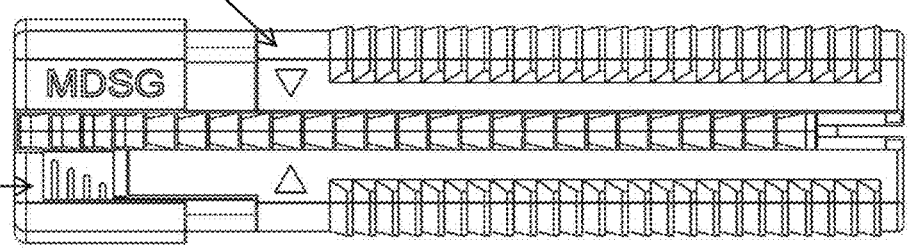

In some embodiments, a dedicated handle 6 is attached to a LE device which provides an ergonomical grapping of the sheath, said dedicated handle is held by the free hand of the user for wrapping, catching and pulling the sheath. In some embodiments, the handle is reversibly attached to the LE device at a location of choice of the user, as shown for example in FIG. 26*a*. In some embodiments, the handle comprises a longitudinal aperture which allows the mounting and dismounting of the handle from the LE device during the procedure performed by the user. In some embodiments, the dedicated handle is adjustable to grab the sheath or be loose to slide on the sheath according to the pressure that the user applies. In some embodiments, the handle comprises a force indicator 308, which enables the user to be aware of the force applied when pushing/pulling, as shown for example in FIG. 26*a*. In some embodiments, the indicator is a meter, a screen showing colors, a sound, or any other suitable system (e.g. to be shown on displays, on fluro, etc.). Some examples of architecture of the handle can be seen, for example in FIGS. 26*b-e*. In some embodiments, the handle is configured to be attached to a variety of sizes and lengths of LE devices/catheters.

In some embodiments, a dedicated handle will have additional lock (not shown) to prevent from unwanted dismounting.

In some embodiments, the inner side of the handle is designed to fit the sheath of the LE device, and in some embodiments, it includes a rubber or radial shaped configuration 310 or other to increase the friction between the handle and the sheath and to reduce damage to the sheath.

In some embodiments, the handle comprises a manual stepper 312 of pulling, so the user does not apply force by hand, but rather determines either the force or the distance of progress relative to the handle, as shown for example in FIGS. 26*a-e*. In some embodiments, the handle comprises a force/distance/velocity limiter, so no pulling becomes too abrupt (when an obstacle is gone, the force of pushing and pulling makes the catheter run with less control that might impact the vein).

In some embodiments, the handle includes an option to stay locked on the sheath, so the user can push\pull the handle without having any concern of maintaining the grab on the handle but just for pushing or pulling in along the sheath.

11. Exemplary Pulling Device 4

The extraction of the lead from the patient is typically performed by pulling the lead from the patient. During the extraction, the user usually coils the pulled lead on his own hand in order to continue pulling the lead. The coiled lead hurts the user had.

Figure 27:
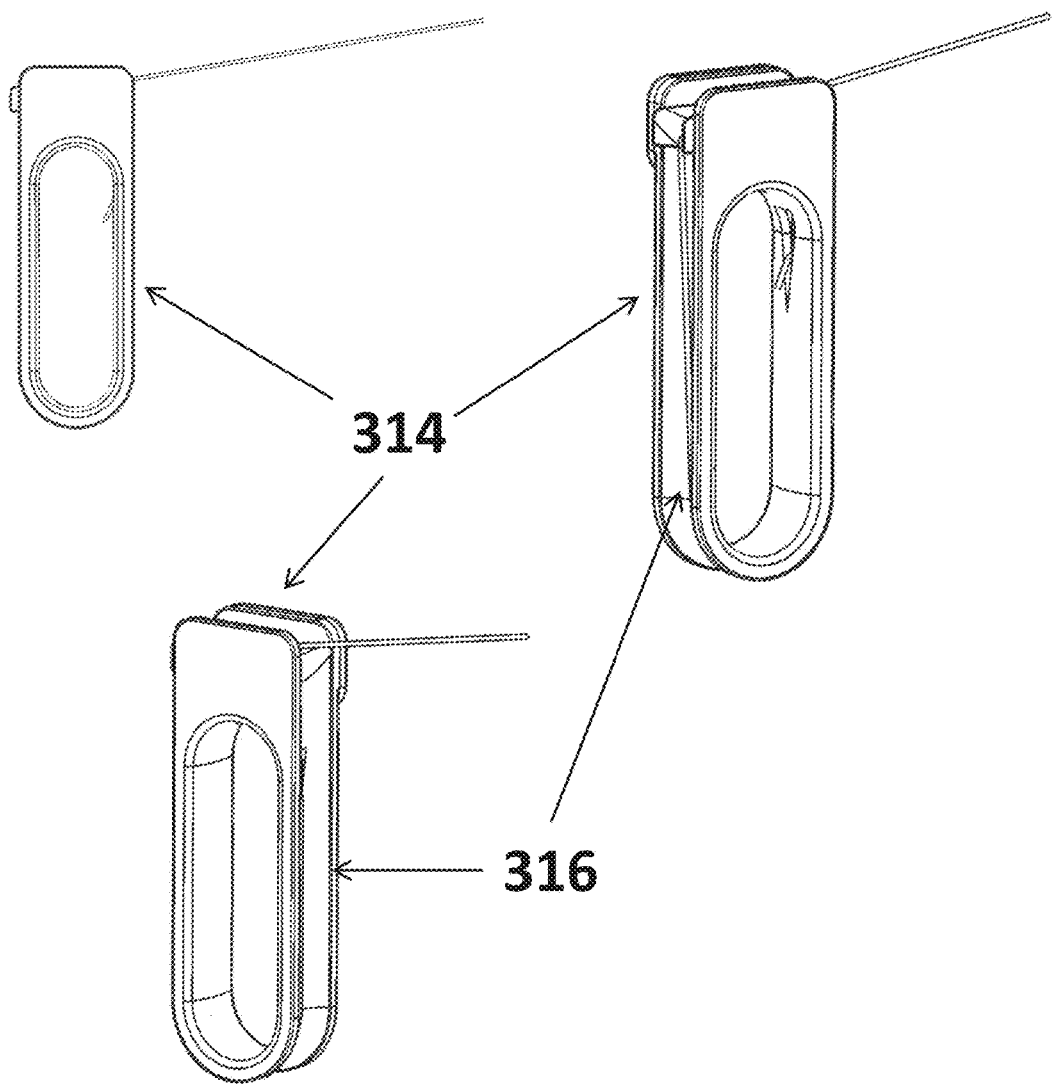
FIG. 27 are schematic views of exemplary pulling device, according to some embodiments of the present invention.

In some embodiments, a pulling accessory device is used. In some embodiments, the pulling accessory comprises a body 314, adapted to be held by the user and surrounds the hand of the user. In some embodiments, the pulling accessory comprises a canal or groove 316 on its external periphery where the extracted lead is collected. In some embodiments, the lead is firmly attached to the pulling accessory device. In some embodiment, the user coils the styletes/wires/lead around the pulling accessory device therefore not damaging the user's hand. In some embodiments, the pulling accessory device comprises a force indicator. In some embodiments, the pulling accessory device is as shown, for example, in FIG. 27.

12. Exemplary Accessories

In some embodiments, add-on's and/or accessories, for example, lead cutter, sensors, steering, force measure, etc., are adapted to be either an integral part of the lead extraction device or an add-on as separate tools or combined add-on's. In some embodiments, accessories are used without requiring taking the extractor out from the patient. For example, wires or other cutting tools can be mounted externally to the existing extraction tool and pushed in the body along the said device till reaching the distal end and preform the cutting action.

12.1 Steerable Sheath (for LE Device)

In some embodiments, when the user already has an LE device without steerable capabilities, it would be an improvement to enable said LE device with steerable capabilities. In some embodiments, a steerable sheath is used to provide LE devices with steerable capabilities. In some embodiments, the steerable sheath 318 is reversibly attachable to the LE device, as shown for example in FIG. 28. In some embodiments, the distal part of the sheath 318*a* is the steerable part. In some embodiments, the steerable part can be made in different dimensions and different materials from the sheath, like plastic or metal or other material according to the existing LE device.

Figure 29:
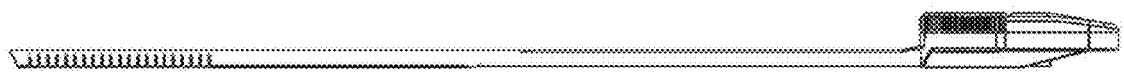
FIG. 29 is a schematic view of exemplary steerable sheath embodiment, according to some embodiments of the present invention.

In some embodiments, the hinge (part of the steering mechanism), the sheath and the active parts which maintain the needed pushing and pulling forces, are all part of an unified device, as shown for example in FIG. 29. In some embodiments, the user pulls and pushes as needed in the procedure but the shape of the hinge stays fixed as the user tuned, due to the internal mechanisms inside the hinge and the extractor, which ensure the stability of the steered end albeit the forces. In some embodiments, the device and the extruder are adapted to sustain the strong forces due to the materials chosen and the design which enable them to hold the torque and pulling and pushing forces.

Figure 28:
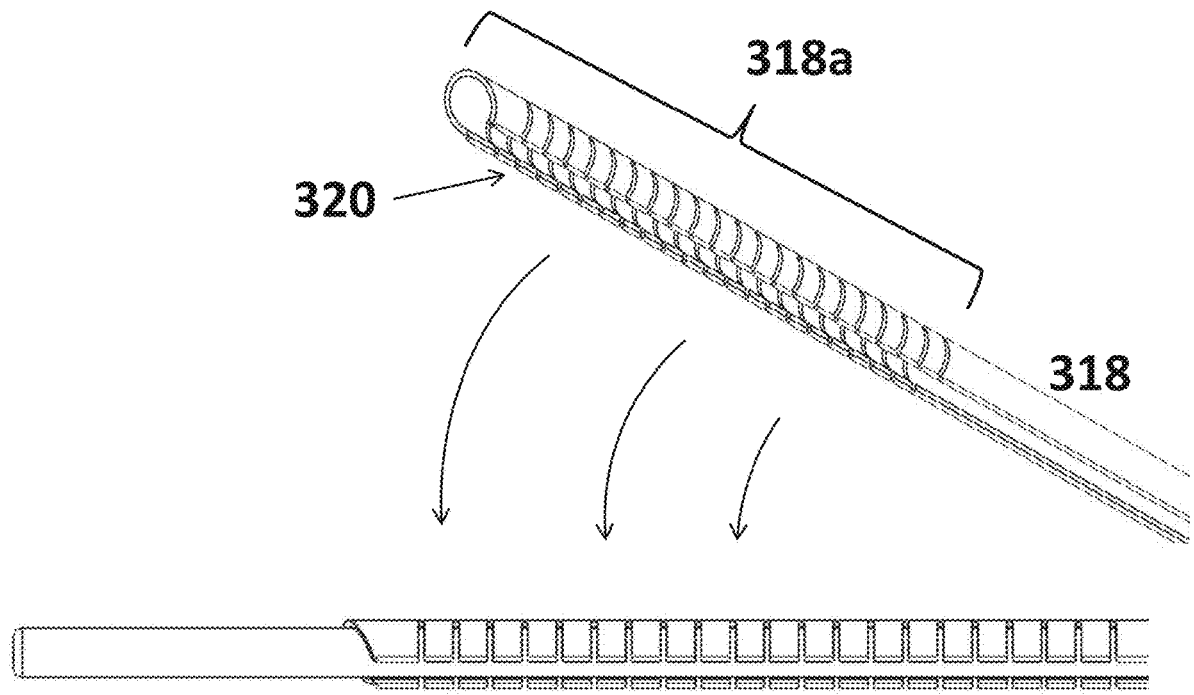
FIG. 28 is a schematic view of exemplary steerable sheath embodiment, according to some embodiments of the present invention.

In some embodiments, the sheath comprises a longitudinal aperture or sideway insertion with hooks 320, as shown for example in FIG. 28, which enables the attachment and removal of the steering sheath from the LE device during the physician regular procedure.

Figure 30A:
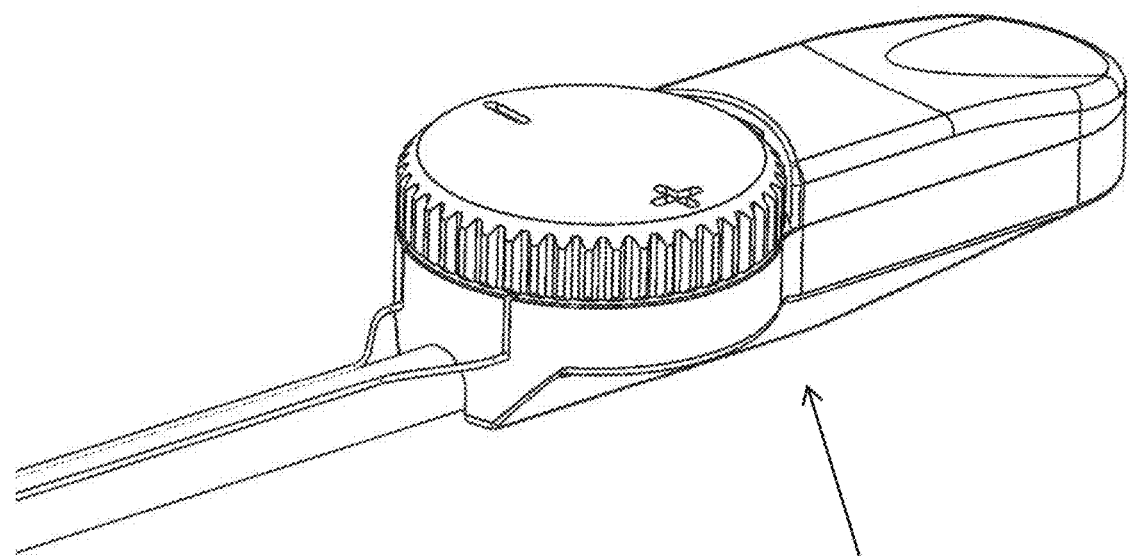
FIGS. 30a-b are schematic views of exemplary steerable sheath embodiment, according to some embodiments of the present invention.
Figure 30B:
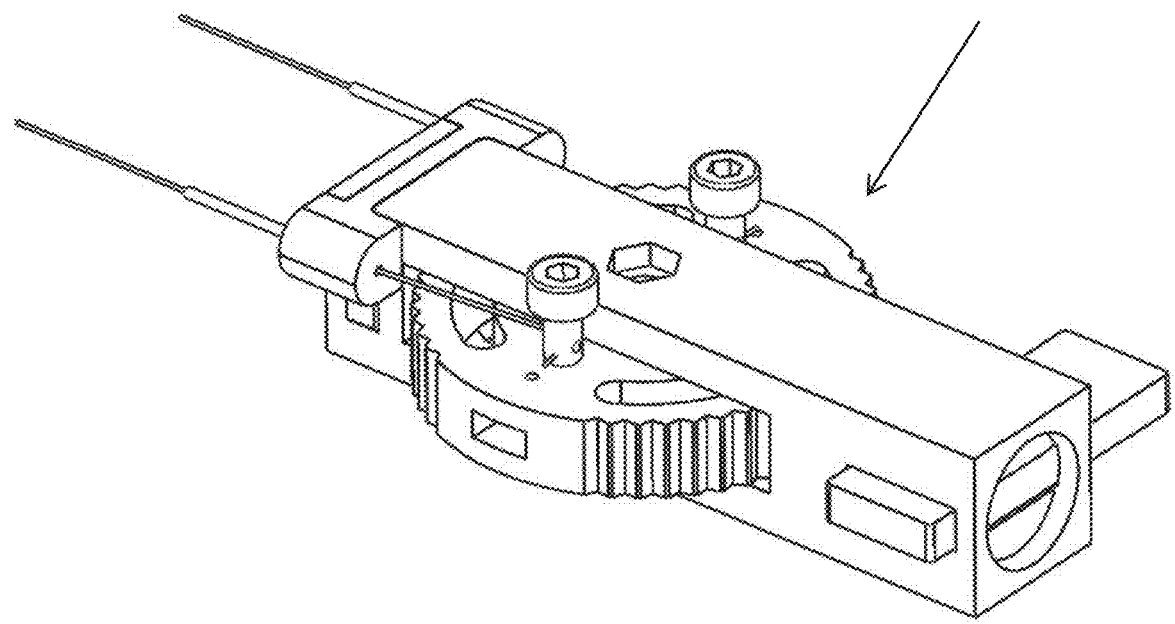

In some embodiments, a manual controller of the steering movement 322 is located on the proximal end of the steerable sheath, close to the user, as shown for example in FIGS. 30*a-b*. FIG. 30*b* showing the internal mechanism of the manual controller shown in FIG. 30*a*. In some embodiments it can be relocated during procedure.

In some embodiments, the length of the sheath can be from 10 cm to 1.4 meter.

Figure 31:
FIG. 31 is a schematic view of exemplary steerable sheath embodiment, according to some embodiments of the present invention.
Figure 32:
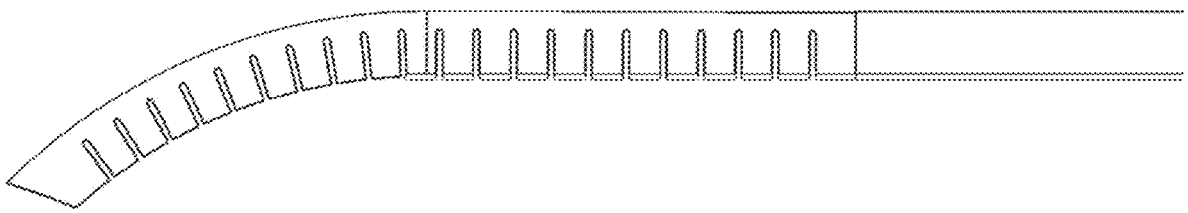
FIG. 32 is a schematic view of exemplary steerable sheath embodiment, according to some embodiments of the present invention.

In some embodiments, once the steerable sheath is mounted on the LE device (as shown in FIG. 31), the user actuates the controller which steers the distal end of the LE device, as shown for example in FIG. 32. In some embodiments, the steering is performed from left to right and/or to right to left and\or axial rotating on the sheath or handle.

In some embodiments, the steering movement is adapted to be loose. In some embodiments, the steering movement is adapted to be stiff. In some embodiments, the steering movement is adapted to be manipulated according to the physician request.

In some embodiments, the handle of the steerable device is ergonomically designed longitudinally to the LE device, as shown for example in FIG. 30*a*. This feature enables the user to control the steering of the LE device while holding the proximal end of the LE device, potentially leaving the second hand of the user free for other roles during the procedure.

In some embodiments, the proximal end of the steerable sheath is configured to be firmly attached to the LE device, permitting the user to use it for pulling and/or pushing actions. In some embodiments, the proximal end of the steerable sheath is configured to be attached to a variety of sizes of LE devices/catheters.

In some embodiments, the handle of the steerable sheath comprises a force indicator, which enables the user to be aware of the force applied when pushing/pulling. In some embodiments, the indicator is a meter, a screen showing colors, a sound, or any other suitable system (e.g. to be shown on displays, etc.).

In some embodiments, the handle of the steerable sheath comprises an indicator showing how much the distal head of the LE device is bent by the vein, and how much resistance the bending head has when trying to bend. In some embodiments, these indicators are used as indicators of obstacles.

12.2 Exemplary Attachment Ring for LE Device

Figure 33A:
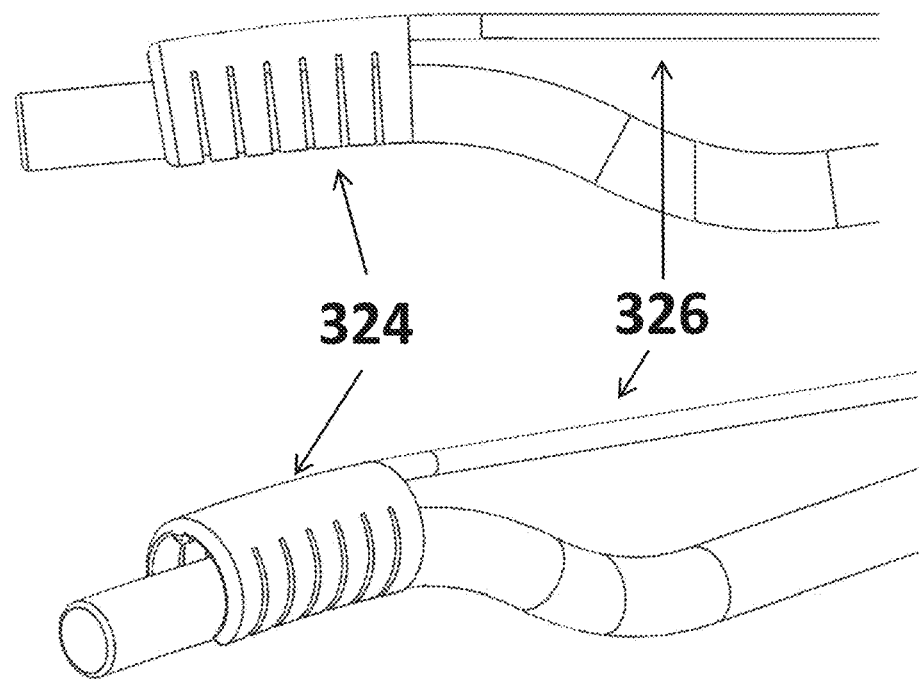
FIGS. 33a-c are schematic views of exemplary attachment ring for LE device embodiment, according to some embodiments of the present invention.
Figure 33B:
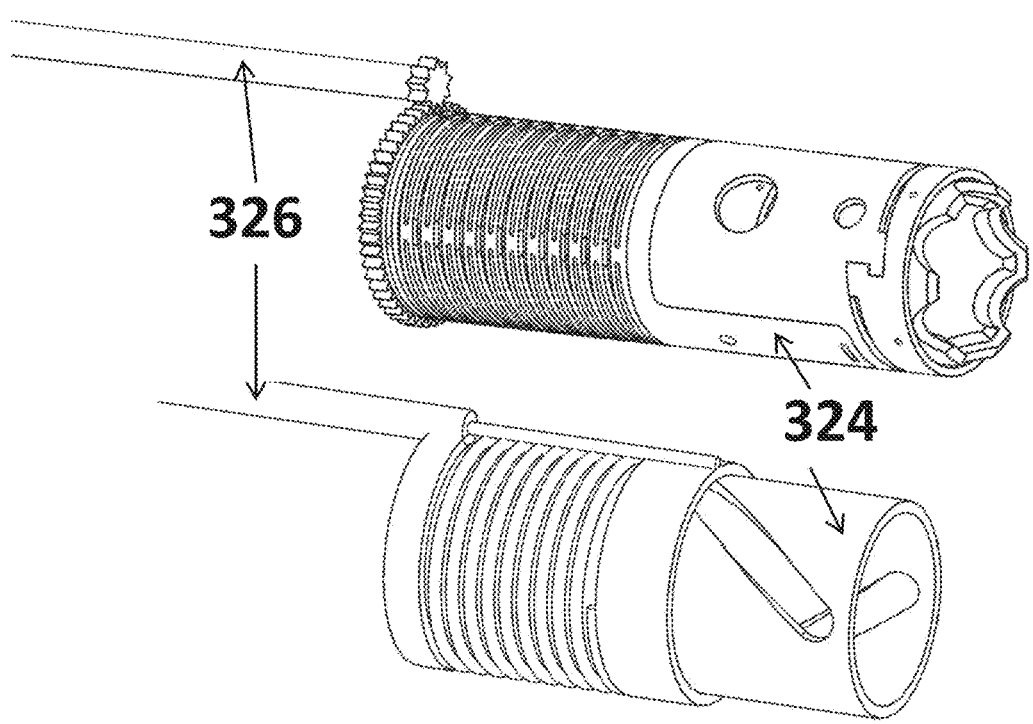
Figure 33C:
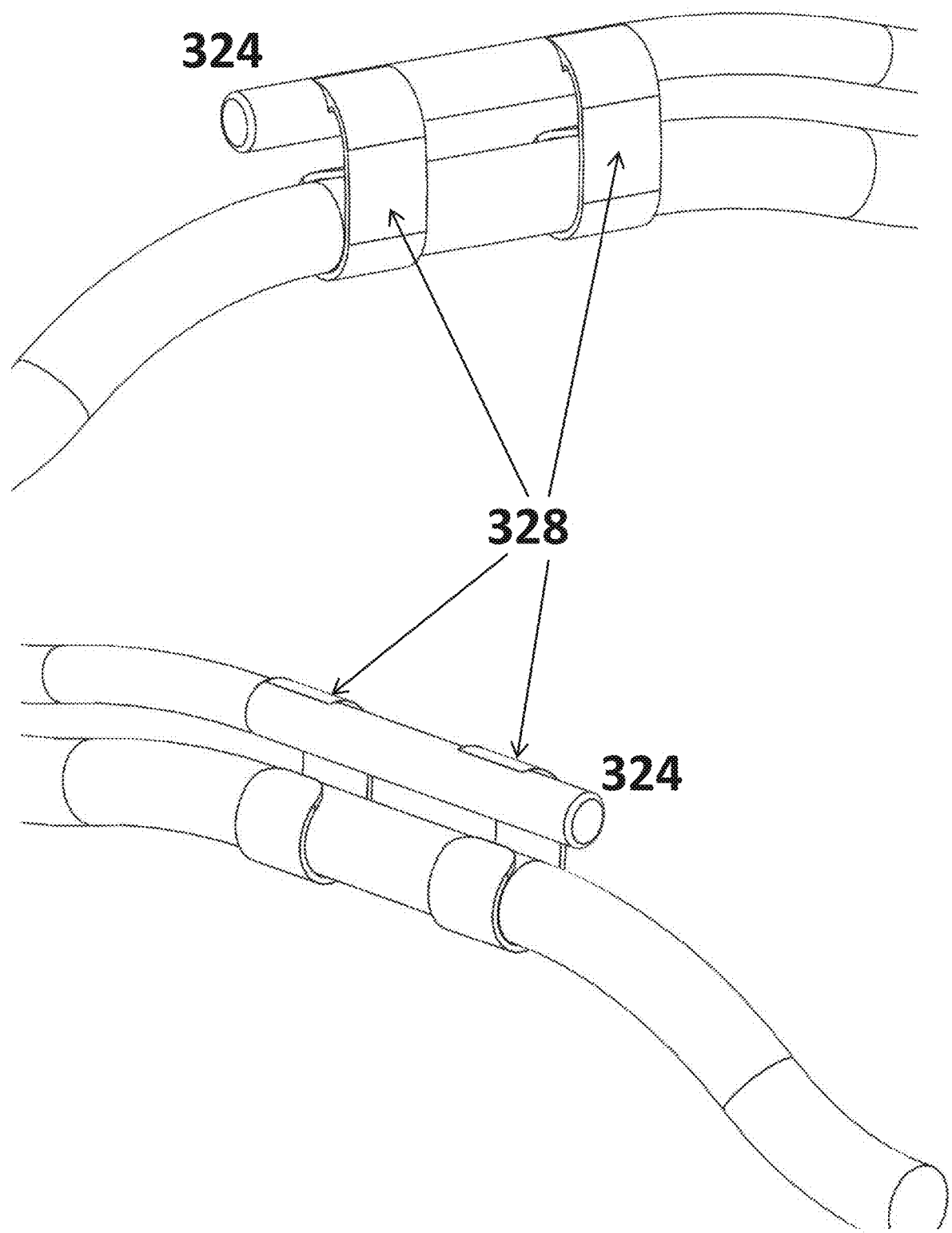

In some embodiments, the mechanisms disclosed (e.g.: steering mechanism, cutting mechanism, etc.) are configured in a single "head unit" which is attachable to an existing LE device deprived of said mechanisms or to the lead itself, as shown for example in FIGS. 33*a-b*. In some embodiments, the head unit 324 is connected to an elongated body 326 which comprises on its proximal end the hand controller of the mechanisms (not shown). In some embodiments, the elongated body 326 comprises inside all the required machinery for activating the mechanisms in the head unit. In some embodiments, the head unit is reversible attachable to an existing LE device or the lead itself, as shown for example in FIG. 33*a*. In some embodiments, the head unit is not directly attached to a LE device or the lead, rather it utilizes a ring-like attachment 328, as shown for example in FIG. 33*c*. In some embodiments, the ring-like attachment "hugs" the LE device or the lead, and this attachment is used for guiding and following the head unit to the path of the lead. In some embodiments, the total diameter of the LE device and the head unit connected to the elongated body are from about 5 mm to about 8 mm.

12.3 Exemplary Pulling/Grapping Accessory Device

Figure 34:
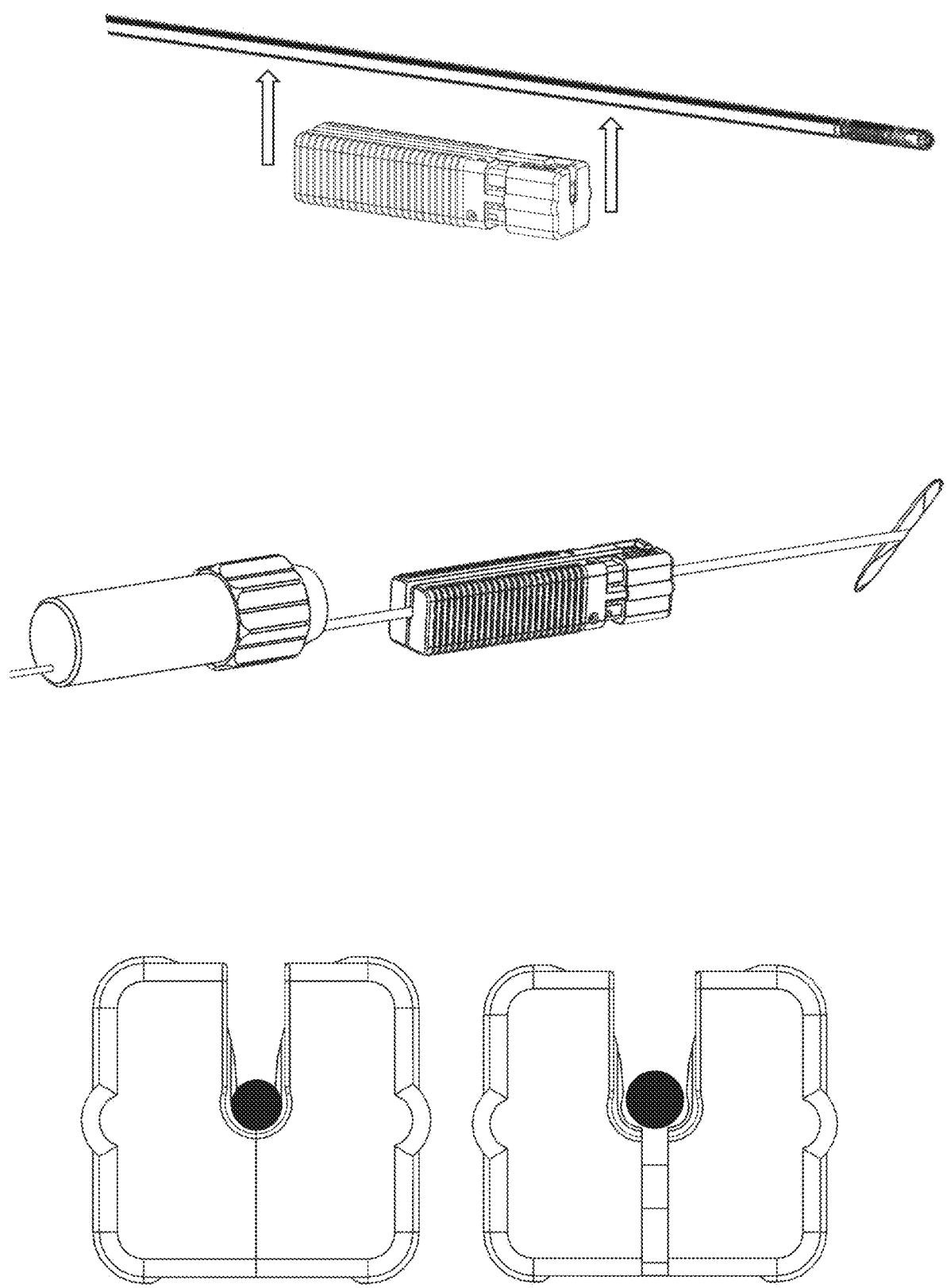
FIG. 34 are schematic views of exemplary pulling/grapping accessory device, according to some embodiments of the present invention.

In some embodiments, a dedicated accessory handle is attached to a LE device, which provides an ergonomical grapping of the sheath, said dedicated handle is held by the free hand of the user for wrapping, catching and pulling the sheath. In some embodiments, the handle is reversibly attached to the LE device at a location of choice of the user, as shown for example in FIG. 34. Exemplary characteristics related to the handle accessory are disclosed above in section 10.

12.4 Exemplary Pulling Device Accessory

The extraction of the lead from the patient is usually performed by pulling the lead from the patient. During the extraction, the user usually coils the pulled lead on his own hand in order to continue pulling the lead. The coiled lead hurts the user had.

Figure 35:
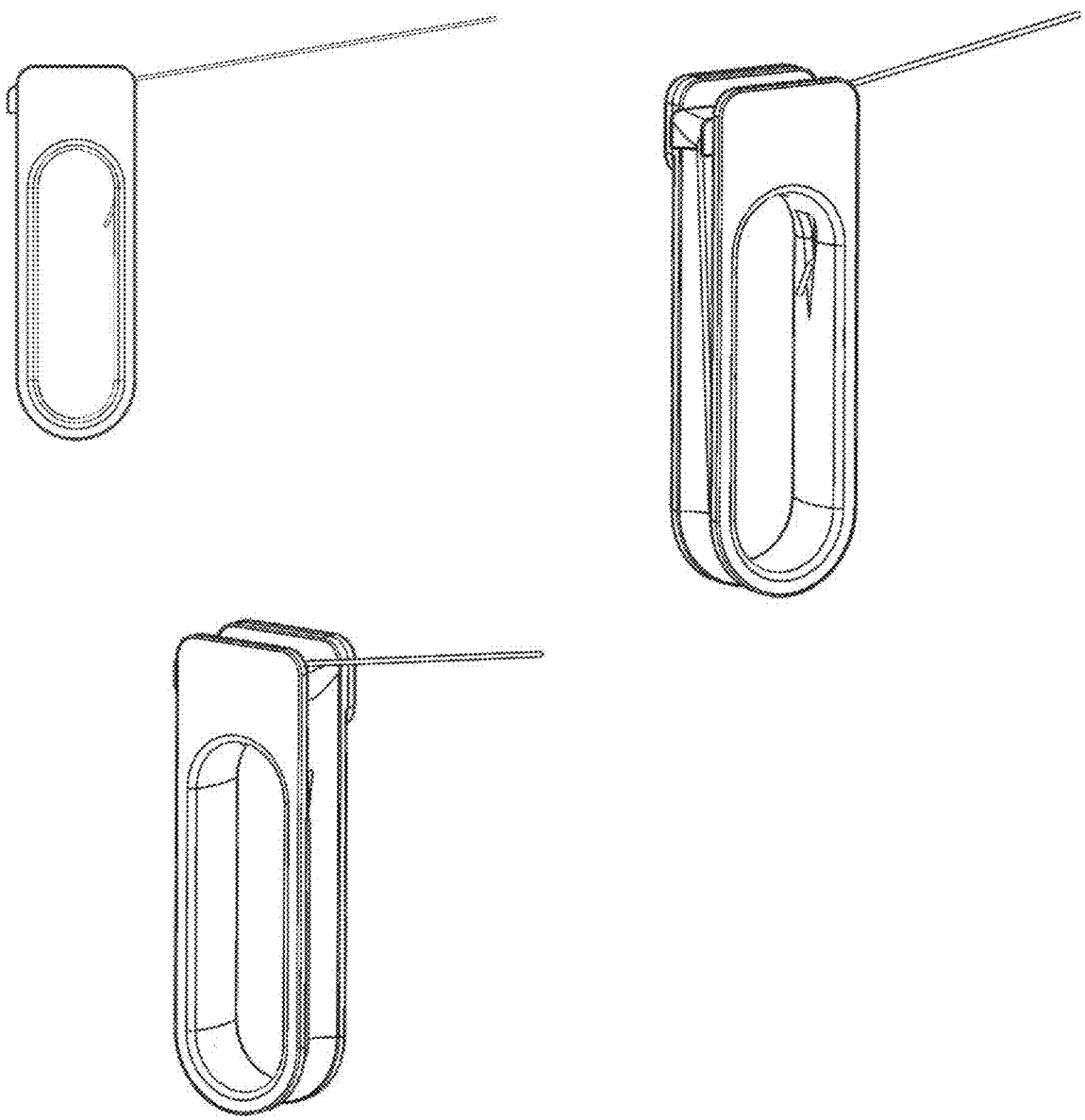
FIG. 35 are schematic views of exemplary pulling accessory device, according to some embodiments of the present invention.

In some embodiments, a pulling accessory device is used. In some embodiments, the pulling accessory device is as shown, for example, in FIG. 35. Exemplary characteristics related to the handle accessory are disclosed above in section 11.

12.5 Exemplary Tissue and Binding Site Assessment Accessory

In some embodiments, accessories allowing to classify matter distally of any LE device are provided. In some embodiments, the accessories work in the same manner as described above in sections 4.9 and 4.10.

12.6 Exemplary Lead Cutter Accessory

As mentioned above, in some cases, during the lead extraction procedure, the user arrives at the conclusion that the lead cannot be taken out from the tissue without causing too much damage. In these cases, it may be preferable to cut the reminder of the lead instead of forcing it out.

In some embodiments, a lead cutter accessory is provided. In some embodiments, the lead cutter accessory slides around the lead when the extractor is out or while the extractor is still in position, where a cut is needed by the user.

Figure 36A:
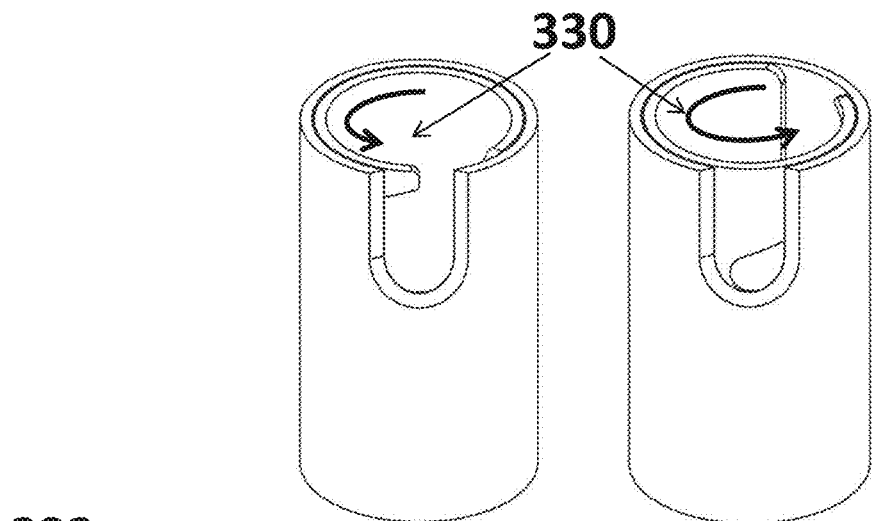
FIGS. 36a-g are schematic views of exemplary lead cutting accessory device, according to some embodiments of the present invention.
Figure 36B:
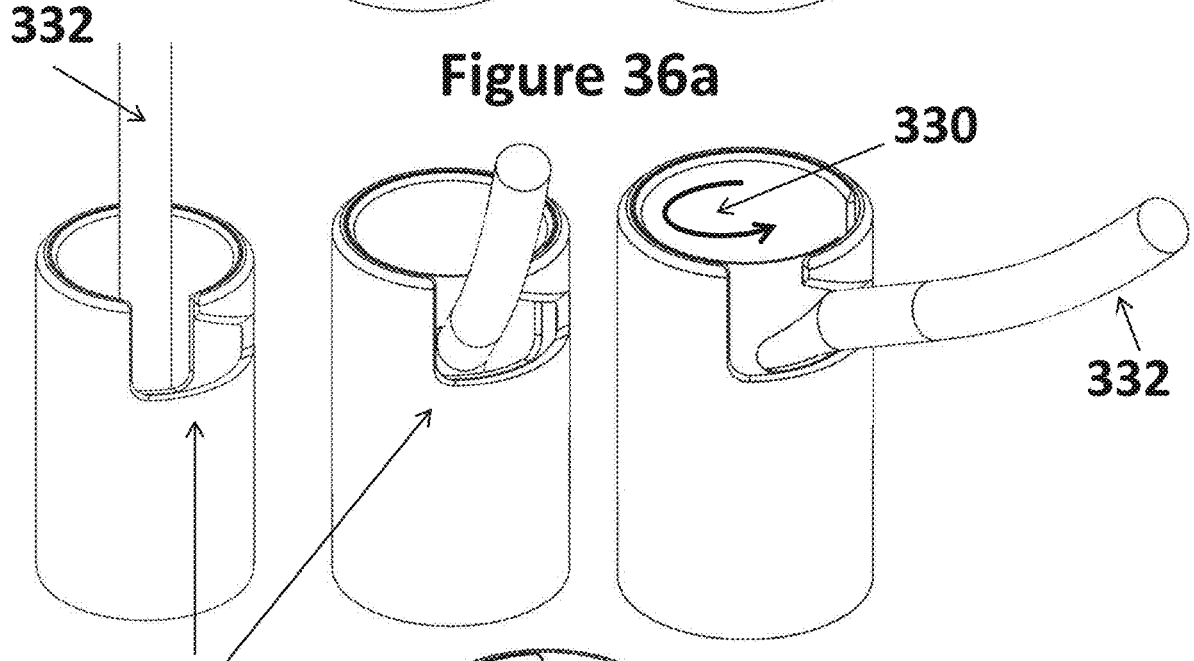
Figure 36B:
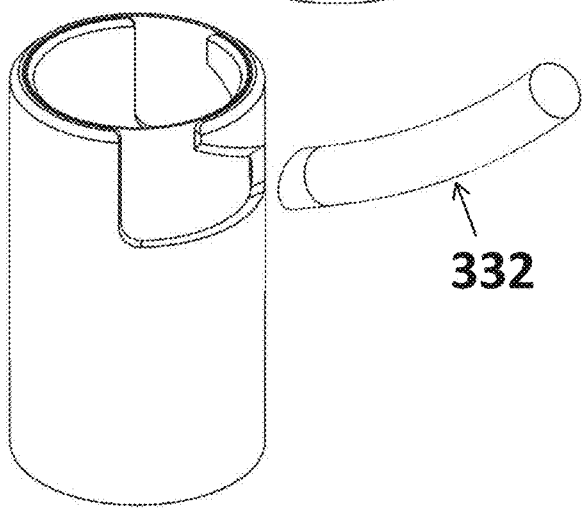

In some embodiments, the lead cutter comprises at least one rotating/sliding plate 330, as shown for example in FIG. 36*a*. In some embodiments, the action of cutting the lead is as shown in FIG. 36*b*, and it is, for example, as follows:

The lead 332 passes through the lead cutter accessory. When the user brings the device to the desired point where the lead 332 needs to be cut, the user moves the distal end of the device so as to insert the lead 332 into the groove 334. Once the lead 332 is in the groove 334, the user activated the rotating plate 330, which cuts the lead 332.

In some embodiments, the distance between blades in the cutting mechanisms is zero. In some embodiments, the distance between blades in the cutting mechanisms is negative and at least one blade is made of flexible metals or other materials, which adapts to the second blade during the cutting action.

In some embodiments, the lead cutter accessory comprises different mechanisms, which ensure that the lead does not move, or escape from the cutting zone. In some embodiments, the sliding of the rotating plate is from right to left and/or to left to right. In some embodiments, where the cutting edge is sharp, the cutting mechanism will be forced to have a phase to make a cut. In some embodiments, the edge is designed to be safe for use in the internal organs. In some embodiments, the lead cutter can be redrawn and/or reloaded after a cutting attempt was done for relocating or replacing a tool, according to the user decision.

Figure 36C:
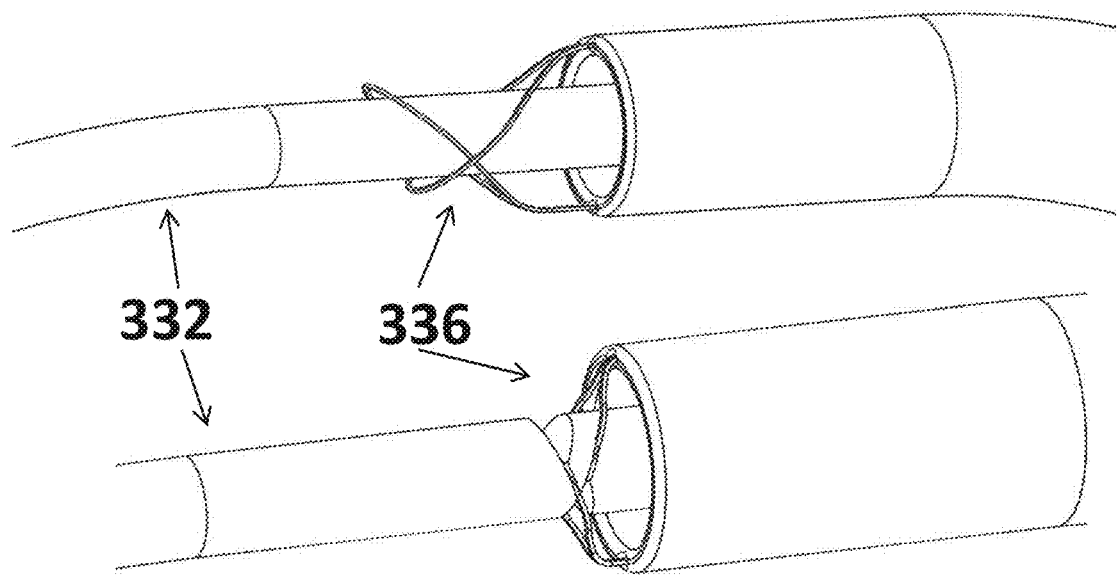

In some embodiments, the lead cutter accessory comprises at least 2 wires 336 which choke the lead 332, and by using pressure, and/or by pulling the wire or wires back and forward or in one direction, the wires cut the lead, as shown for example in FIG. 36*c*.

Figure 36D:
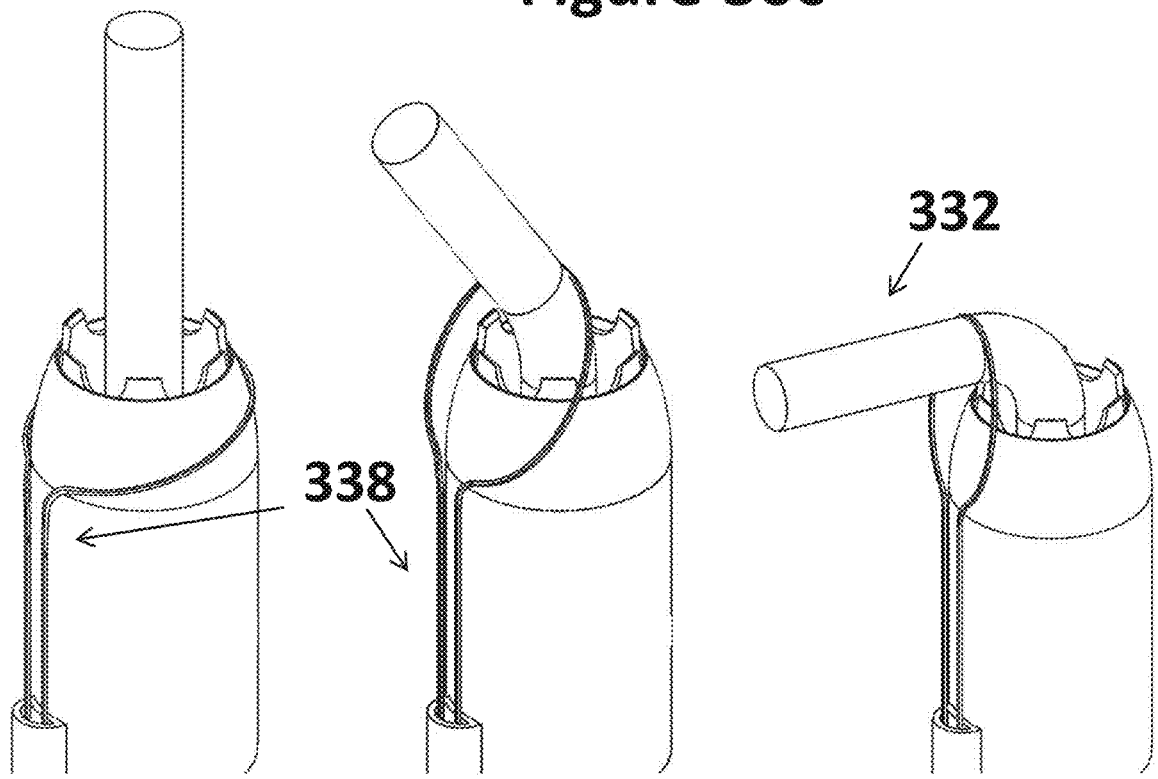

In some embodiments, another mechanism of a lead cutter accessory comprises a wider device 338 that goes around the extractor, as shown for example in FIG. 36*d*. In this embodiment, a wire-like 338 is shown to exit from an external additional elongated tube running parallel to the LE device. In some embodiments, the wire-like is made, for example, of nitinol or any other material. In some embodiments, the wire is in a non-deployed state hugging the LE device. In some embodiments, a dedicated groove is used to keep the wire in its non-deployed state. In some embodiments, the groove is perpendicular to the LE device. In some embodiments, the groove is non-perpendicular to the LE device, having a diagonal orientation. In some embodiments, the wire "natural" memory state is in an opposite orientation related to the non-deployed state. This means that, once deployed, the wire will try to return to the "natural" memory state, which is moving apart from the LE device, as shown in the right upper corner of FIG. 36*d*. In some embodiments, the external additional elongated tube running parallel to the LE device and containing the wire is irreversibly attached to the LE device. In some embodiments, the external additional elongated tube running parallel to the LE device and containing the wire is reversibly attached to the LE device. In some embodiments, the external additional elongated tube running parallel to the LE device and containing the wire is adapted to move forward and backwards in relation to the LE device.

Figure 36E:
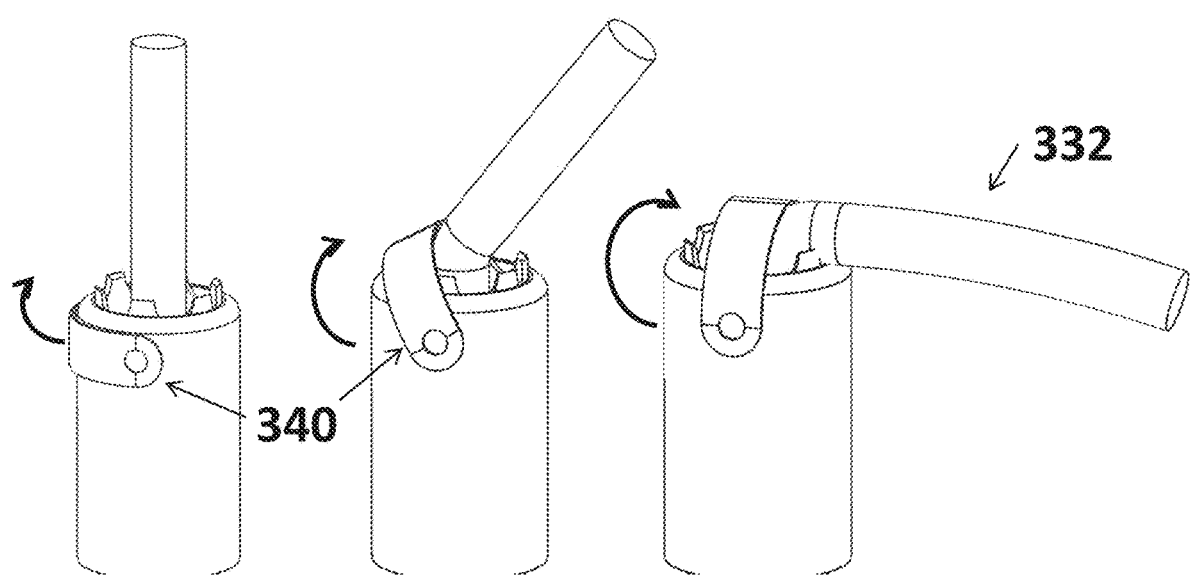

In some embodiments, another mechanism of a lead cutter accessory comprises a wider device 340 that goes around the extractor, as shown for example in FIG. 36*e*. In this embodiment, the wider device comprises a shutter or band 340 attached to the distal end at two points. In some embodiments, when activated, the band moves distally towards the distal end pushing the lead towards the cutting blades of the tissue cutter, until the pressure is enough to hold the lead against the blades. In some embodiments, the lead is cut by pulling the lead itself. In some embodiments, the lead is cut by the pressure applied by the band against the lead on the blades.

Figure 36F:
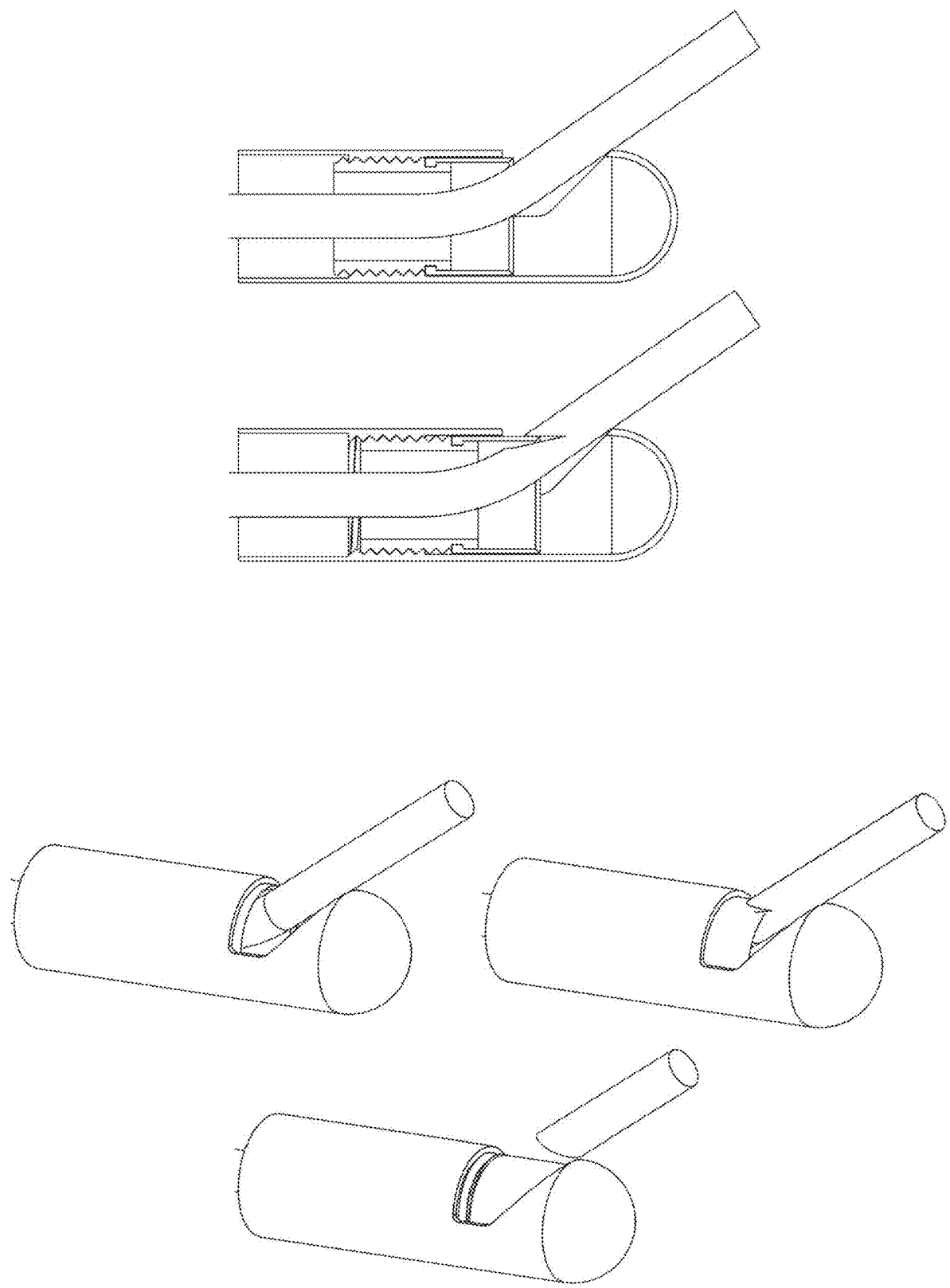

In some embodiments, the lead cutter comprises a linear cutting mechanism, as shown for example in FIG. 36*f*. In some embodiments, this mechanism comprises a channel and a side looking window through which the lead enters. In some embodiments, the sliding cutting part is configured with a cutting angle. In some embodiments, the fixed cutting part is configured with a cutting angle. In some embodiments, the internal part is the movable part in the cutting action. In some embodiments, the external part is the movable part in the cutting action. In some embodiments, the cutting mechanism is a screw rotating mechanism, as shown for example in FIG. 36*f*, upper figures. In some embodiments, the screw mechanism provides further force to the cutting action.

Figure 36G:
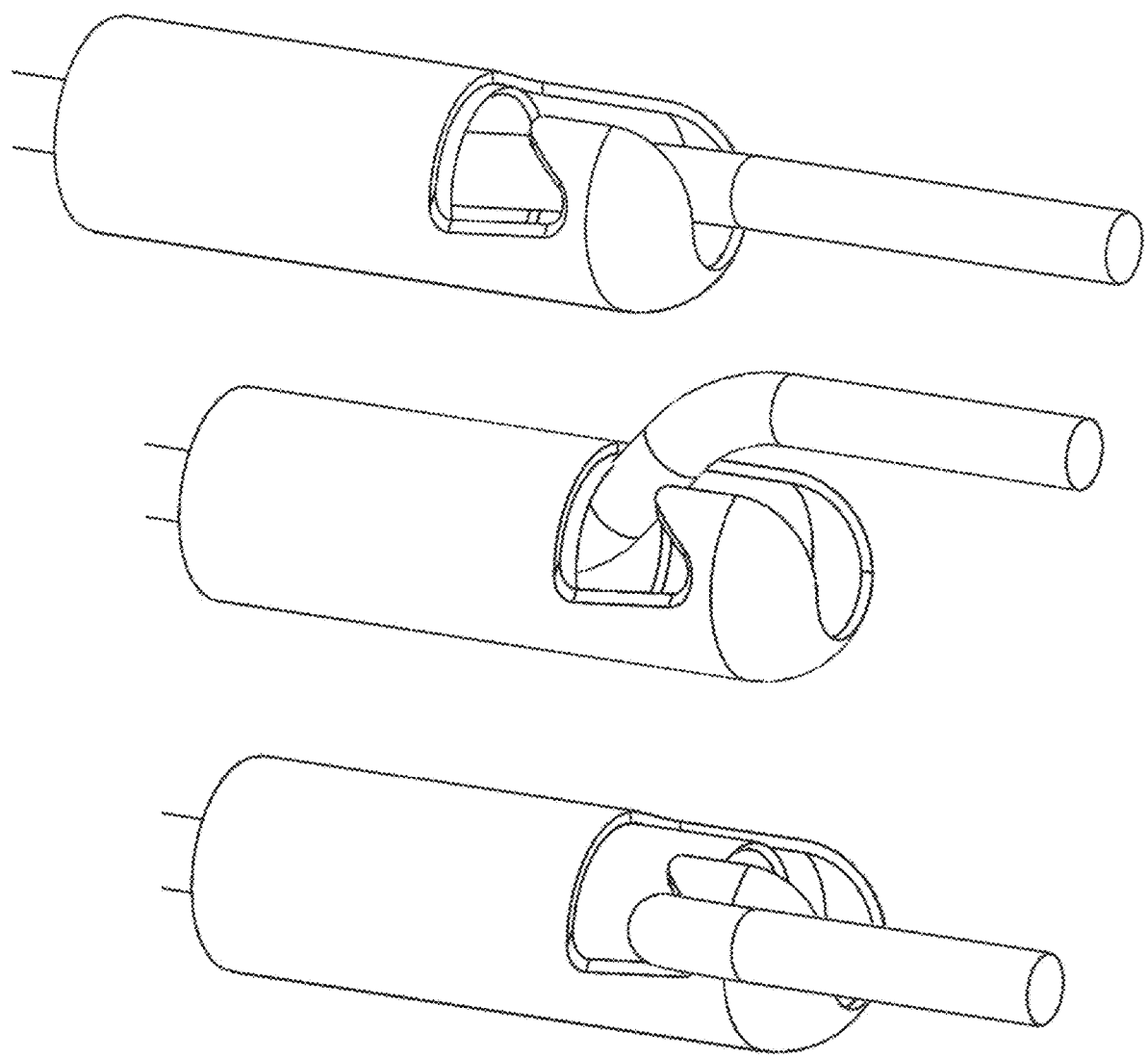

In some embodiments, the specialized groove is located near the distal end of the lead cutter accessory, as shown for example in FIG. 36*g*. In some embodiments, the groove enables the movement of the accessory without damaging the lead or any tissue on its way to the cutting site. In some embodiments, as shown in FIG. 36g, once the lead cutter accessory arrives at the cutting site, the lead in maneuvered into the groove where similar mechanisms to those explained in FIG. 36f are activated to cut the lead.

In some embodiments, the lead cutter comprises a shutter blades mechanism. This mechanism comprises a several blades configured to produce a round shape that closes against the lead and cut it.

13. Exemplary Methods

Figure 37:
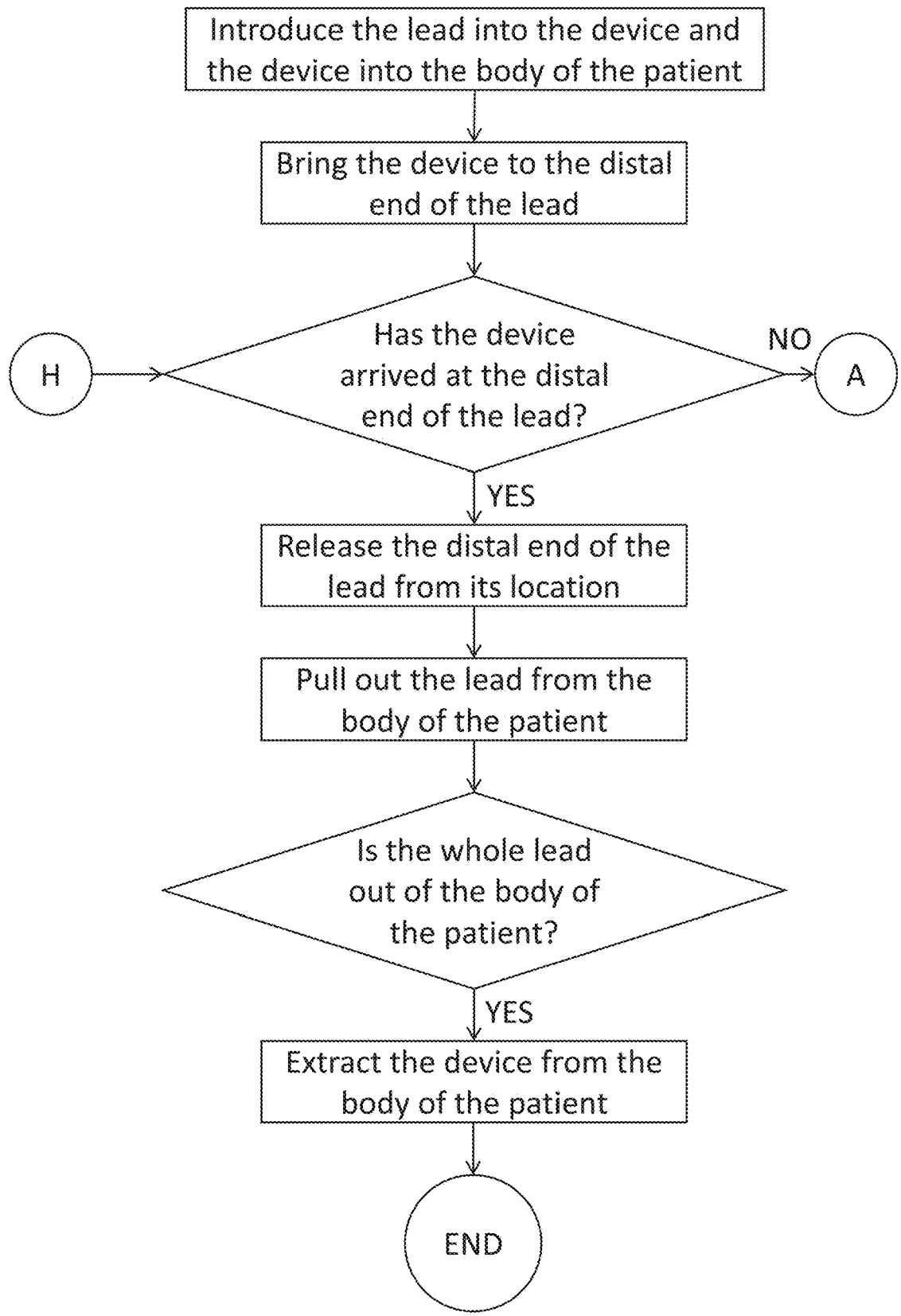
FIGS. 37, 38, 39 and 40 are schematic flowcharts of exemplary methods, according to some embodiments of the present invention.

In some embodiments, the following methodology is performed when using a lead extraction device, for example, as disclose above:

Reference is now made to the flowchart shown in FIG. 37: once the leads are exposed from the chest cavity, the user inserts the lead inside the device, and then the device inside the body of the patient. In the ideal conditions, the user is able to bring the distal end of the device to the distal end of the lead, near its place in the heart. Then the user detaches the lead from the heart, extracts the whole lead through the device outside the body of the patient. The procedure ends by extracting the device from the body of the patient.

As explained above, ideal conditions are difficult to find, especially in patients where the lead has been inside the patient for more than six months. In these cases, lead is usually entrapped by tissue.

Figure 38:
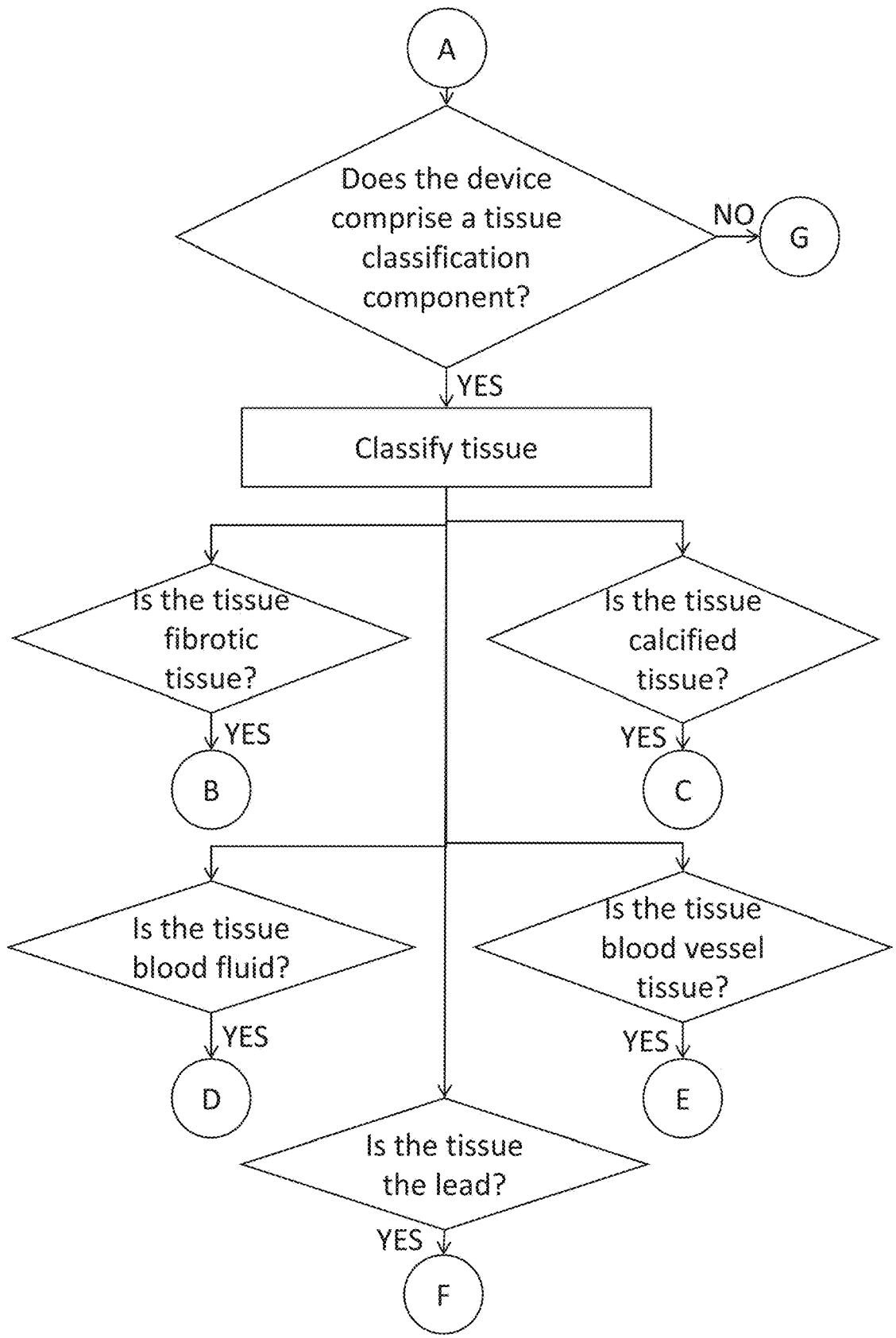
Figure 39:
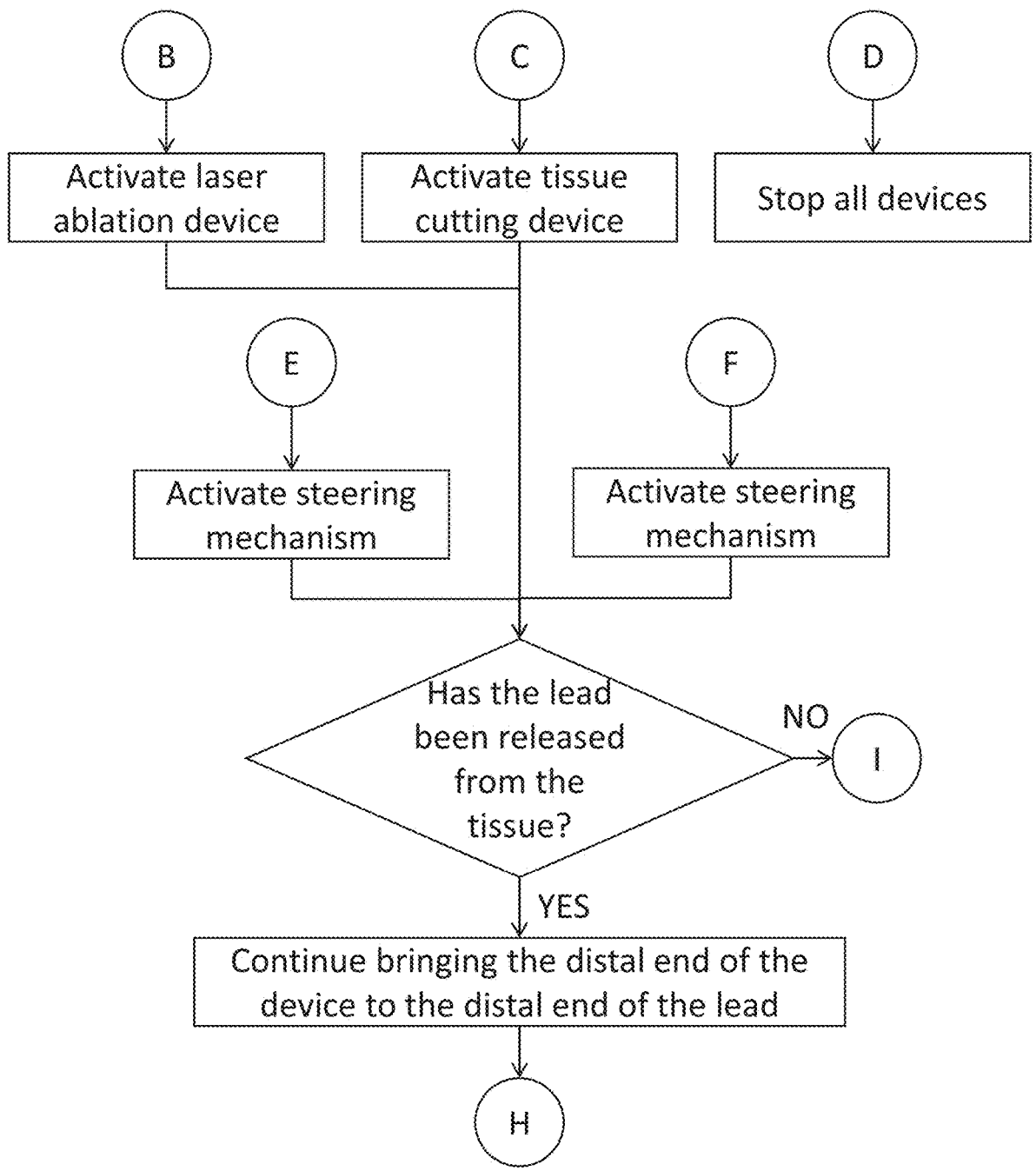

Therefore, once the user feels that the device cannot continue to follow the lead (following the letter "A" to FIG. 38), the user optionally activates the tissue classification component, if the device is equipped with one. The component can identify what kind of tissue is found in front of the distal end of the device. In the case where fibrotic tissue is found (following the letter "B" to FIG. 39), the user can choose, in some embodiments, to activate the laser ablation device. Optionally, he can also choose to activate the tissue cutting device. In the case where calcified tissue is found (following the letter "C" to FIG. 39), the user can choose, in some embodiments, to activate the tissue cutting device. Optionally, it can also choose to activate the laser ablation device. In the case where blood fluid is found (following the letter "D" to FIG. 39), the user can choose to stop all devices and assess if damage was caused to the blood vessel. In the case where blood vessel tissue is found (following the letter "E" to FIG. 39), the user can choose, in some embodiments, to activate the steering mechanism in order to direct the device towards the path of the lead. In some cases, the tissue classification component can identify that is the lead in front of the device and that is the lead itself that is not allowing the device to continue. In this case (following the letter "F" to FIG. 39), the user can choose, in some embodiments, to activate the steering mechanism in order to align the device in the direction of the lead, centralizing the lead, as much as possible, within the device to avoid damaging the lead. In any of the above cases, once the lead is released from the tissue, the user will continue bringing the device to the distal end of the lead to release it (following the letter "H" to FIG. 37).

Figure 40:
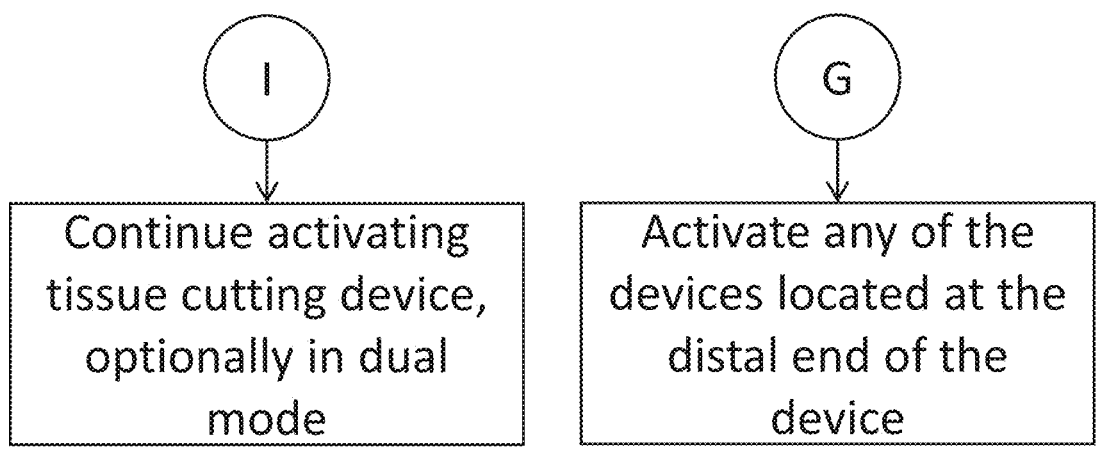

In some embodiments, where the lead is strongly buried in the tissue, the user can choose (following the letter "I" to FIG. 40), in some embodiments, to activate from the handle the dual cutting mechanism comprising linear cutting movement and circular cutting movement, including the "hammer-like" strikes, on the tissue.

In some embodiments, where the device is not equipped with a tissue classification component (following the letter "G" to FIG. 40), the user can choose to activate from the handle any of the components located in the distal end of the device, for example the tissue spreaders, the tissue cutting devices, the laser ablation device, and any combination thereof, depending on his professional assessment of the situation. For example, switching between laser ablation and tissue cutting devices if the one in use does not provide efficient progress. In another example, the user may choose a cautious approach when in doubt, choosing a device less likely to damage the lead or blood vessel, as the situation is understood by the user.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A cardiac lead extraction system, comprising:
   a. a handle;
   b. an elongated body in communication with said handle;
   c. an external bendable flexible portion in communication with said elongated body, said external bendable flexible portion comprising a first lumen sized and shaped to fit over a cardiac lead; said external bendable flexible portion being more flexible than said elongated body;
   d. an operational distal end in communication with said external bendable flexible portion;
   wherein said external bendable flexible portion is configured to bend to a bending radius of less than 4 cm while keeping said first lumen open;
   wherein said operational distal end comprises at least one lead extraction assistive tool, said operational distal end comprising a second lumen sized and shaped to fit over said cardiac lead, said second lumen being in communication with said first lumen, and said first lumen comprises an inner diameter of from about 1 mm to about 5 mm;
   wherein said system comprises a pedal in communication with said handle, said pedal configured for activating said operational distal end; and
   wherein said operational distal end comprises at least one impact mechanism positioned within said operational distal end, said at least one impact mechanism comprising at least one spring and at least one movable component; said at least one spring configured to provide momentum to said at least one movable component which performs an impact action once said at least one spring is released.

2. The system of claim 1, wherein said system further comprises a controllable steering mechanism configured to orient said operational distal end.

3. The system of claim 2, wherein said controllable steering mechanism comprises at least one wire that runs from said handle to said operational distal end, and wherein said at least one wire runs inside a counter sleeve on said elongated body.

4. The system of claim 1, wherein said external bendable flexible portion is configured to bend to a minimum bending radius of from about 2 mm to about 15 mm.

5. The system of claim 1, wherein said external bendable flexible portion comprises at least one articulated structure configured to maintain said first lumen open.

6. The system of claim 1, wherein an outer diameter of said cardiac lead extraction system is from about 5 mm to about 8 mm.

7. The system of claim 1, wherein said external bendable flexible portion bends to a maximal angle of from about 35 degrees to about 150 degrees.

8. The system of claim 7, wherein an inner diameter of said external bendable flexible portion changes in length from about 0% to about 10% during said maximal angle.

9. The system of claim 7, wherein one or more of the following is true:
   a. said external bendable flexible portion is capable of bending to said maximal angle during active deflection of the system while withstanding forces up to 3000 gf;
   b. said external bendable flexible portion is capable of bending to said maximal angle during passive deflection of the system while withstanding forces up to 500 gf.

10. The system of claim 1, wherein said external bendable flexible portion is configured to perform a movement from 0 degrees to about 180 degrees.

11. The system of claim 1, wherein:
   a. said elongated body comprises a first proximal end, a first distal end, and a third lumen extending from said first proximal end toward said first distal end, said third lumen sized and shaped to fit over said cardiac lead; and
   b. said external bendable flexible portion comprises a second proximal end, a second distal end and said first lumen extending from said second proximal end toward said second distal end, said second lumen sized and shaped to fit over said cardiac lead.

12. The system of claim 1, further comprising a motor.

13. The system of claim 12, wherein said motor is located at said handle.

14. The system of claim 12, wherein said motor is located at said pedal.

15. The system of claim 1, wherein said pedal is used to activate and control said at least one lead extraction assistive tool.

16. The system of claim 1, wherein said handle is used to activate and control said at least one lead extraction assistive tool.

17. The system of claim 1, wherein said at least one lead extraction assistive tool comprises one or more components configured to perform repeatable movement at a repetition rate of from about 1 Hz to about 100 Hz.

18. The system of claim 17, wherein said repetition rate is from about 5 Hz to about 60 Hz.

19. The system of claim 1, wherein said at least one lead extraction assistive tool comprises a tissue cutter.

20. The system of claim 19, wherein said tissue cutter comprises at least one movable blade.

21. The system of claim 20, wherein said tissue cutter comprises at least one transmission attached to a motor; said at least one transmission adapted to transfer motion from said motor to said at least one movable blade.

22. The system of claim 21, wherein said motion of said at least one movable blade is linear.

23. The system of claim 21, wherein said motion of said at least one movable blade is circular.

24. The system of claim 21, wherein said motion of said at least one transmission is configured to provide said at least one movable blade with a linear motion comprising an impact force to apply on tissue.

25. The system of claim 21, wherein said motion of said at least one movable blade is a combination of linear movement and circular movement.

26. The system of claim 21, wherein said motion of said at least one movable blade is characterized by a frequency from about 0.5 Hz to about 100 Hz.

27. The system of claim 21, wherein said motion of said at least one movable blade is characterized by a frequency from about 1 Hz to about 15 Hz.

28. The system of claim 21, wherein said at least one movable blade comprises a retracted state where said at least one movable blade is not exposed thereby minimizing said at least one movable blade from damaging tissue.

29. The system of claim 21, wherein said at least one movable blade exits distally said operational distal end from about 0.15 mm to about 2 mm.

30. The system of claim 19, wherein said tissue cutter comprises at least two movable blades.

31. The system of claim 30, wherein a relative movement of said at least two movable blades provides cutting by shearing.

32. The system of claim 1, wherein said external bendable flexible portion comprises at least one internal structure configured to transmit motion from said handle to said operational distal end through said elongated body.

33. The system of claim 1, wherein said lead extraction assistive tool comprises a lead cutter.

\* \* \* \* \*